United States Patent
MacDonald et al.

(10) Patent No.: US 7,538,121 B2
(45) Date of Patent: May 26, 2009

(54) VANILLOID RECEPTOR MODULATORS

(75) Inventors: Gregor James MacDonald, Trumpington (GB); Darren Jason Mitchell, Harlow (GB); Harshad Kantilal Rami, Harlow (GB); Mervyn Thompson, Harlow (GB); Susan Marie Westaway, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 540 days.

(21) Appl. No.: 10/503,648

(22) PCT Filed: Feb. 13, 2003

(86) PCT No.: PCT/GB03/00608

§ 371 (c)(1), (2), (4) Date: Sep. 26, 2005

(87) PCT Pub. No.: WO03/068749

PCT Pub. Date: Aug. 21, 2003

(65) Prior Publication Data

US 2006/0142333 A1 Jun. 29, 2006

(30) Foreign Application Priority Data

| Feb. 15, 2002 | (GB) | ..... 0203673 |
| Feb. 15, 2002 | (GB) | ..... 0203677 |
| Feb. 15, 2002 | (GB) | ..... 0203680 |
| Apr. 19, 2002 | (GB) | ..... 0209003 |
| Apr. 19, 2002 | (GB) | ..... 0209032 |
| Apr. 19, 2002 | (GB) | ..... 0209035 |
| Sep. 13, 2002 | (GB) | ..... 0221318 |

(51) Int. Cl.
C07D 403/02 (2006.01)
A61K 31/47 (2006.01)

(52) U.S. Cl. ............. 514/310; 514/314; 546/148; 546/149

(58) Field of Classification Search .......... None
See application file for complete search history.

(56) References Cited

U.S. PATENT DOCUMENTS 3,200,123 A   8/1965  Richardson, Jr. et al.
4,803,162 A * 2/1989  Smith et al. .............. 435/36
4,954,498 A * 9/1990  Mertens et al. .......... 514/252.02

FOREIGN PATENT DOCUMENTS

| DE | 21 01 691   | 3/1972 |
| EP | 1 099 701   | 5/2001 |
| WO | WO 96 40640 | 12/1996 |
| WO | WO 97 48683 | 12/1997 |
| WO | WO 98 41508 | 9/1998 |
| WO | WO 00 69849 | 11/2000 |
| WO | WO 01 21577 | 3/2001 |
| WO | WO 01 62737 | 8/2001 |
| WO | WO 02 08221 | 1/2002 |

OTHER PUBLICATIONS

Hishashi Shinkai, "4-Aminoquinolines: novel nociceptin antagonists with analgesic activity", J. Med. Chem., vol. 43, No. 24, 2000, pp. 4667-4677, XP002239650.
J. Jaen et al.: "Kynurenic acid derivatives inhibit the ginding of Nerve Growth Factor (NGF) to the Low-Afinity p. 75 NGF receptor", J.MED.CHEM., vol. 38, No. 2, 1995, pp. 4439-4445, XP002239651.
Szallasi, A. et al., "Vanilloid (Capsaicin) Receptors and Mechanisms", Pharmacological Reviews, Williams and Wilkins Inc., Baltimore, MD, US, vol. 51, No. 2, 1999, pp. 159-211, XP001105620 ISSN: 0031-6997.
Wai. N. Chan et al.: "Evaluation of a series of anticonvulsant 1,2,3,4-tetrahydroisoquinolinolinyl-benzamides" BIOORG.MED. CHEM., vol. 8, 2000, pp. 2085-2094, P002239649.

* cited by examiner

Primary Examiner—Zinna N Davis
(74) Attorney, Agent, or Firm—Reid S. Willis; Charles Kinzig

(57) ABSTRACT

Certain compounds of formula (I),

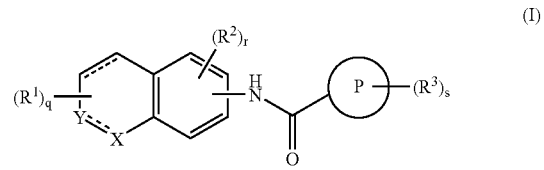

or a pharmaceutically acceptable salt or solvate thereof, wherein $R^1$, $R^2$, $R^3$, P, X, Y, q, r ans s are as defined in the specification, a process for preparing such compounds, a pharmaceutical composition comprising such compounds and the use of such compounds in medicine.

7 Claims, No Drawings

VANILLOID RECEPTOR MODULATORS

This application is a 371 of PCT/GB03/00608 filed Feb. 13, 2003.

This invention relates to novel amide derivatives having pharmacological activity, processes for their preparation, to compositions containing them and to their use in medicine, especially in the treatment of various disorders.

Vanilloids are a class of natural and synthetic compounds that are characterised by the presence of a vanillyl (4-hydroxy 3-methoxybenzyl) group or a functionally equivalent group. Vanilloid Receptor (VR-1), whose function is modulated by such compounds, has been widely studied and is extensively reviewed by Szallasi and Blumberg (The American Society for Pharmacology and Experimental Therapeutics, 1999, Vol. 51, No. 2.).

A wide variety of Vanilloid compounds of different structures are known in the art, for example those disclosed in European Patent Application Numbers, EP 0 347 000 and EP 0 401 903, UK Patent Application Number GB 2226313 and International Patent Application, Publication Number WO 92/09285. Particularly notable examples of vanilloid compounds or vanilloid receptor modulators are capsaicin or trans 8-methyl-N-vanillyl-6-nonenamide which is isolated from the pepper plant, capsazepine (*Tetrahedron*, 53, 1997, 4791) and olvanil or —N-(4-hydroxy-3-methoxybenzyl)oleamide (*J. Med. Chem.*, 36, 1993, 2595).

International Patent Application, Publication Number WO 02/08221 discloses diaryl piperazine and related compounds which bind with high selectivity and high affinity to vanilloid receptors, especially Type I Vanilloid receptors, also known as capsaicin or VR1 receptors. The compounds are said to be useful in the treatment of chronic and acute pain conditions, itch and urinary incontinence.

International Patent Application, Publication Numbers WO 02/16317, WO 02/16318 and WO 02/16319 suggest that compounds having a high affinity for the vanilloid receptor are useful for treating stomach-duodenal ulcers.

U.S. Pat. No. 3,424,760 and U.S. Pat. No. 3,424,761 both describe a series of 3-Ureidopyrrolidines that are said to exhibit analgesic, central nervous system, and pyschopharmacologic activities. These patents specifically disclose the compounds 1-(1-phenyl-3-pyrrolidinyl)-3-phenyl urea and 1-(1-phenyl-3-pyrrolidinyl)-3-(4-methoxyphenyl)urea respectively.

International Patent Applications, Publication Numbers WO 01/62737 and WO 00/69849 disclose a series of pyrazole derivatives which are stated to be useful in the treatment of disorders and diseases associated with the NPY receptor subtype Y5, such as obesity. WO 01/62737 specifically discloses the compound 5-amino-N-isoquinolin-5-yl-1-[3-(trifluoromethyl)phenyl]-1H-pyrazole-3-carboxamide. WO 00/69849 specifically discloses the compounds 5-methyl-N-quinolin-8-yl-1-[3-(trifluoromethyl)phenyl]-1H-pyrazole-3-carboxamide, 5-methyl-N-quinolin-7-yl-1-[3-trifluoromethyl)phenyl]-1H -pyrazole-3-carboxamide, 5-methyl-N-quinolin-3-yl-1-[3-(trifluoromethyl)phenyl]-1H-pyrazole-3-carboxamide, N-isoquinolin-5-yl-5-methyl-1-[3-(trifluoromethyl)phenyl]-1H -pyrazole-3-carboxamide, 5-methyl-N-quinolin-5-yl-1-[3-(trifluoromethyl)phenyl]-1H-pyrazole-3-carboxamide, 1-(3-chlorophenyl)-N-isoquinolin-5-yl-5-methyl-1H-pyrazole-3-carboxamide, N-isoquinolin-5-yl-1-(3-methoxyphenyl)-5-methyl-1H -pyrazole-3-carboxamide, 1-(3-fuorophenyl)-N-isoquinolin-5-yl-5-methyl-1H -pyrazole-3-carboxamide, 1-(2-chloro-5-trifluoromethylphenyl)-N-isoquinolin-5-yl-5-methyl-1H-pyrazole-3-carboxamide, 5-methyl-N-(3-methylisoquinolin-5-yl)-1-[3-(trifluoromethyl)phenyl]-1H-pyrazole-3-carboxamide, 5-methyl-N-(1,2,3,4-tetrahydroisoquinolin-5-yl)-1-[3-(trifluoromethyl)phenyl]-1H-pyrazole-3-carboxamide.

German Patent Application Number 2502588 describes a series of piperazine derivatives. This application specifically discloses the compound N-[3-[2-(diethylamino)ethyl]-1,2-dihydro-4-methyl-2-oxo-7-quinolinyl]-4-phenyl-1-piperazinecarboxamide.

We have now discovered that certain compounds falling within the scope of International Patent Application, Publication Number WO 02/08221 have surprising potency and selectivity as VR-1 antagonists. The compounds of the present invention are considered to be particularly beneficial as VR-1 antagonists as certain compounds exhibit improved aqueous solubility and metabolic stability relative to the compounds disclosed in WO 02/08221.

According to a first aspect of the present invention, there is provided a compound of formula (I),

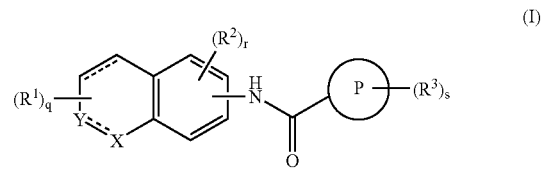

or a pharmaceutically acceptable salt or solvate thereof, wherein,

P is selected from phenyl, heteroaryl or heterocyclyl;

$R^1$ and $R^2$ are independently selected from halo, alkyl, alkoxy, cycloalkyl, aralkyl, aralkoxy, cycloalkylalkyl, cycloalkylalkoxy, —CN, —$NO_2$, —OH, =O, —$OCF_3$, —$CF_3$, —$NR^4R^5$, —$S(O)_mR^6$, —$S(O)_2NR^4R^5$, —$OS(O)_2R^6$, —$OS(O)_2CF_3$, —$O(CH_2)_nNR^4R^5$, —$C(O)CF_3$, —C(O)alkyl, —C(O)cycloalkyl, —C(O)aralkyl, —C(O)Ar, —$C(O)(CH_2)_nOR^6$, —$C(O)(CH_2)_nNR^4R^5$, —C(O)alkoxy, —$C(O)NR^4R^5$, —$(CH_2)_nC(O)$alkoxy, —$(CH_2)_nOC(O)R^6$, —$O(CH_2)_nOR^6$, —$(CH_2)_nOR^6$, —$(CH_2)_nR^4R^5$, —$(CH_2)_nC(O)NR^4R^5$, —$(CH_2)_nN(R^4)C(O)R^6$, —$(CH_2)_nS(O)_2NR^4R^5$, —$(CH_2)_nN(R^4)S(O)_2R^6$, -ZAr, —$(CH_2)_nS(O)_2R^6$, —$(OCH_2)_nS(O)_2R^6$, —$N(R^4)S(O)_2R^6$, —$N(R^4)C(O)R^6$, —$(CH_2)_nN(R^4)S(O)_2R^6$, —$(CH_2)_nN(R^4)C(O)R^6$ or —$(CH_2)_n$ C(O)alkyl;

$R^3$ is selected from alkyl, alkoxy, —$CF_3$, halo, —$O(CH_2)_nOR^6$, —$O(CH_2)_nNR^4R^5$, phenyl, cyclohexyl, benzo[1,3]dioxolyl, morpholinyl, pyridyl, pyrimidinyl, pyrazinyl, piperazinyl, piperidinyl, pyridizinyl, thienyl, furyl, pyrazolyl, pyrrolyl, triazolyl, indanyl, imidazolyl, oxazolyl, thiazolyl, oxadiazolyl, isothiazolyl, isoxazolyl or thiadiazolyl; wherein said alkyl, alkoxy, phenyl, cyclohexyl, benzo[1,3]dioxolyl, morpholinyl, pyridyl, pyrimidinyl, pyrazinyl, piperazinyl, piperidinyl, pyridizinyl, thienyl, furyl, pyrazolyl, pyrrolyl, triazolyl, indanyl, imidazolyl, oxazolyl, thiazolyl, oxadiazolyl, isothiazolyl, isoxazolyl and thiadiazolyl groups may be optionally substituted by one or more groups, which may be the same or different, selected from $R^2$;

$R^4$ and $R^5$ may be the same or different and represent —H or alkyl or $R^4$ and $R^5$ together with the nitrogen atom to which they are attached form a heterocyclic ring;

$R^6$ is —H, alkyl or aryl;

$R^7$ is —H, alkyl or aryl;

$R^8$ is selected from —H, alkyl, hydroxyalkyl, cycloalkyl, aralkyl, alkoxyalkyl, cycloalkylalkyl, heterocyclylalkyl, —S(O)$_m$R$^6$, —C(O)CF$_3$, —C(O)alkyl, —C(O)cycloalkyl, —C(O)aralkyl, —C(O)Ar, —C(O)(CH$_2$)$_n$OR$^6$, —C(O)(CH$_2$)$_n$NR$^4$R$^5$, —C(O)alkoxy, —C(O)NR$^4$R$^5$, —(CH$_2$)$_n$C(O)alkoxy, —(CH$_2$)$_n$OC(O)R$^6$, —(CH$_2$)$_n$OR$^6$, —(CH$_2$)$_n$R$^4$R$^5$, —(CH$_2$)$_n$C(O)NR$^4$R$^5$, —(CH$_2$)$_n$N(R$^4$)C(O)R$^6$, —(CH$_2$)$_n$S(O)$_2$NR$^4$R$^5$, —(CH$_2$)$_n$N(R$^4$)S(O)$_2$R$^6$, —(CH$_2$)$_n$S(O)$_2$R$^6$, —(CH$_2$)$_n$N(R$^4$)S(O)$_2$R$^6$, —(CH$_2$)$_n$N(R$^4$)C(O)R$^6$ or —(CH$_2$)$_n$C(O)alkyl; or where X is NR$^8$ and Y is C(R$^9$)$_2$, R$^8$ may combine with R$^1$ to form a benzoquinuclidine group;

$R^9$ is —H or $R^1$;

Ar is aryl or heteroaryl, each of which may be optionally substituted by $R^2$;

Z is a bond, O, S, NR$^7$ or CH$_2$;

m is 0, 1 or 2;

n is an integer value from 1 to 6;

q and r are independently selected from 0, 1, 2 or 3;

s is 0, 1, 2 or 3; and

X and Y are selected from the following combinations:

| X | Y |
| --- | --- |
| N | CR$^9$ |
| NR$^8$ | C(R$^9$)$_2$ |
| CR$^9$ | N |
| C(R$^9$)$_2$ | NR$^8$ | with the proviso that said compound of formula (I) is not a compound selected from:

N-{3-[(N,N-Dimethylamino)methyl]-1,2,3,4-tetrahydro-7-quinolinyl}-4-biphenylcarboxamide;

N-{3-[(N,N-Dimethylamino)methyl]-1-formyl-1,2,3,4-tetrahydro-7-quinolinyl}-4-biphenylcarboxamide;

N-{1-Acetyl-3-[(N,N-dimethylamino)methyl]-1,2,3,4-tetrahydro-7-quinolinyl}-4-biphenylcarboxamide;

N-{3-[(N,N-Dimethylamino)methyl]-1-methylsulfonyl-1,2,3,4-tetrahydro-7-quinolinyl}-4-biphenylcarboxamide;

5-amino-N-isoquinolin-5-yl-1-[3-(trifluoromethyl)phenyl]-1H-pyrazole-3-carboxamide;

5-methyl-N-quinolin-8-yl-1-[3-(trifluoromethyl)phenyl]-1H-pyrazole-3-carboxamide, 5-methyl-N-quinolin-7-yl-1-[3-trifluoromethyl)phenyl]-1H-pyrazole-3-carboxamide, 5-methyl-N-quinolin-3-yl-1-[3-(trifluoromethyl)phenyl]-1H-pyrazole-3-carboxamide, 5-isoquinolin-5-yl-5-methyl-1-[3-(trifluoromethyl)phenyl]-1H-pyrazole-3-carboxamide, 5-methyl-N-quinolin-5-yl-1-[3-(trifluoromethyl)phenyl]-1H-pyrazole-3-carboxamide, 1-(3-chlorophenyl)-N-isoquinolin-5-yl-5-methyl-1H-pyrazole-3-carboxamide, N-isoquinolin-5-yl-1-(3-methoxyphenyl)-5-methyl-1H-pyrazole-3-carboxamide, 1-(3-fuorophenyl)-N-isoquinolin-5-yl-5-methyl-1H-pyrazole-3-carboxamide, 1-(2-chloro-5-trifluoromethylphenyl)-N-isoquinolin-5-yl-5-methyl-1H-pyrazole-3-carboxamide, 5-methyl-N-(3-methylisoquinolin-5-yl)-1-[3-(trifluoromethyl)phenyl]-1H-pyrazole-3-carboxamide, 5-methyl-N-(1,2,3,4-tetrahydroisoquinolin-5-yl)-1-[3-(trifluoromethyl)phenyl]-1H-pyrazole-3-carboxamide; and N-[3-[2-(diethylamino)ethyl]-1,2-dihydro-4-methyl-2-oxo-7-quinolinyl]-4-phenyl-1-piperazinecarboxamide.

Suitably, P is phenyl, pyridyl, furanyl, thienyl, piperazinyl, piperidinyl or fluorenyl. Suitably, P is phenyl or pyridyl. Suitably, P is furanyl, thienyl, piperazinyl, piperidinyl or fluorenyl. More suitably, P is phenyl. More suitably, P is pyridyl.

Suitably, $R^1$ is =O or alkyl. More suitably, $R^1$ is =O or methyl.

Suitably, $R^2$ is halo. More suitably, $R^2$ is bromo or chloro.

Suitably, $R^3$ is alkyl, alkoxy, halo, —CF$_3$, —O(CH$_2$)$_n$OR$^6$, —O(CH$_2$)$_n$NR$^4$R$^5$, phenyl, thienyl, imidazolyl, pyridyl, pyrazinyl, indanyl, piperazinyl, pyrazolyl, benzo[1,3]dioxolyl, morpholinyl, piperidinyl, cyclohexyl or thiazolyl; wherein said alkyl, phenyl, thienyl, imidazolyl, pyridyl, pyrazinyl, indanyl, piperazinyl, pyrazolyl, benzo[1,3]dioxolyl, morpholinyl, piperidinyl, cyclohexyl and thiazolyl groups may be optionally substituted by one or more groups, which may be the same or different, selected from $R^2$. Suitably, $R^3$ is phenyl, alkyl, alkoxy, halo, —CF$_3$, —O(CH$_2$)$_n$OR$^6$, —O(CH$_2$)$_n$NR$^4$R$^5$, phenyl, thienyl, imidazolyl, pyridyl, pyrazinyl, indanyl, piperazinyl, pyrazolyl, benzo[1,3]dioxolyl, morpholinyl, piperidinyl, cyclohexyl or thiazolyl; wherein said alkyl, phenyl, thienyl, imidazolyl, pyridyl, pyrazinyl, indanyl, piperazinyl, pyrazolyl, benzo[1,3]dioxolyl, morpholinyl, piperidinyl, cyclohexyl and thiazolyl groups may be optionally substituted by one or more groups, which may be the same or different, selected from —H, halo, —CF$_3$, alkyl, alkoxy, =O, —CONR$^4$R$^5$, —N(R$^4$)C(O)R$^6$, —C(O)alkyl, —S(O)$_2$NR$^4$R$^5$, —C(O)alkoxy, —O(CH$_2$)$_n$OR$^6$ and —O(CH$_2$)$_n$R$^4$R$^5$. Suitably, $R^3$ is phenyl or pyridyl; each of which may be optionally substituted by one or more groups, which may be the same or different, selected from $R^2$. Suitably, $R^3$ is phenyl or pyridyl; each of which may be optionally substituted by one or more groups, which may be the same or different, selected from —H, halo, —CF$_3$, alkyl, alkoxy, =O, —CONR$^4$R$^5$, —N(R$^4$)C(O)R$^6$, —C(O)alkyl, —S(O)$_2$NR$^4$R$^5$, —C(O)alkoxy, —O(CH$_2$)$_n$OR$^6$ and —O(CH$_2$)$_n$R$^4$R$^5$.

Suitably, $R^4$ is —H or alkyl.

Suitably, $R^5$ is —H or alkyl.

Suitably, $R^6$ is alkyl.

Suitably, $R^8$ is —H, alkyl, hydroxyalkyl, alkoxyalkyl, heterocyclylalkyl, —C(O)CF$_3$, —C(O)alkyl, —C(O)(CH$_2$)$_n$OR$^6$, —(CH$_2$)$_n$OC(O)R$^6$, —(CH$_2$)$_n$C(O)alkoxy or —(CH$_2$)$_n$R$^4$R$^5$. More suitably, $R^8$ is —H, methyl, —C(O)CF$_3$, —C(O)Me, —C(O)CH$_2$OMe, —(CH$_2$)$_2$OC(O)Me, —(CH$_2$)$_2$CO$_2$Me, —(CH$_2$)$_2$OH, —(CH$_2$)$_2$O(CH$_2$)$_2$CH$_3$, —(CH$_2$)$_2$OMe, —(CH$_2$)$_2$NMe$_2$, —(CH$_2$)$_2$N(Pr$^i$)$_2$ or —(CH$_2$)$_2$-morpholinyl.

Suitably, $R^9$ is H. Suitably $R^9$ is $R^1$.

Suitably, q and r are independently selected from 0, 1 or 2. Suitably, q and r are independently selected from 0 or 1.

Suitably, s is 0, 1 or 2.

Suitably, X is N and Y is CR$^9$. Suitably, X is NR$^8$ and Y is C(R$^9$)$_2$. Suitably, X is CR$^9$ and Y is N. Suitably, X is C(R$^9$)$_2$ and Y is NR$^8$.

In a further aspect of the present invention there is provided a subset of compounds of formula (I), of formula (IA),

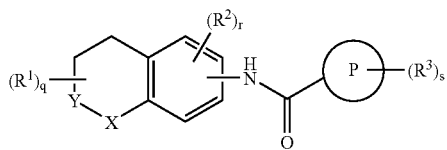

(IA)

or a pharmaceutically acceptable salt or solvate thereof, wherein, P is selected from phenyl, heteroaryl or heterocyclyl;

$R^1$ and $R^2$ are independently selected from halo, alkyl, alkoxy, cycloalkyl, aralkyl, aralkoxy, cycloalkylalkyl, cycloalkylalkoxy, —CN, —$NO_2$, —OH, =O, —$OCF_3$, —$CF_3$, —$NR^4R^5$, —$S(O)_mR^6$, —$S(O)_2NR^4R^5$, —$OS(O)_2R^6$, —$OS(O)_2CF_3$, —$O(CH_2)_nNR^4R^5$, —$C(O)CF_3$, —C(O)alkyl, —C(O)cycloalkyl, —C(O)aralkyl, —C(O)Ar, —$C(O)(CH_2)_nOR^6$, —$C(O)(CH_2)_nNR^4R^5$, —C(O)alkoxy, —$C(O)NR^4R^5$, —$(CH_2)_nC(O)$alkoxy, —$(CH_2)_nOC(O)R^6$, —$O(CH_2)_nOR^6$, —$(CH_2)_nOR^6$, —$(CH_2)_nR^4R^5$—$(CH_2)_nC(O)NR^4R^5$, —$(CH_2)_nN(R^4)C(O)R^6$, —$(CH_2)_nS(O)_2NR^4R^5$, —$(CH_2)_nN(R^4)S(O)_2R^6$, -ZAr, —$(CH_2)_nS(O)_2R^6$, —$(OCH_2)_nS(O)_2R^6$, —$N(R^4)S(O)_2R^6$, —$N(R^4)C(O)R^6$, —$(CH_2)_nN(R^4)S(O)_2R^6$, —$(CH_2)_nN(R^4)C(O)R^6$ or —$(CH_2)_nC(O)$alkyl;

$R^3$ is selected from alkyl, —$CF_3$, halo, phenyl, cyclohexyl, benzo[1,3]dioxolyl morpholinyl, pyridyl, pyrimidinyl, pyrazinyl, piperazinyl piperidinyl, pyridizinyl, thienyl, furyl, pyrazolyl, pyrrolyl, triazolyl, indanyl, imidazolyl, oxazolyl, thiazolyl, oxadiazolyl, isothiazolyl, isoxazolyl or thiadiazolyl; wherein said alkyl, alkoxy, phenyl, cyclohexyl, benzo[1,3]dioxolyl, morpholinyl, pyridyl, pyrimidinyl, pyrazinyl, piperazinyl, piperidinyl, pyridizinyl, thienyl, furyl, pyrazolyl, pyrrolyl, triazolyl, indanyl, imidazolyl, oxazolyl, thiazolyl, oxadiazolyl, isothiazolyl, isoxazolyl and thiadiazolyl groups may be optionally substituted by one or more groups, which may be the same or different, selected from $R^2$;

$R^4$ and $R^5$ may be the same or different and represent —H or alkyl or $R^4$ and $R^5$ together with the nitrogen atom to which they are attached form a heterocyclic ring;

$R^6$ is —H, alkyl or aryl;

$R^7$ is —H, alkyl or aryl;

$R^8$ is selected from —H, alkyl, hydroxyalkyl, cycloalkyl, aralkyl, alkoxyalkyl, cycloalkylalkyl, heterocyclylalkyl, —$S(O)_mR^6$, —$C(O)CF_3$, —C(O)alkyl, —C(O)cycloalkyl, —C(O)aralkyl, —C(O)Ar, —$C(O)(CH_2)_nOR^6$, —$C(O)(CH_2)_nNR^4R^5$, —C(O)alkoxy, —$C(O)NR^4R^5$, —$(CH_2)_nC(O)$alkoxy, —$(CH_2)_nOC(O)R^6$, —$(CH_2)_nOR^6$, —$(CH_2)_nR^4R^5$, —$(CH_2)_nC(O)NR^4R^5$, —$(CH_2)_nN(R^4)C(O)R^6$, —$(CH_2)_nS(O)_2NR^4R^5$, —$(CH_2)_nN(R^4)S(O)_2R^6$, —$(CH_2)_nS(O)_2R^6$, —$(CH_2)_nN(R^4)S(O)_2R^6$, —$(CH_2)_nN(R^4)C(O)R^6$ or —$(CH_2)_nC(O)$alkyl; or where X is $NR^8$ and Y is $C(R^9)_2$, $R^8$ may combine with $R^1$ to form a benzoquinuclidine group;

$R^9$ is —H or $R^1$.

Ar is aryl or heteroaryl, each of which may be optionally substituted by $R^2$;

Z is a bond, O, S, $NR^7$ or $CH_2$;

m is 0, 1 or 2;

n is an integer value from 1 to 6;

q and r are independently selected from 0, 1, 2 or 3;

s is 0, 1, 2 or 3; and

X is $C(R^9)_2$ and Y is $NR^8$ or X is $NR^8$ and Y is $C(R^9)_2$;

with the proviso that said compound of formula (I) is not a compound selected from:

N-{3-[(N,N-Dimethylamino)methyl]-1,2,3,4-tetrahydro-7-quinolinyl}-4-biphenylcarboxamide;

N-{3-[(N,N-dimethylamino)methyl]-1-formyl-1,2,3,4-tetrahydro-7-quinolinyl}-4-biphenylcarboxamide;

N-{1-Acetyl-3-[(N,N-dimethylamino)methyl]-1,2,3,4-tetrahydro-7-quinolinyl}-4-biphenylcarboxamide;

N-{3-[(N,N-Dimethylamino)methyl]-1-methylsulfonyl-1,2,3,4-tetrahydro-7-quinolinyl}-4-biphenylcarboxamide; and 5-methyl-N-(1,2,3,4-tetrahydroisoquinolin-5-yl)-1-[3-(trifluoromethyl)phenyl]-1H-pyrazole-3-carboxamide.

Suitably, P is phenyl, pyridyl, furyl, thienyl or piperazinyl. Suitably, P is phenyl. Suitably, P is pyridyl.

Suitably, $R^1$ is alkyl. More suitably, $R^1$ is methyl.

Suitably, $R^2$ is halo or alkyl.

Suitably, $R^3$ is alkyl, phenyl, indanyl, pyridyl, pyrazinyl, pyrazolyl or thienyl; each of which may be optionally substituted by one or more groups, which may be the same or different, selected from $R^2$. More suitably, $R^3$ is alkyl, phenyl or pyridyl; which phenyl and pyridyl groups may be optionally substituted by alkyl, halo, —$CF_3$, —CONHMe, —NHCOMe, —$CONMe_2$, —C(O)Me, —$SO_2$NHMe, —$CONH_2$.

Suitably, $R^8$ is —H, alkyl, hydroxyalkyl, alkoxyalkyl, heterocyclylalkyl, —$C(O)CF_3$, —C(O)alkyl, —$C(O)(CH_2)_nOR^6$, —$(CH_2)_nOC(O)R^6$, —$(CH_2)_nC(O)$alkoxy or —$(CH_2)_nR^4R^5$. More suitably, $R^8$ is —H, methyl, —$C(O)CF_3$, —C(O)Me, —$C(O)CH_2OMe$, —$C(O)_2OC(O)Me$, —$(CH_2)_2CO_2Me$, —$(CH_2)_2OH$, —$(CH_2)_2O(CH_2)_2CH_3$, —$(CH_2)_2OMe$, —$(CH_2)_2NMe_2$, —$(CH_2)_2N(Pr^i)_2$ or —$(CH_2)_2$-morpholinyl.

Suitably, $R^9$ is H. Suitably, $R^9$ is $R^1$.

Suitably, m is 2.

Suitably, n is 1 or 2.

Suitably, q and r are independently selected from 0, 1 or 2.

Suitably, s is 0, 1 or 2.

Suitably, X is $C(R^9)_2$ and Y is $NR^8$. Suitably, or X is $NR^8$ and Y is $C(R^9)_2$.

In a further aspect of the present invention there is provided a subset of compounds of formula (I), of formula (IB),

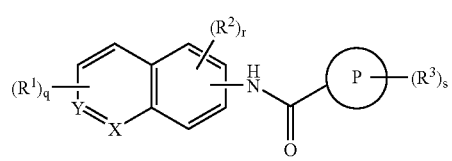

(IB)

or a pharmaceutically acceptable salt or solvate thereof, wherein, P is selected from phenyl, heteroaryl or heterocyclyl;

$R^1$ and $R^2$ are independently selected from halo, alkyl, alkoxy, cycloalkyl, aralkyl, aralkoxy, cycloalkylalkyl, cycloalkylalkoxy, —CN, —NO$_2$, —OH, —OCF$_3$, —CF$_3$, —NR$^4$R$^5$, —S(O)$_m$R$^6$, —S(O)$_2$NR$^4$R$^5$, —OS(O)$_2$R$^6$, —OS(O)$_2$CF$_3$, —O(CH$_2$)$_n$NR$^4$R$^5$, —C(O)CF$_3$, —C(O)alkyl, —C(O)cycloalkyl, —C(O)aralkyl, —C(O)Ar, —C(O)(CH$_2$)$_n$OR$^6$, —C(O)(CH$_2$)$_n$NR$^4$R$^5$, —C(O)alkoxy, —C(O)NR$^4$R$^5$, —(CH$_2$)$_n$C(O)alkoxy, —(CH$_2$)$_n$OC(O)R$^6$, —(CH$_2$)$_n$OR$^6$, —(CH$_2$)$_n$R$^4$R$^5$, —(CH$_2$)$_n$C(O)NR$^4$R$^5$, —(CH$_2$)$_n$N(R$^4$)C(O)R$^6$, —(CH$_2$)$_n$S(O)$_2$NR$^4$R$^5$, —(CH$_2$)$_n$N(R$^4$)S(O)$_2$R$^6$, -ZAr, —(CH$_2$)$_n$S(O)$_2$R$^6$, —(OCH$_2$)$_n$S(O)$_2$R$^6$, —N(R$^4$)S(O)$_2$R$^6$, —N(R$^4$)C(O)R$^6$, —(CH$_2$)$_n$N(R$^4$)S(O)$_2$R$^6$, —(CH$_2$)$_n$N(R$^4$)C(O)R$^6$ or —(CH$_2$)$_n$C(O)alkyl;

R$^3$ is selected from halo, —CF$_3$, alkyl, alkoxy, —O(CH$_2$)$_n$OR$^6$, —O(CH$_2$)$_n$NR$^4$R$^5$, phenyl, cyclohexyl, benzo[1,3]dioxolyl, morpholinyl, pyridyl, pyrimidinyl, pyrazinyl, piperazinyl, piperidinyl, pyridizinyl, thienyl, furyl, pyrazolyl, pyrrolyl, triazolyl, imidazolyl, oxazolyl, thiazolyl, oxadiazolyl, isothiazolyl, isoxazolyl or thiadiazolyl; which alkyl, alkoxy, phenyl, cyclohexyl, benzo[1,3]dioxolyl, morpholinyl, pyridyl, pyrimidinyl, pyrazinyl, piperazinyl, piperidinyl, pyridizinyl, thienyl, furyl, pyrazolyl, pyrrolyl, triazolyl, imidazolyl, oxazolyl, thiazolyl, oxadiazolyl, isothiazolyl, isoxazolyl and thiadiazolyl groups may be optionally substituted by one or more groups, which may be the same or different, selected from R$^2$;

R$^4$ and R$^5$ may be the same or different and represent —H or alkyl or R$^4$ and R$^5$ together with the nitrogen atom to which they are attached form a heterocyclic ring;

R$^6$ is —H, alkyl or aryl;

R$^7$ is —H, alkyl or aryl;

Ar is aryl or heteroaryl; each of which may be optionally substituted by R$^2$;

X and Y are selected from CR$^9$ and N with the proviso that X and Y may not be the same;

Z is a bond, O, S, NR$^7$ or CH$_2$;

m is 0, 1 or 2;

n is an integer value from 1 to 6;

q and r are independently selected from 0, 1, 2 or 3; and s is 0, 1, 2 or 3;

with the proviso that said compound of formula (IB) is not a compound selected from:
5-amino-N-isoquinolin-5-yl-1-[3-(trifluoromethyl)phenyl]-1H-pyrazole-3-carboxamide;
5-methyl-N-quinolin-8-yl-1-[3-(trifluoromethyl)phenyl]-1H-yrazole-3-carboxamide,
5-methyl-N-quinolin-7-yl-1-[3-trifluoromethyl)phenyl]-1H-pyrazole-3-carboxamide,
5-methyl-N-quinolin-3-yl-1-[3-(trifluoromethyl)phenyl]-1H-pyrazole-3-carboxamide,
N-isoquinolin-5-yl-5-methyl-1-[3-(trifluoromethyl)phenyl]-1H-pyrazole-3-carboxamide,
5-methyl-N-quinolin-5-yl-1-[3-(trifluoromethyl)phenyl]-1H-pyrazole-3-carboxamide,
1-(3-chlorophenyl)-N-isoquinolin-5-yl-5-methyl-1H-pyrazole-3-carboxamide,
N-isoquinolin-5-yl-1-(3-methoxyphenyl)-5-methyl-1H-pyrazole-3-carboxamide,
1-(3-fuorophenyl)-N-isoquinolin-5-yl-5-methyl-1H-pyrazole-3-carboxamide,
1-(2-chloro-5-trifluoromethylphenyl)-N-isoquinolin-5-yl-5-methyl-1H-pyrazole-3-carboxamide,
5-methyl-N-(3-methylisoquinolin-5-yl)-1-[3-(trifluoromethyl)phenyl]-1H-pyrazole-3-carboxamide; and
N-[3-[2-(diethylamino)ethyl]-1,2-dihydro-4-methyl-2-oxo-7-quinolinyl]-4-phenyl-1-piperazinecarboxamide.

Suitably, P is phenyl, pyridine, piperazine, piperidine or fluorene. Suitably, P is phenyl. Suitably, P is pyridine.

Suitably, R$^1$ is alkyl. More suitably, R$^1$ is methyl.

Suitably, R$^2$ is halo. More suitably, R$^2$ is chloro.

Suitably, R$^3$ is halo, —CF$_3$, alkyl, alkoxy, —O(CH$_2$)$_n$OR$^6$, —O(CH$_2$)$_n$NR$^4$R$^5$, phenyl, cyclohexyl, benzo[1,3]dioxolyl, morpholinyl, pyridyl, piperazinyl, piperidinyl, pyrazolyl, thienyl, isothiazolyl; which alkyl, phenyl, cyclohexyl, benzo[1,3]dioxolyl, morpholinyl, pyridyl, piperazinyl, piperidinyl, pyrazolyl, thienyl, and isothiazolyl groups may be optionally substituted by one or more groups, which may be the same or different, selected from R$^2$. More suitably, R$^3$ is halo, —CF$_3$, alkyl, alkoxy, —O(CH$_2$)$_n$OR$^6$, —O(CH$_2$)$_n$NR$^4$R$^5$, phenyl, cyclohexyl, benzo[1,3]dioxolyl, morpholinyl, pyridyl, piperazinyl, piperidinyl, pyrazolyl, thienyl, isothiazolyl; which alkyl, phenyl, cyclohexyl, benzo[1,3]dioxolyl, morpholinyl, pyridyl, piperazinyl, piperidinyl, pyrazolyl, thienyl, and isothiazolyl groups may be optionally substituted by one or more groups, which may be the same or different, selected from halo, —CF$_3$, alkyl, alkoxy, —C(O)alkyl, —C(O)alkoxy and —S(O)$_2$NR$^4$R$^5$.

Suitably, q is 0 or 1.

Suitably, r is 0 or 1.

Suitably, s is 0, 1 or 2.

Suitably, X is CR$^9$ and Y is N. Suitably, X is N and Y is CR$^9$.

Preferred compounds according to this invention include Examples 1-133 (as shown below) or pharmaceutically acceptable salts or solvates thereof.

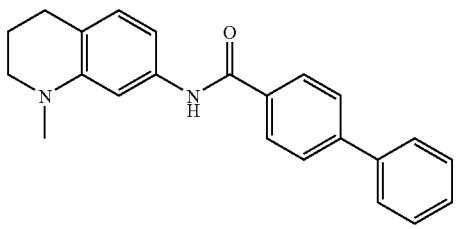

Example 1

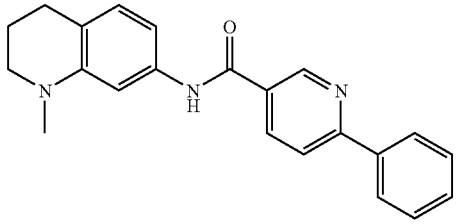

Example 2

Example 3
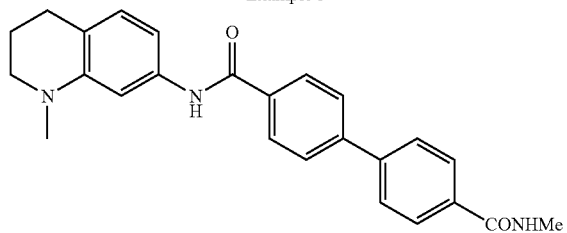
Example 4
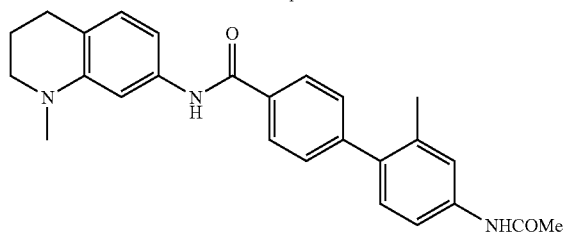
Example 5
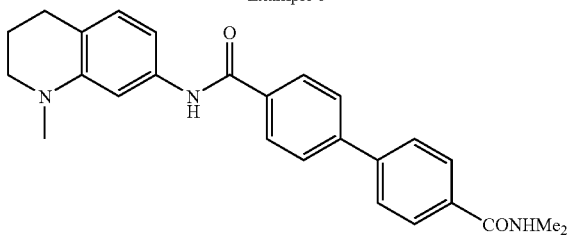
Example 6
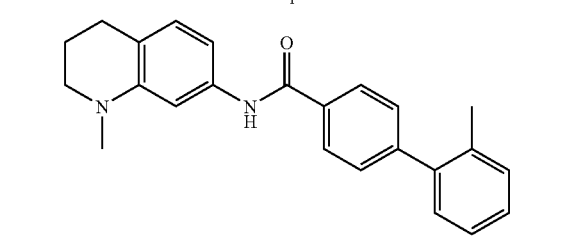
Example 7
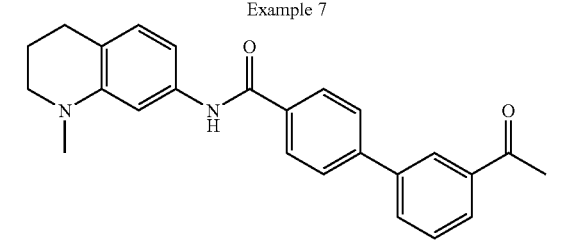
Example 8
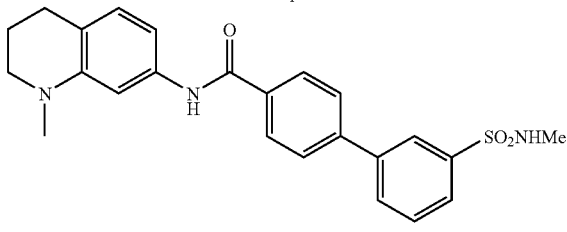
Example 9
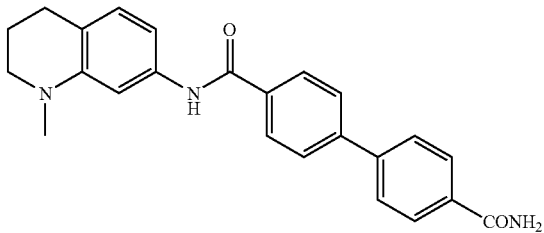
Example 10
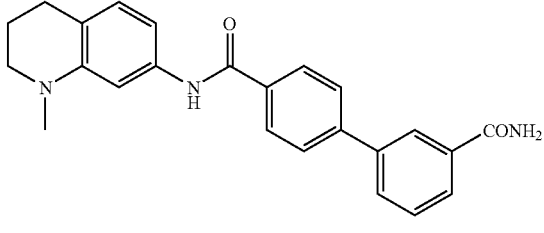
Example 11
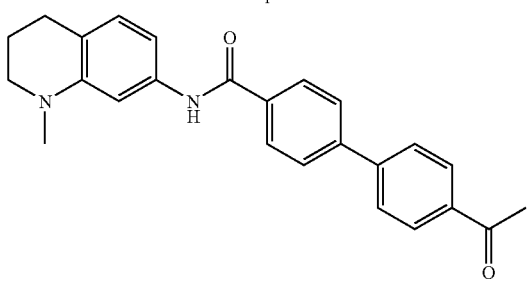
Example 12
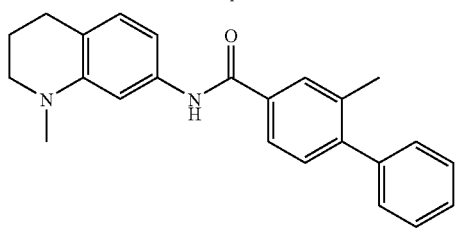
Example 13
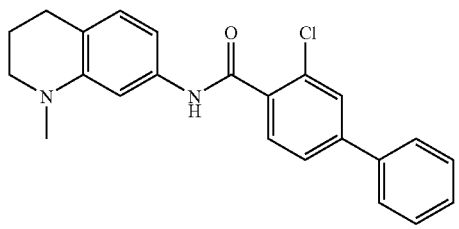
Example 14
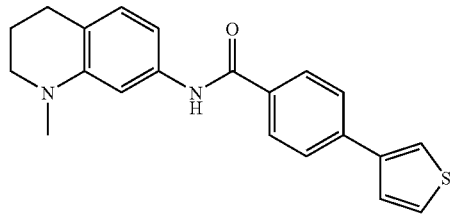

-continued
Example 15
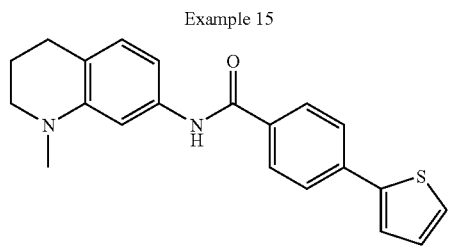
Example 16
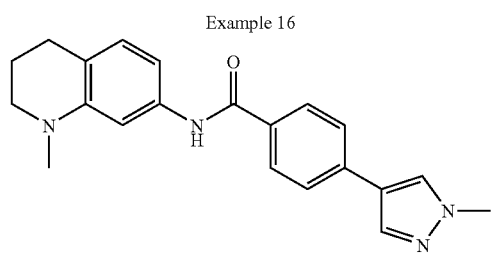
Example 17
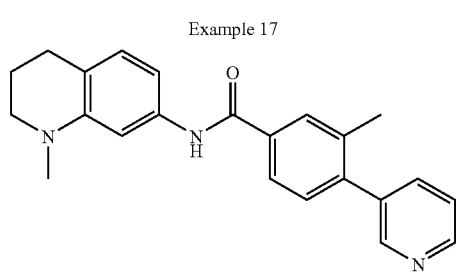
Example 18
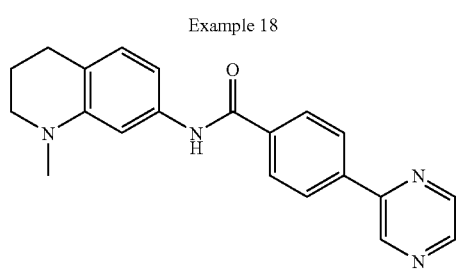
Example 19
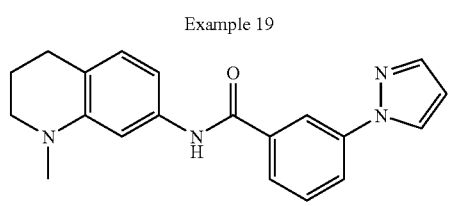
Example 20
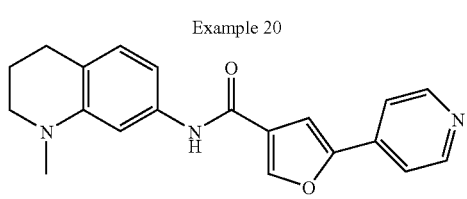
-continued
Example 21
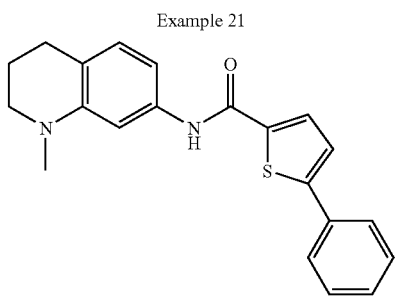
Example 22
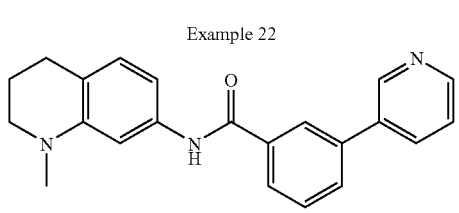
Example 23
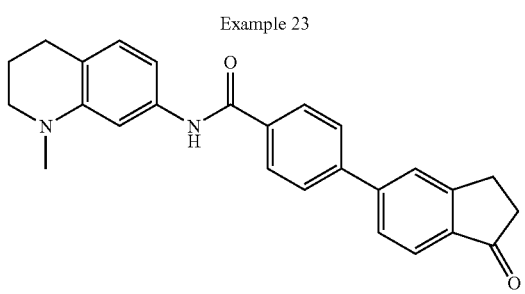
Example 24
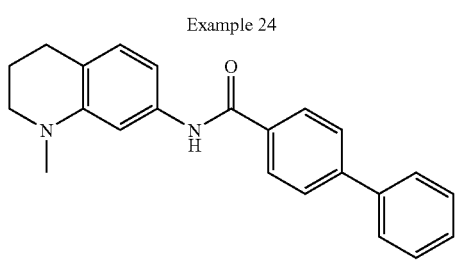
Example 25
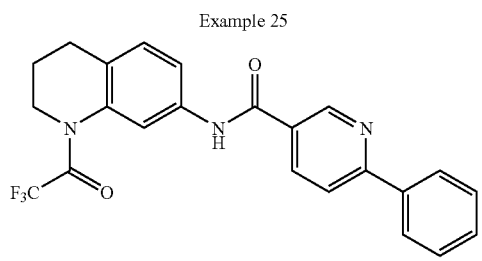
Example 26
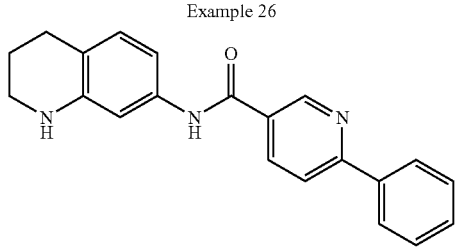

-continued
Example 27
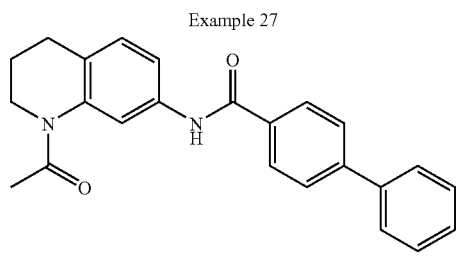
Example 28
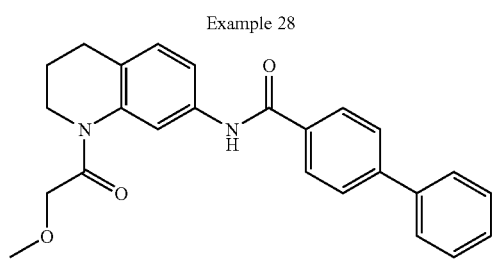
Example 29
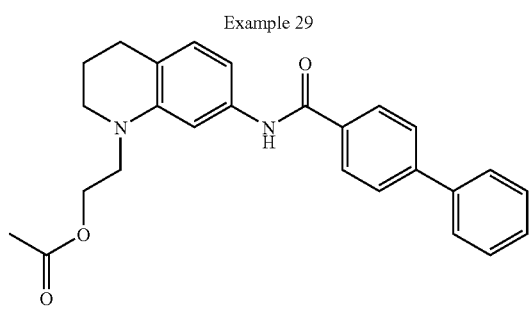
Example 30
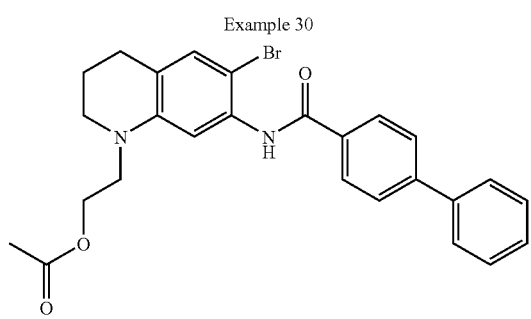
Example 31
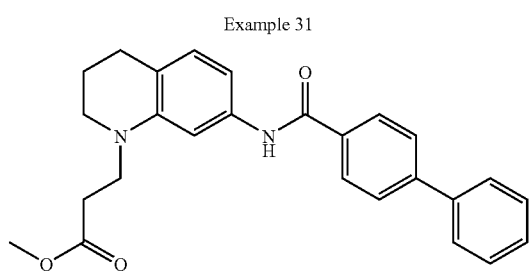
-continued
Example 32
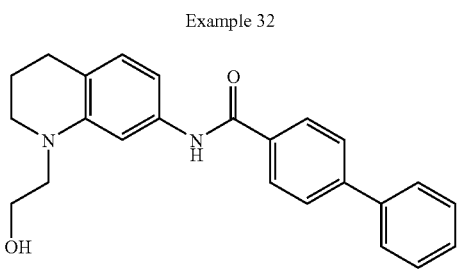
Example 33
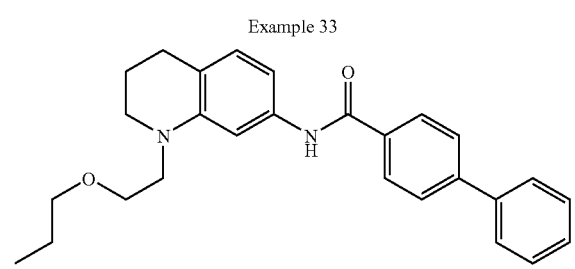
Example 34
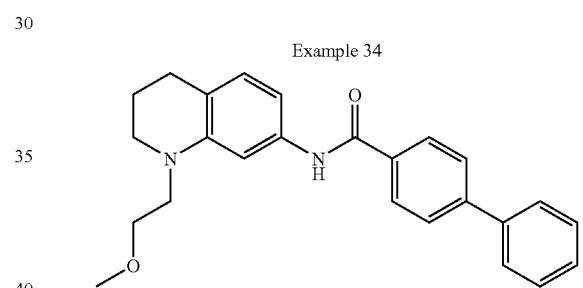
Example 35
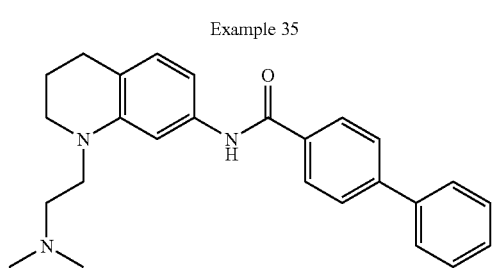
Example 36
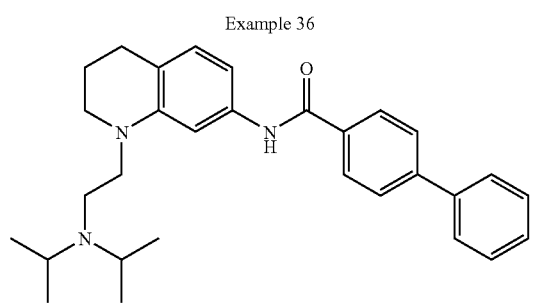

-continued
Example 37
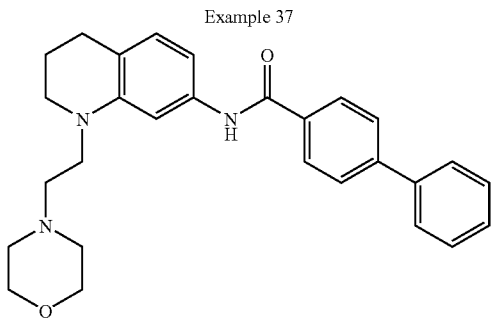
Example 38
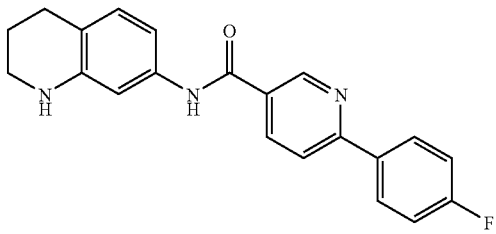
Example 39
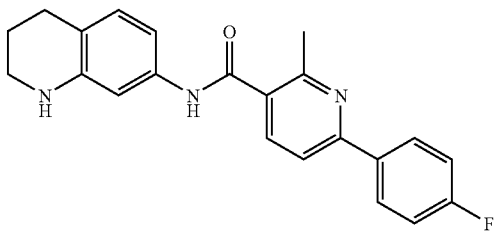
Example 40
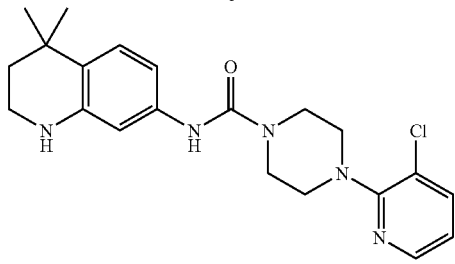
Example 41
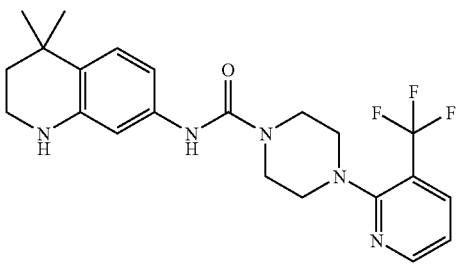
-continued
Example 42
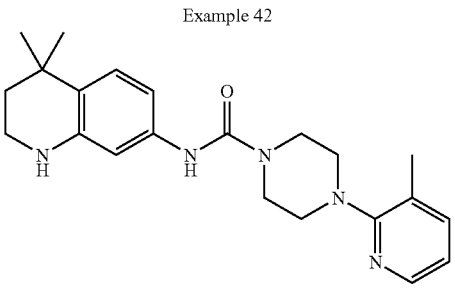
Example 43
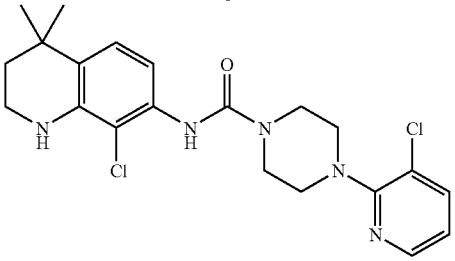
Example 44
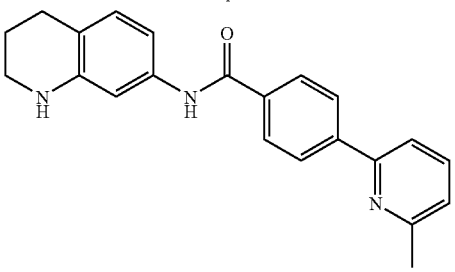
Example 45
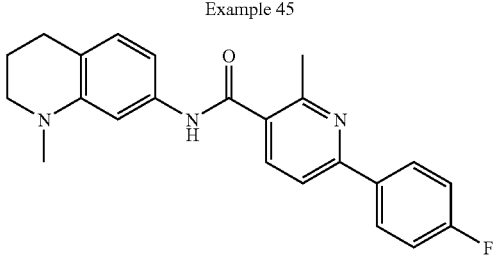
Example 46
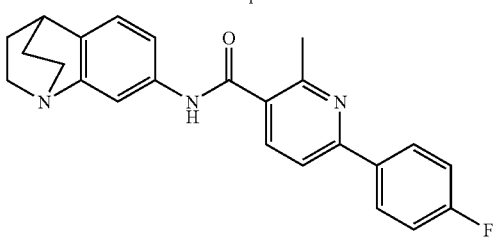

-continued
Example 47
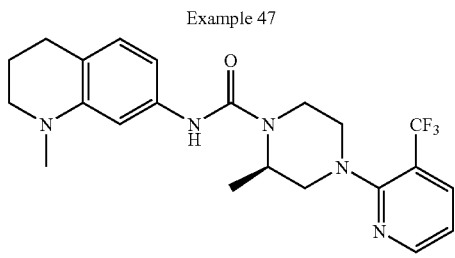
Example 48
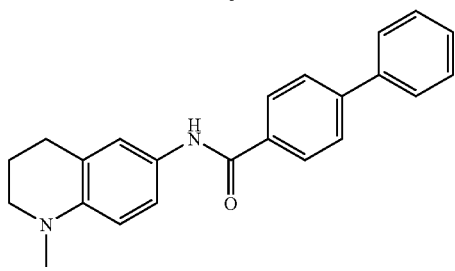
Example 49
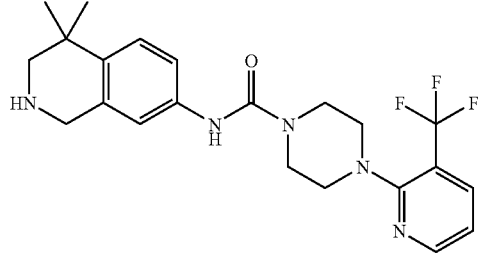
Example 50
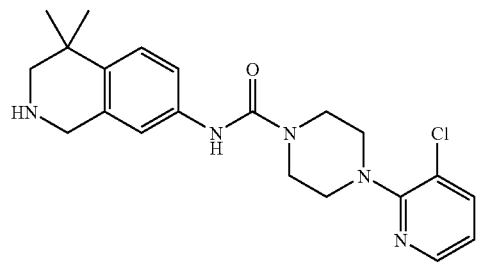
Example 51
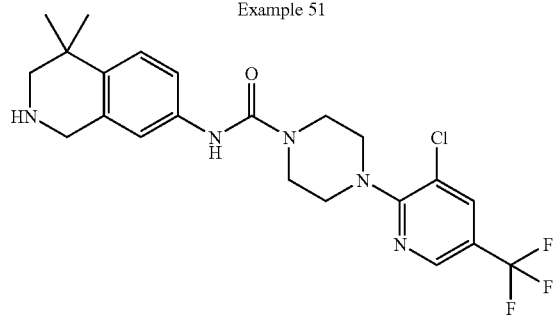
-continued
Example 52
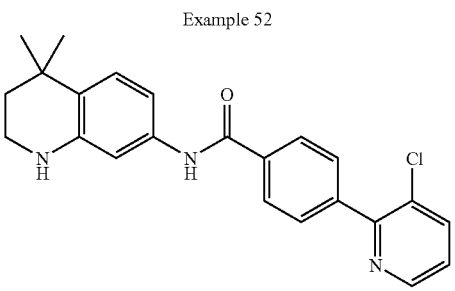
Example 53
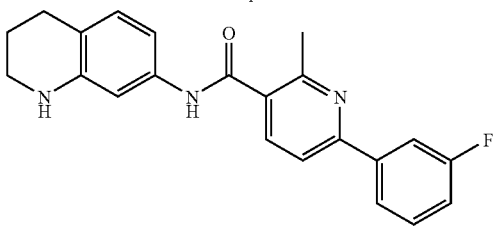
Example 54
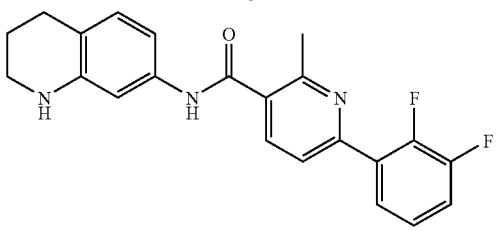
Example 55
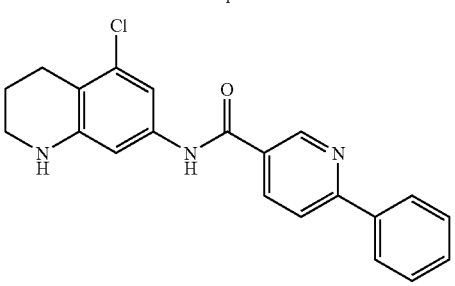
Example 56
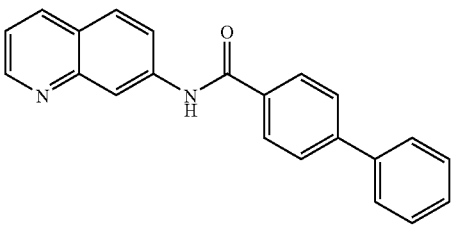

-continued
Example 57
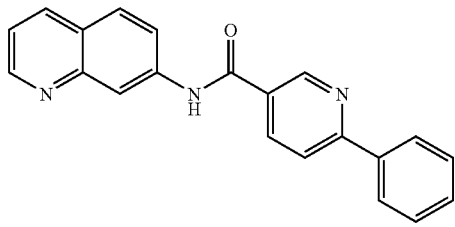
Example 58
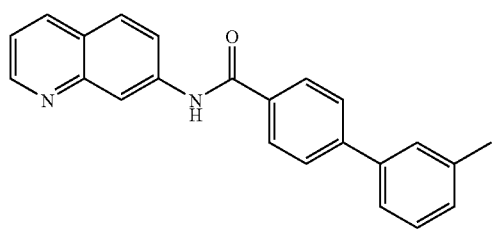
Example 59
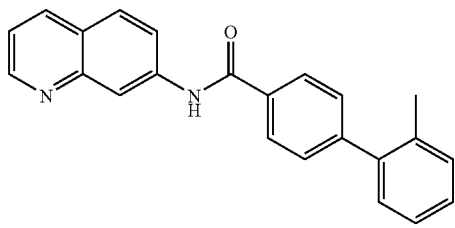
Example 60
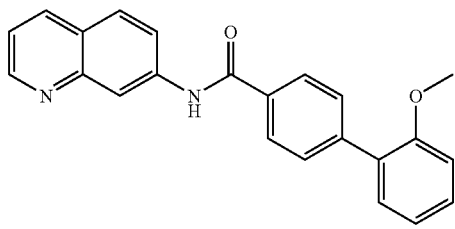
Example 61
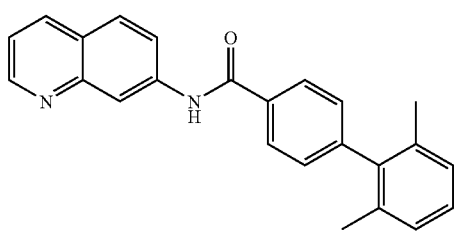
Example 62
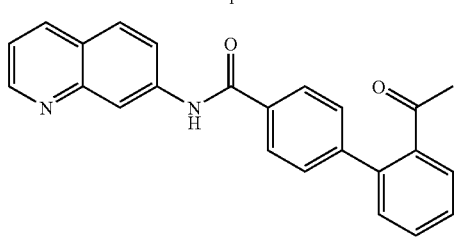
-continued
Example 63
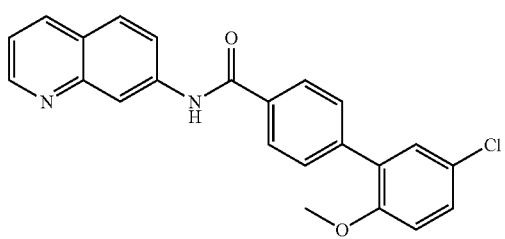
Example 64
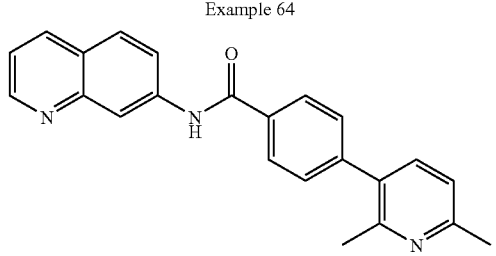
Example 65
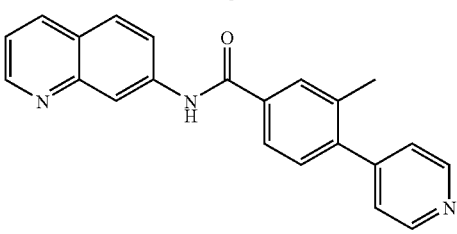
Example 66
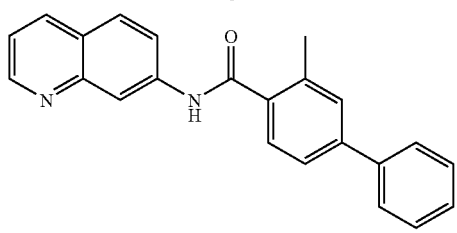
Example 67
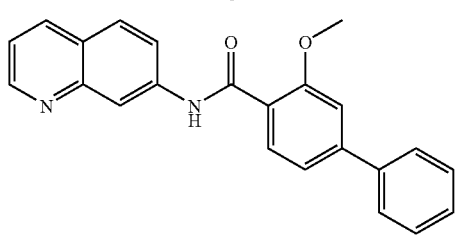
Example 68
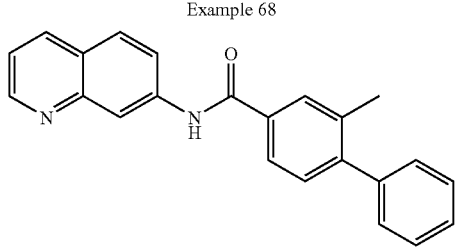

Example 69
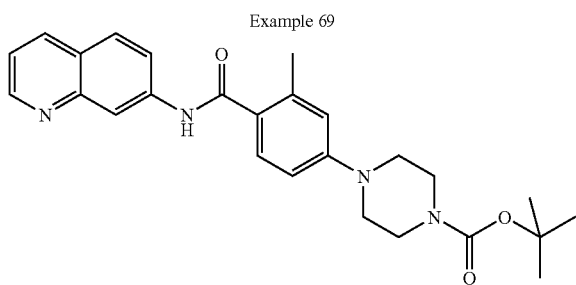
Example 70
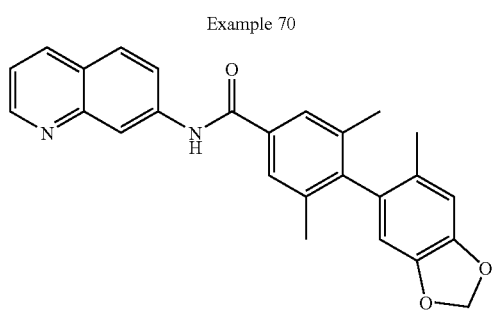
Example 71
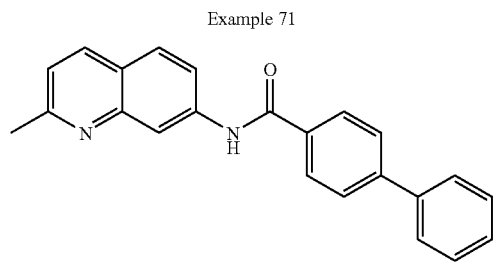
Example 72
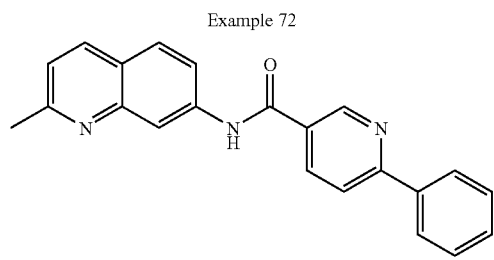
Example 73
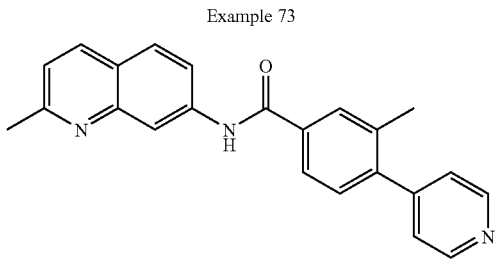
Example 74
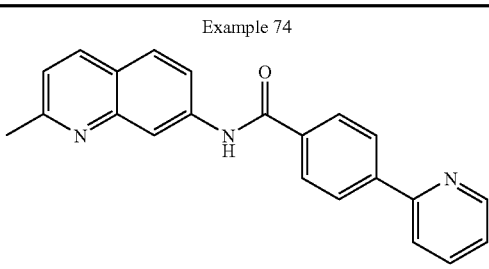
Example 75
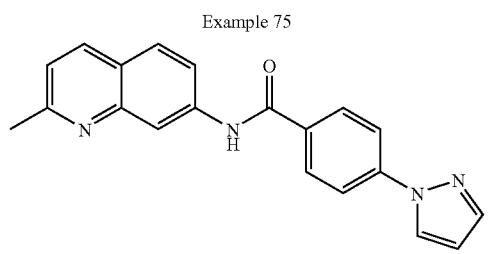
Example 76
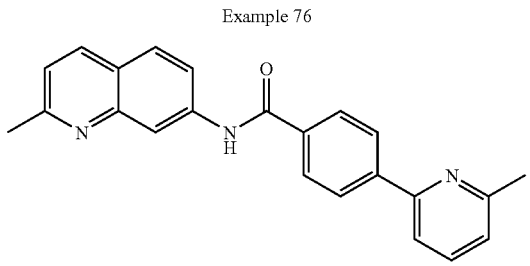
Example 77
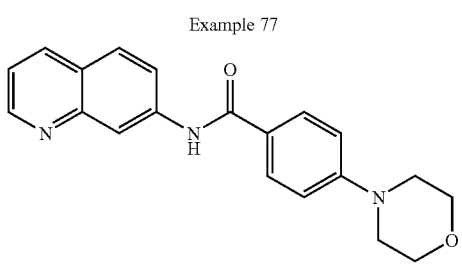
Example 78
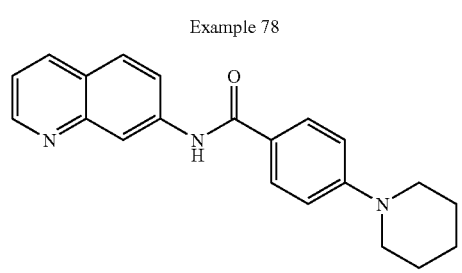
Example 79
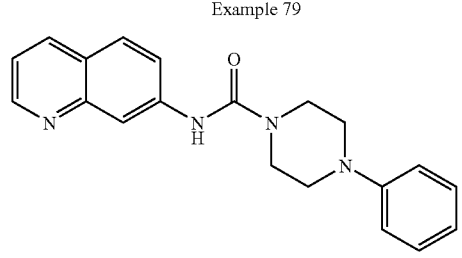

Example 80
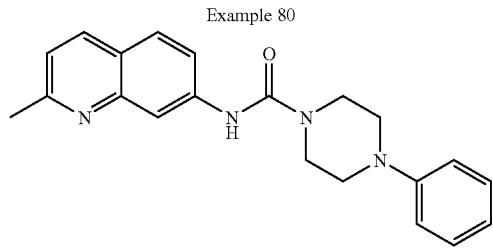
Example 81
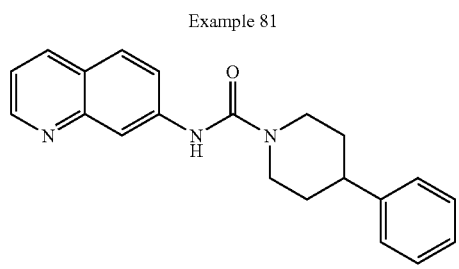
Example 82
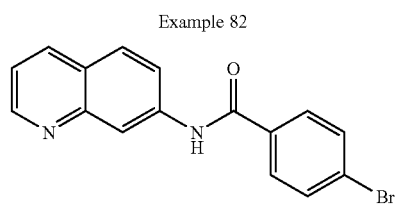
Example 83
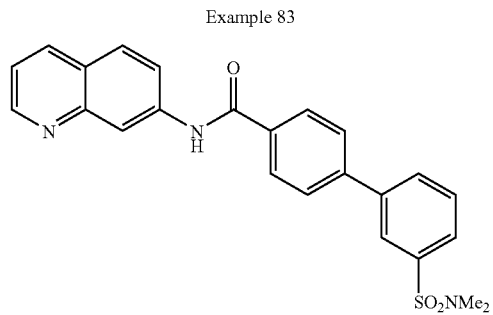
Example 84
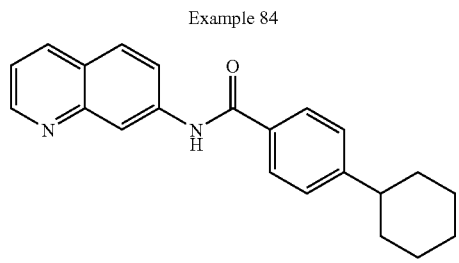
Example 85
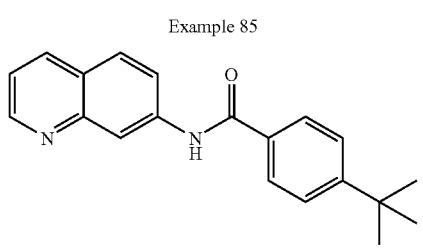
Example 86
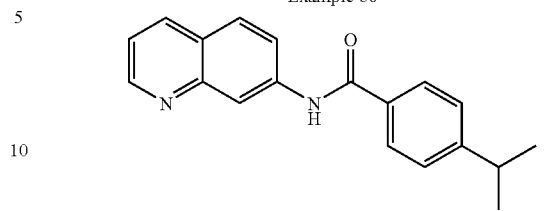
Example 87
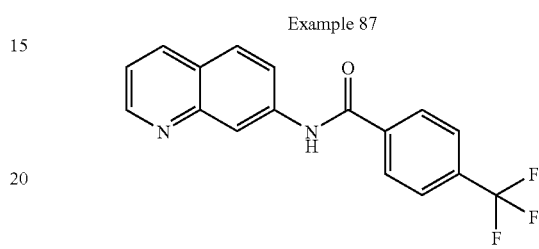
Example 88
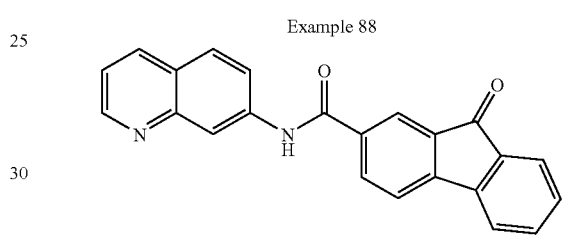
Example 89
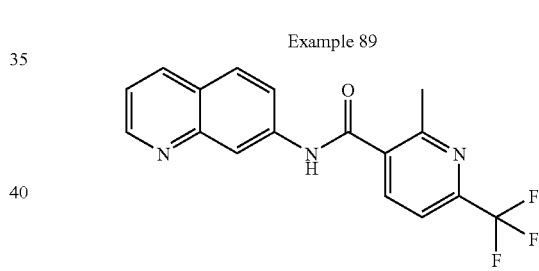
Example 90
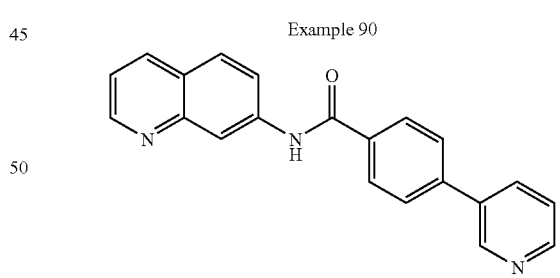
Example 91
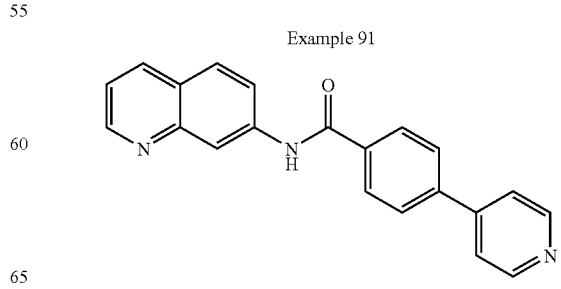

-continued
Example 92
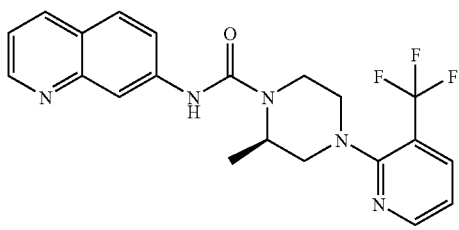
Example 93
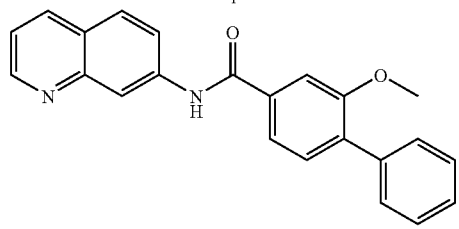
Example 94
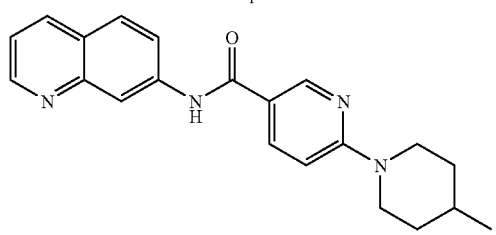
Example 95
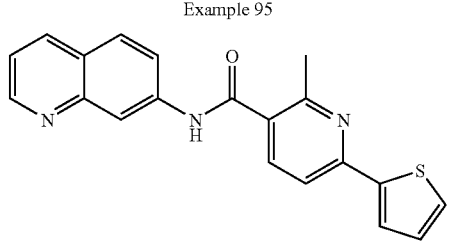
Example 96
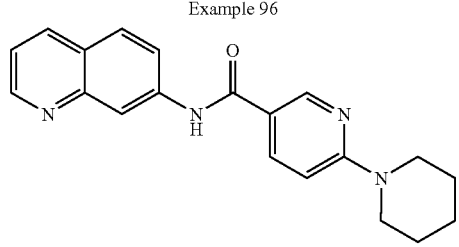
Example 97
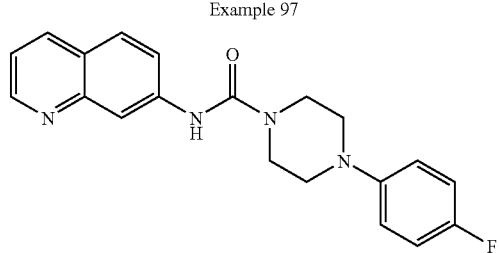
-continued
Example 98
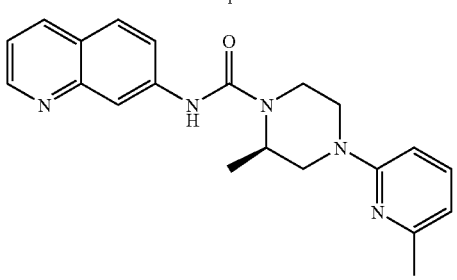
Example 99
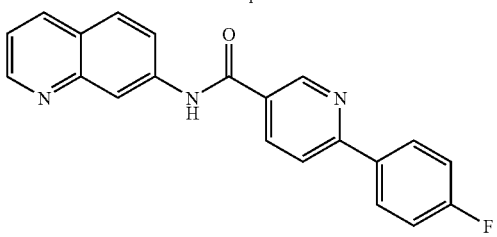
Example 100
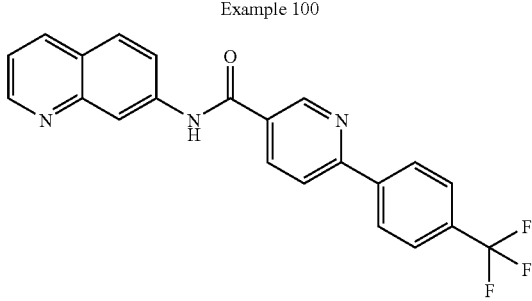
Example 101
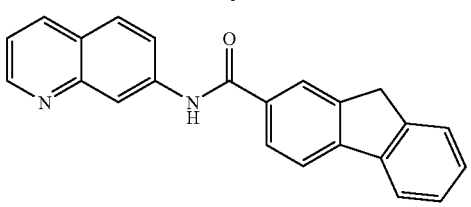
Example 102
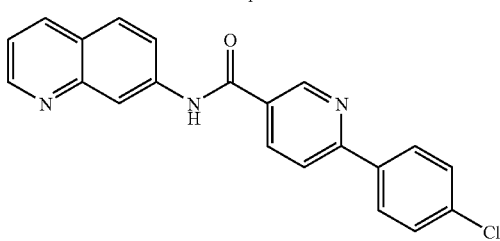

-continued
Example 103
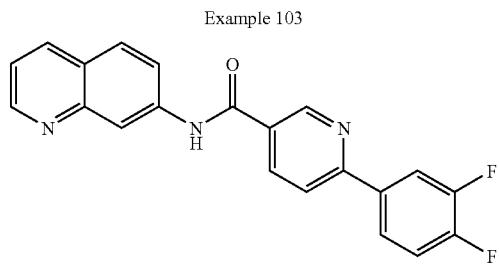
Example 104
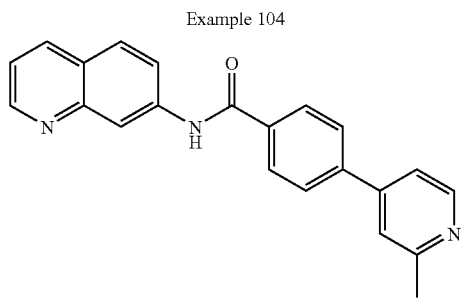
Example 105
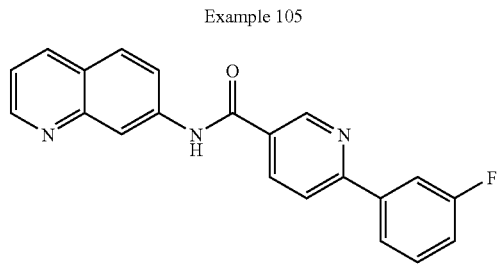
Example 106
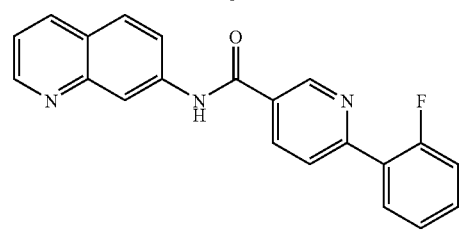
Example 107
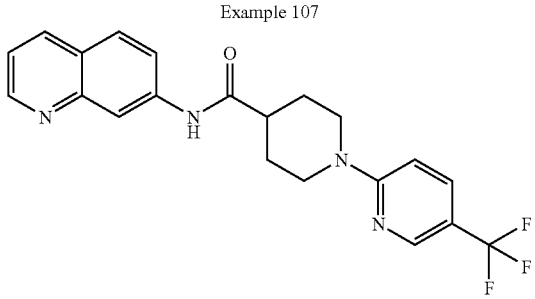
-continued
Example 108
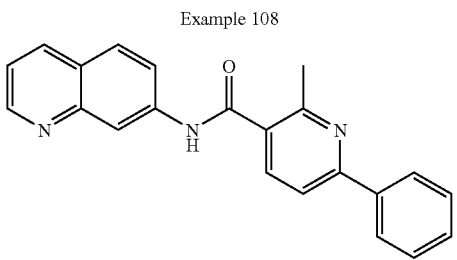
Example 109
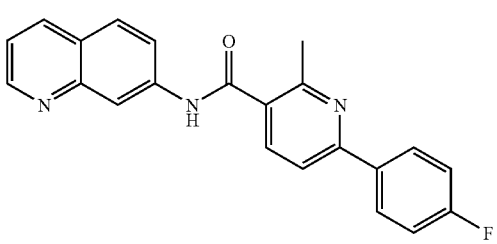
Example 110
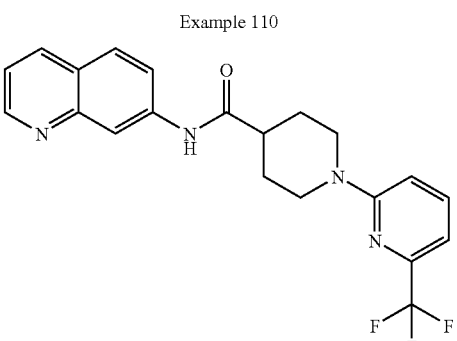
Example 111
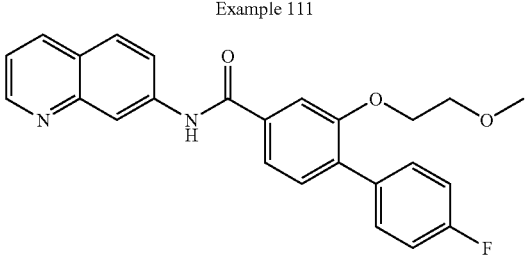
Example 112
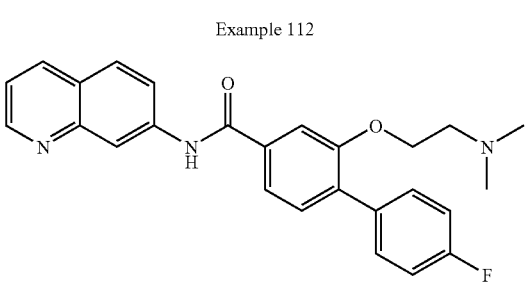

Example 113
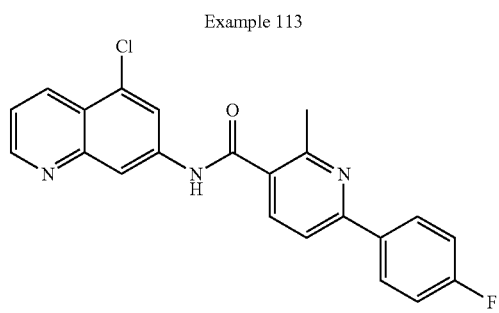
Example 114
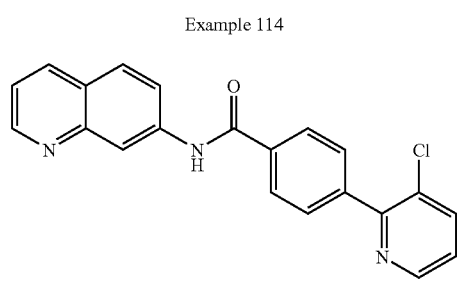
Example 115
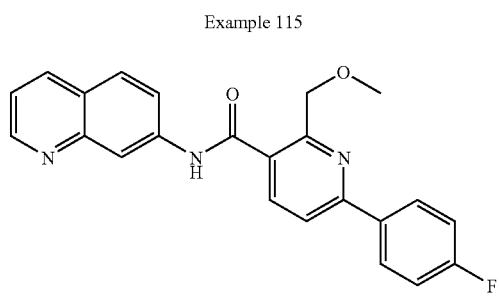
Example 116
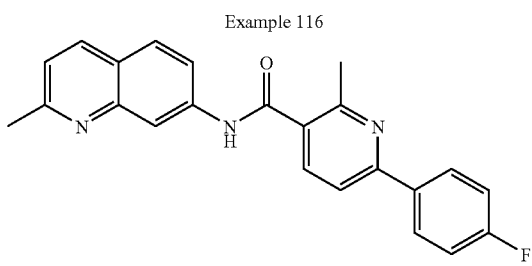
Example 117
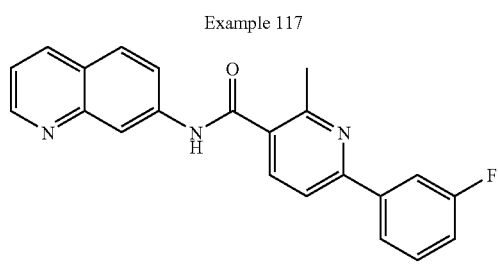
Example 118
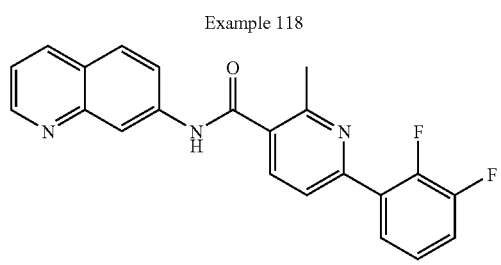
Example 119
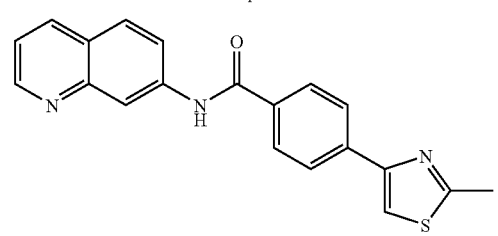
Example 120
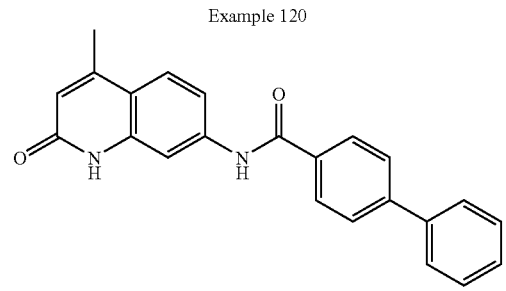
Example 121
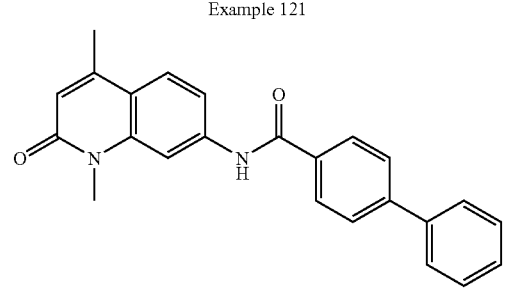
Example 122
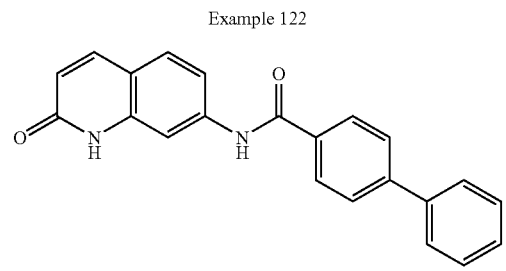

-continued

Example 123

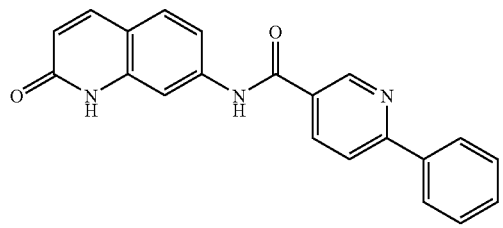

Example 124

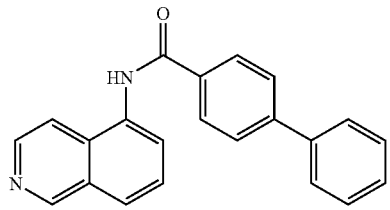

Example 125

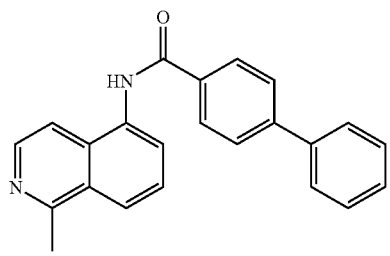

Example 126

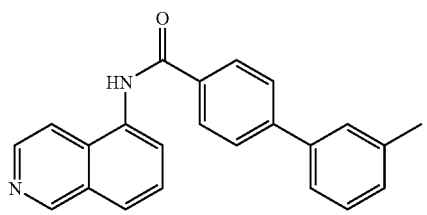

Example 127

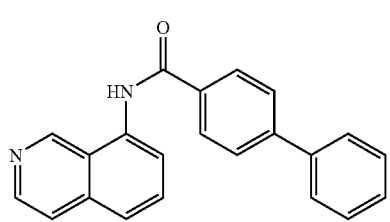

Example 128

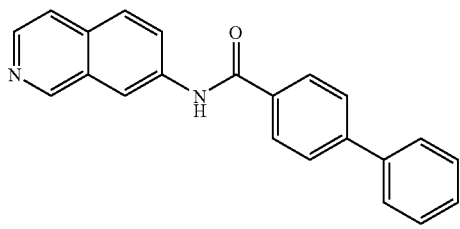

-continued

Example 129

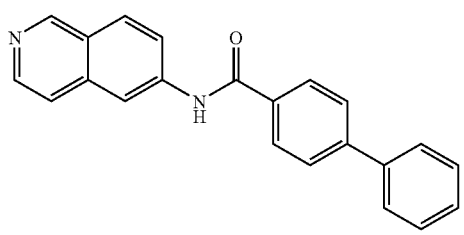

Example 130

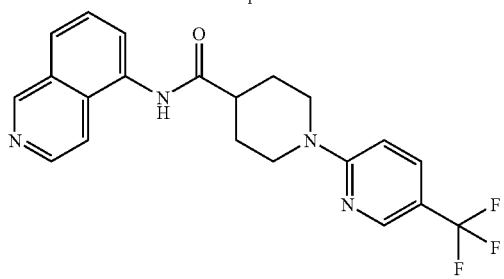

Example 131

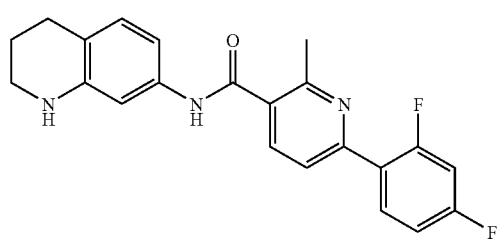

Example 132

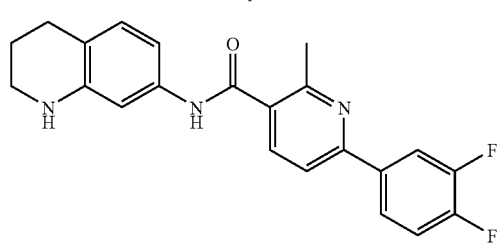

Example 133

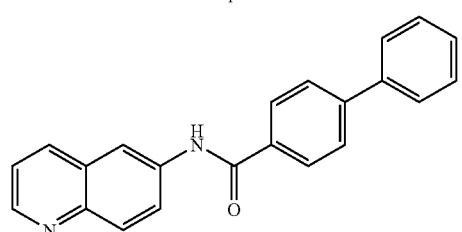

Certain of the carbon atoms of formula (I) are chiral carbon atoms, and therefore compounds of formula (I) may exist as stereoisomers. The invention extends to all optical isomers such as stereoisomeric forms of the compounds of formula (I) including enantiomers and mixtures thereof, such as racemates. The different stereoisomeric forms may be separated or resolved one from the other by conventional methods or any given isomer may be obtained by conventional stereospecific or asymmetric syntheses.

As indicated above, the compounds of formula (I) can form salts, especially pharmaceutically acceptable salts. Suitable pharmaceutically acceptable salts are those used conventionally in the art and include those described in *J. Pharm. Sci.*, 1977, 66, 1-19, such as acid addition salts.

Suitable pharmaceutically acceptable salts include acid addition salts.

Suitable pharmaceutically acceptable acid addition salts include salts with inorganic acids such, for example, as hydrochloric acid, hydrobromic acid, orthophosphoric acid or sulphuric acid, or with organic acids such, for example as methanesulphonic acid, toluenesulphonic acid, acetic acid, propionic acid, lactic acid, citric acid, fumaric acid, malic acid, succinic acid, salicylic acid, maleic acid, glycerophosphoric acid or acetylsalicylic acid.

The salts and/or solvates of the compounds of the formula (I) which are not pharmaceutically acceptable may be useful as intermediates in the preparation of pharmaceutically acceptable salts and/or solvates of compounds of formula (I) or the compounds of the formula (I) themselves, and as such form another aspect of the present invention.

The compounds of formula (I) may be prepared in crystalline or non-crystalline form, and if crystalline, may be optionally hydrated or solvated. This invention includes in its scope stoichiometric hydrates as well as compounds containing variable amounts of water.

Suitable solvates include pharmaceutically acceptable solvates, such as hydrates.

Solvates include stoichiometric solvates and non-stoichiometric solvates.

As used herein the term "alkyl" as a group or part of a group refers to a straight or branched chain saturated aliphatic hydrocarbon radical containing 1 to 12 carbon atoms, suitably 1 to 6 carbon atoms. Such alkyl groups in particular include methyl ("Me"), ethyl ("Et"), n-propyl ("Pr$^n$"), iso-propyl ("Pr$^i$"), n-butyl ("Bu$^n$"), sec-butyl ("Bu$^s$"), tert-butyl ("Bu$^t$"), pentyl and hexyl. Where appropriate, such alkyl groups may be substituted by one or more groups selected from halo (such as fluoro, chloro, bromo), —CN, —CF$_3$, —OH, —OCF$_3$, C$_{2-6}$ alkenyl, C$_{3-6}$ alkynyl, C$_{1-6}$ alkoxy, aryl and di-C$_{1-6}$ alkylamino.

As used herein, the term "alkoxy" as a group or part of a group refers to an alkyl ether radical, wherein the term "alkyl" is defined above. Such alkoxy groups in particular include methoxy, ethoxy, n-propoxy, iso-propoxy, n-butoxy, iso-butoxy, sec-butoxy and tert-butoxy. Where appropriate, such alkoxy groups may be substituted by one or more groups selected from halo (such as fluoro, chloro, bromo), —CN, —CF$_3$, —OH, —OCF$_3$, C$_{1-6}$ alkyl, C$_{2-6}$ alkenyl, C$_{3-6}$ alkynyl, aryl and di-C$_{1-6}$ alkylamino.

As used herein, the term "aryl" as a group or part of a group refers to a carbocyclic aromatic radical ("Ar"). Suitably such aryl groups are 5-6 membered monocyclic groups or 8-10 membered fused bicyclic groups, especially phenyl ("Ph"), biphenyl and naphthyl, particularly phenyl.

The term "naphthyl" is used herein to denote, unless otherwise stated, both naphth-1-yl and naphth-2-yl groups.

As used herein, the term "heteroaryl" as a group or part of a group refers to a stable 5-7-membered monocyclic or 7- to 10-membered bicyclic heterocyclic aromatic ring which consists of carbon atoms and from 1 to 4 heteroatoms independently selected from the group consisting of N, O and S. It is preferred that the total number of S and O atoms in the aromatic heterocycle is not more than 1. Examples of suitable heteroaryl groups include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolyl, carbazolyl, carbolinyl, chromanyl, chromenyl, cinnolinyl, decahydroquinolinyl, 2H, 6H-1,5,2-dithiazinyl, dihydrobenzofuranyl, furanyl, furazanyl, imidazolyl, 1H-indazolyl, indolinyl, indolyl, isobenzofuranyl, isochromanyl, isoindazolyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolyl, pyrimidinyl, phthalazinyl, pteridinyl, purinyl, pyrazinyl, pyrazolyl, pyridooxazolyl, pyridoimidazolyl, pyridothiazolyl, pyridyl, pyrrolyl, quinazolinyl, quinolinyl, quinoxalinyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thiazolyl, thienyl, thienothiazolyl, thienooxazolyl, thienoimidazolyl, triazinyl, 1,2,3-triazolyl, 1,2,4-triazolyl, 1,2,5-triazolyl, 1,3,4-triazolyl and xanthenyl.

As used herein, the terms "heterocyclyl" and "heterocyclic" as a group or part of a group refer to stable heterocyclic non-aromatic single and fused rings containing one or more heteroatoms independently selected from nitrogen, oxygen and sulfur. A fused heterocyclyl ring system may include carbocyclic rings and need include only one heterocyclic ring. Examples of suitable heterocyclyl groups include, but are not limited to, piperazinyl, homopiperazinyl, piperidinyl, pyrrolidinyl and morpholinyl.

The term "halo" is used herein to describe, unless otherwise stated, a group selected from fluorine ("fluoro"), chlorine ("chloro"), bromine ("bromo") or iodine ("iodo").

The present invention also provides a process for the preparation of a compound of formula (I) or a pharmaceutically acceptable salt or solvate thereof, which process comprises:

(a) reacting a compound of formula (II):

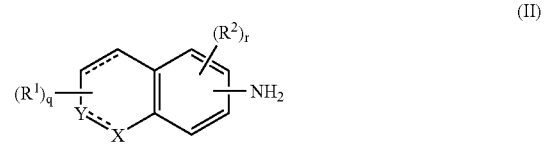

(II)

wherein, R$^1$, R$^2$, q, r, X and Y are as defined in relation to formula (I), with a compound of formula (III):

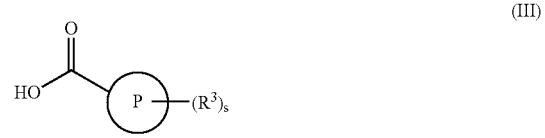

(III)

wherein, P, R$^3$ and s are as defined in relation to formula (I) and thereafter, as necessary, carrying out one or more of the following reactions:

(i) converting one compound of formula (I) into another compound of formula (I);

(ii) removing any protecting group;

(iii) preparing a salt or a solvate of the compound so formed.

The reaction between a compound of formula (II) and a compound of formula (III) may be effected using conventional methods for the formation of an amide bond, such as those described in J March, *Advanced Organic Chemistry*, 4th edition, J Wiley & Sons, 1992, p. 419-421. Typically, the reaction may be carried out in a solvent such as dichloromethane, in the presence of a suitable diimide, such as 1-(3-dimethylaminopropyl)-3-ethylcarbodiimide hydrochloride.

According to a further aspect of the present invention there is provided an alternative process for the preparation of a compound of formula (I) or a pharmaceutically acceptable salt or solvate thereof where P is phenyl or heteroaryl, which process comprises reacting a compound of formula (II) with a compound of formula (IV),

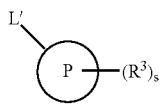
(IV)

wherein, $R^3$ and s are as defined in relation to formula (I), P is phenyl or heteroaryl and L' is selected from iodo, bromo or $-OSO_2CF_3$, in the presence of carbon monoxide and a suitable catalyst; and thereafter, as necessary, carrying out one or more of the following reactions:

(i) converting one compound of formula (I) into another compound of formula (I);

(ii) removing any protecting group;

(iii) preparing a salt or a solvate of the compound so formed.

A suitable catalyst is trans-bis-triphenylphosphinepalladium(II)bromide.

According to still a further aspect of the present invention there is provided an alternative process for the preparation of a compound of formula (I) where P is heterocyclyl, or a pharmaceutically acceptable salt or solvate thereof, which process comprises reacting a compound of formula (II) with a compound of formula (V):

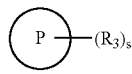
(V)

wherein, P is heterocyclyl and $R^3$ and s are as defined in relation to formula (I); and thereafter, as necessary, carrying out one or more of the following reactions:

(i) converting one compound of formula (I) into another compound of formula (I);

(ii) removing any protecting group;

(iii) preparing a salt or a solvate of the compound so formed.

The reaction between a compound of formula (II) and a compound of formula (V) may be effected using conventional methods for the formation of a urea derivative, for example, by treatment of a compound of formula (II) with a suitable activating reagent, such as phosgene, di-tertbutyl tricarbonate, or phenylchloroformate and a suitable base, followed by treatment with a compound of formula (V). The reaction may be carried out in a suitable solvent such as dichloromethane. A suitable base is triethylamine.

According to still a further aspect of the present invention, there is provided an alternative process for the preparation of compounds of formula (I), which process comprises reacting a compound of formula (VI),

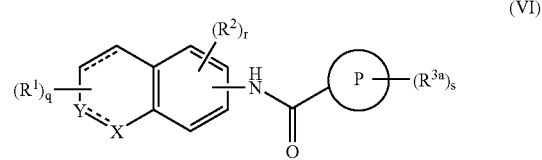
(VI)

wherein $R^1$, $R^2$, q, r, X and Y are as defined in relation to formula (I), and one $R^{3a}$ represents a group W wherein W is a halogen atom or a trifluoromethylsulfonyloxy group, or W is a group M selected from a boron derivative, for example, a boronic acid function $B(OH)_2$ or a metal function such as trialkyl stannyl, for example $SnBu_3$, zinc halide or magnesium halide; and when s is 2 the other $R^{3a}$ is $R^3$; with a compound of formula (VII),

(VII)

wherein, $R^3$ is as defined in relation to formula (I) and $W^1$ is a halogen atom or a trifluoromethylsulfonyloxy group when W is a group M or $W^1$ is a group M when W is a halogen atom or a trifluoromethylsulfonyloxy group; and thereafter, as necessary, carrying out one or more of the following reactions:

(i) converting one compound of formula (I) into another compound of formula (I);

(ii) removing any protecting group;

(iii) preparing a salt or a solvate of the compound so formed.

The reaction of a compound of formula (VI) with a compound of formula (VII) may be effected in the presence of a transition metal catalyst such as tetrakis-triphenylphosphine-palladium (0). When M represents a boronic acid function such as $B(OH)_2$, the reaction may be carried out under basic conditions, for example using aqueous sodium carbonate in a suitable solvent such as dioxane. When M is trialkylstannyl, the reaction may be carried out in an inert solvent, such as xylene or dioxane optionally in the presence of LiCl. When M is a zinc or magnesium halide, the reaction may be effected in an aprotic solvent such as tetrahydrofuran. The substituent W is preferably a halogen atom such as bromine, or a sulfonyloxy group such as trifluoromethylsulfonyloxy; and $W^1$ is preferably a group M, such as trialkylstannyl or $B(OH)_2$.

Compounds of formula (II) may be prepared by the reaction of a compound of formula (VIII),

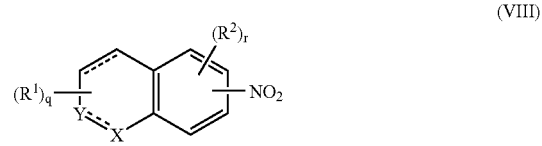
(VIII)

wherein, $R^1$, $R^2$, q and r are as defined in relation to formula (I), with a suitable reducing agent.

The reaction of a compound of formula (VIII) with a reducing agent may be effected by methods well known in the art, such as those described in J March, *Advanced Organic Chemistry*, 4th edition, J Wiley & Sons, 1992, p. 1216-1218. Suitable reducing agents include (a) iron or zinc metal in hydrochloric acid, or (b) hydrogen in the presence of a suitable catalyst, such as, 5% palladium on charcoal. Reduction using hydrogen may conveniently be performed in a solvent such as methanol or ethanol.

Compounds of formula (VIII) where X is $NR^8$ where $R^8$ is H and Y is $C(R^9)_2$, may be prepared by reaction of a compound of formula (IX),

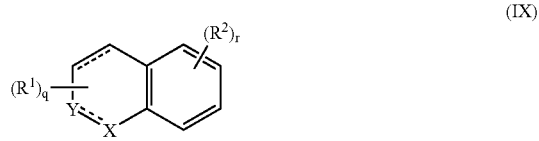

(IX)

wherein, $R^1$, $R^2$, q and r are as defined in relation to formula (I), X is $NR^8$ where $R^8$ is H and Y is $C(R^9)_2$, with concentrated sulfuric acid and concentrated nitric acid. The reaction of a compound of formula (IX) with concentrated sulfuric acid and concentrated nitric acid may be effected by methods well known in the art, such as those described in J March, Advanced Organic Chemistry, 4th edition, J Wiley & Sons, 1992, p. 522-525.

Compounds of formula (VIII) where X is N and Y is $CR^9$ may be prepared by reaction of a compound of formula (VIII) where X is $NR^8$ where $R^8$ is H and Y is $C(R^9)_2$ with (a) a suitable aromatisation reagent, such as a suitable quinone, for example, 2,3-dichloro-5,6-dicyano-1,4-benzoquinone; or (b) a suitable hydrogenation catalyst, for example, 10% Pd on charcoal, in the presence of a suitable solvent such as xylene. The reaction of a compound of formula (VIII) where X is $NR^8$ where $R^8$ is H and Y is $CH_2$ with a suitable aromatisation reagent or a suitable hydrogenation catalyst may be effected by methods well known in the art, such as those described in J March, Advanced Organic Chemistry, 4th edition, J Wiley & Sons, 1992, p. 1162-1164.

Compounds of formula (VIII) wherein X is $NR^8$ where $R^8$ is alkyl, hydroxyalkyl, cycloalkyl, aralkyl, alkoxyalkyl, cycloalkylalkyl, heterocyclylalkyl, —$S(O)_nR^6$, —$C(O)CF_3$, —C(O)alkyl, —C(O)cycloalkyl, —C(O)aralkyl, —C(O)Ar, —$C(O)(CH_2)_nOR^6$, —$C(O)(CH_2)_nNR^4R^5$, —C(O)alkoxy, —$C(O)NR^4R^5$, —$(CH_2)_nC(O)$alkoxy, —$(CH_2)_nOC(O)R^6$, —$(CH_2)_nOR^6$, —$(CH_2)_nR^4R^5$, —$(CH_2)_nC(O)NR^4R^5$, —$(CH_2)_nN(R^4)C(O)R^6$, —$(CH_2)_nS(O)_2NR^4R^5$, —$(CH_2)_nN(R^4)S(O)_2R^6$, —$(CH_2)_nS(O)_2R^6$, —$(CH_2)_nN(R^4)S(O)_2R^6$, —$(CH_2)_nN(R^4)C(O)R^6$ or —$(CH_2)_nC(O)$alkyl and Y is $C(R^9)_2$ where $R^9$ is as defined in relation to formula (I) may be prepared by reaction of a compound of formula (VIII) wherein X is $NR^8$ where $R^8$ is H and Y is $C(R^9)_2$ where $R^9$ is as defined in relation to formula (I), with (a) a suitable acylating agent; or (b) a suitable acylating reagent and thereafter, reacting the product so formed with a suitable reducing agent; or (c) a suitable alkylating agent.

The reaction between a compound of formula (VIII) with a suitable acylating agent may be effected by methods well known in the art, such as those described in J March, Advanced Organic Chemistry, 4th edition, J Wiley & Sons, 1992, p417. A suitable acylating agent is an acyl chloride. Typically, the acylation is performed in the presence of a suitable base, such as triethylamine, in a suitable solvent, such as, dichloromethane. The reduction of an acylated product so formed may be effected by methods well known in the art such as those described in J March, Advanced Organic Chemistry, 4th edition, J Wiley & Sons, 1992, p. 1212. A suitable reducing agent is borane-THF complex. Typically, the reduction is performed in a suitable solvent, such as, tetrahydrofuran.

The reaction between a compound of formula (VIII) with a suitable alkylating agent may be effected by methods well known in the art, such as those described in J March, Advanced Organic Chemistry, 4th edition, J Wiley & Sons, 1992, p411. A suitable alkylating reagent is an alkyl halide. Typically the reaction is performed in the presence of a suitable base, such as, potassium carbonate or cesium carbonate, in a suitable solvent, such as, dimethylformamide.

Compounds of formula (VIII) where Y is $NR^8$ where $R^8$ is H, and X is $C(R^9)_2$ may be prepared by methods described in International Patent Application, Publication Number WO 00/09486.

Compounds of formula (IX) are commercially available.

Compounds of formula (III) may be prepared according to a variety of known methods in accordance with the nature of the moiety, P. For example, compounds of formula (III) or their corresponding esters, where P is phenyl or heteroaryl may be prepared in accordance with methods described in J. Hassan et al., Chem. Rev., 2002, 102, 1359. Hydrolysis of the corresponding ester compounds to compounds of formula (III) may be carried out in accordance with methods disclosed in J March, Advanced Organic Chemistry, 4th edition, J Wiley & Sons, 1992, p. 378-383. Compounds of formula (III) where P is heteroaryl or heterocyclyl may be prepared in accordance with, for example, methods disclosed in the following references: H. Vorbruggen, Adv. Het. Chem., 1990, 49, 117 and E. Graf et al, Synthesis, 1999, 7, 1216.

Compounds of formula (IV) may be prepared in accordance with methods disclosed in J. Hassan et al., Chem. Rev., 2002, 102, 1359.

Compounds of formula (V) may be prepared by reaction of a compound of formula (X),

(X)

wherein $R^3$ is as defined in relation to compound of formula (I), s is 1, 2 or 3 and L" is halo, such as chloro or bromo, with a compound of formula (XI),

(XI)

wherein P is heterocyclyl.

Compounds of formula (V) where $R^3$ is heteroaryl may be prepared in accordance with the methods disclosed in H. Vorbruggen et al., Adv. Het. Chem., 1990, 49, 117. Compounds of formula (X) where $R^3$ is heteroaryl and compounds of formula (XI) are commercially available. Compounds of formula (V) where $R^3$ is phenyl are commercially available.

Compounds of formula (VI) may be prepared by analogous methods to those described herein for the preparation of compounds of formula (I).

Compounds of formula (VII) are commercially available.

The above-mentioned conversions of a compound of formula (I) into another compound of formula (I) include any conversion, which may be effected using conventional procedures, but in particular the said conversions include any combination of:

(i) converting one group $R^1$ into another group $R^1$;

(ii) converting one group $R^2$ into another group $R^2$;

(iii) converting one group $R^3$ into another group $R^3$; and (iv) converting one group $R^8$ into another group $R^8$.

The above-mentioned conversions (i), (ii), (iii) and (iv) may be performed using any appropriate method under conditions determined by the particular groups chosen.

Suitable conversions of one group $R^8$ into another group $R^8$, as in conversion (iv) above, include, (a) converting a group $R^8$ which represents —H, into another group $R^8$ which represents alkyl, such as methyl. Such a conversion may be performed using an appropriate alkylation procedure, for example, by treating a compound of formula (I) wherein $R^8$ is —H with an agent, $R^8$-Z, where $R^8$ is alkyl and Z is halo, such as bromo, chloro or iodo, or —$OSO_2CF_3$. Typically, such an interconversion is performed in the presence of a suitable base, such as, potassium carbonate or cesium carbonate. A suitable solvent is dimethylformamide;

(b) converting a group $R^8$ which represents —H, into another group $R^8$ which represents acyl, such as acetyl. Such a conversion may be performed using an appropriate acylation procedure, for example, by treating a compound of formula (I) wherein $R^8$ is —H with an agent, $R^8$-Z, where $R^8$ is acyl and Z is halo, such as chloro. Typically, such an interconversion is performed in the presence of a suitable base, such as, triethylamine. A suitable solvent is dichloromethane.

It will be appreciated by those skilled in the art that it may be necessary to protect certain reactive substituents during some of the above procedures. Standard protection and deprotection techniques, such as those described in Greene T. W. 'Protective groups in organic synthesis', New York, Wiley (1981), can be used. For example, primary amines can be protected as phthalimide, benzyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures known in the art.

Pharmaceutically acceptable salts may be prepared conventionally by reaction with the appropriate acid or acid derivative.

Compounds of formula (I) and their pharmaceutically acceptable salts and solvates thereof have Vanilloid receptor antagonist (VR1) activity and are believed to be of potential use for the treatment or prophylaxis of certain disorders, or treatment of the pain associated with them, such as: pain, chronic pain, neuropathic pain, postoperative pain, postrheumatoid arthritic pain, osteoarthritic pain, back pain, visceral pain, cancer pain, algesia, neuralgia, dental pain, headache, migraine, neuropathies, carpal tunnel syndrome, diabetic neuropathy, HIV-related neuropathy, post-herpetic neuralgia, fibromyalgia, neuritis, sciatica, nerve injury, ischaemia, neurodegeneration, stroke, post stroke pain, multiple sclerosis, respiratory diseases, asthma, cough, COPD, broncho constriction, inflammatory disorders, oesophagitis, heart burn, Barrett's metaplasia, dysphagia, gastroeosophageal relux disorder (GERD), stomach and duodenal ulcers, functional dyspepsia, irritable bowel syndrome, inflammatory bowel disease, colitis, Crohn's disease, pelvic hypersensitivity, pelvic pain, menstrual pain, renal colic, urinary incontinence, cystitis, burns, itch, psoriasis, pruritis, emesis (hereinafter referred to as the "Disorders of the Invention").

Accordingly, the invention also provides a compound of formula (I) or a pharmaceutically acceptable salt or solvate thereof, for use as an active therapeutic substance, in particular, in the treatment and/or prophylaxis of the Disorders of the Invention.

In particular, the invention provides a compound of formula (I) or a pharmaceutically acceptable salt or solvate thereof for use in the treatment or prophylaxis of pain.

The invention further provides a method for the treatment or prophylaxis of disorders in which antagonism of the Vanilloid (VR1) receptor is beneficial, in particular the Disorders of the Invention, in mammals including humans, which method comprises administering to a mammal in need thereof a therapeutically effective amount of a compound of formula (I) or a pharmaceutically acceptable salt or solvate thereof.

The invention provides for the use of a compound of formula (I) or a pharmaceutically acceptable salt or solvate thereof in the manufacture of a medicament for the treatment or prophylaxis of disorders in which antagonism of the Vanilloid (VR1) receptor is beneficial, particularly the Disorders of the Invention.

In order to use the compounds of the invention in therapy, they will normally be formulated into a pharmaceutical composition in accordance with standard pharmaceutical practice. Thus, the present invention also provides a pharmaceutical composition, which comprises a compound of formula (I) or a pharmaceutically acceptable salt or solvate thereof and a pharmaceutically acceptable carrier or excipient therefor.

A pharmaceutical composition of the invention, which may be prepared by admixture, suitably at ambient temperature and atmospheric pressure, is usually adapted for oral, parenteral, rectal administration or intravesical administration to the bladder and, as such, may be in the form of tablets, capsules, oral liquid preparations, powders, granules, lozenges, reconstitutable powders, injectable or infusable solutions, suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. For systemic administration, dosage levels from 0.01 mg to 100 mg per kilogramme of body weight are useful in the treatment of pain. However, as a general guide suitable unit doses may be 0.05 to 1000 mg, more suitably 0.05 to 20, 20 to 250, or 0.1 to 500.0 mg, for example 0.2 to 5 and 0.1 to 250 mg; and such unit doses may be administered more than once a day, for example two or three a day, so that the total daily dosage is in the range of about 0.5 to 1000 mg; and such therapy may extend for a number of weeks or months.

No unacceptable toxicological effects are indicated with compounds of the invention when administered in accordance with the invention.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of the compounds of the invention.

Abbreviations
AIBN=2,2'-azobisisobutyronitrile
BINAP=2,2'-bis(diphenylphosphino)-1,1'-binaphthyl
$CDCl_3$=chloroform-d
DCM=Dichloromethane
DME=1,2-Dimethoxyethane
DMF=DimethylformamideDMSO=dimethylsulfoxide
EtOAc=Ethyl acetate
MeOH=Methanol
$MgSO_4$=Magnesium sulfate
$Na_2SO_4$=Sodium Sulfate
NCS=N-chlorosuccinimide
$Pd_2(dba)_3$-tris(dibenzylideneacetone)dipalladium(0)
SPE=solid phase extraction
THF=Tetrahydrofuran
tlc=Thin Layer Chromatography
Xantphos—9,9-dimethyl-4,5-bis(diphenylphosphino)xanthene Description 1 (D1)

7-Nitro-1,2,3,4-tetrahydroquinoline

To a solution of 1,2,3,4-tetrahydroquinoline (6.5 g, 0.049 mol) in concentrated sulfuric acid (118 ml) cooled to 0° C. was added a solution of concentrated nitric acid (4.9 ml) in concentrated sulfuric acid (12 ml) dropwise over 0.3 h so as to maintain the temperature at 0-5° C. On completion of addition, the reaction mixture was poured onto crushed ice then neutralised with solid potassium carbonate. EtOAc (500 ml) was added and the mixture was filtered to remove undissolved solids then extracted with further EtOAc (4×500 ml). The combined extracts were dried over MgSO4 and concentrated in vacuo to give the crude product which was purified by flash column chromatography. Elution with 5% EtOAc/60-80° C. petroleum ether gave the title compound as an orange solid (5.46 g). $^1$H NMR (250 MHz, $CDCl_3$) δ(ppm): 7.40 (dd, 1H), 7.26 (d, 1H), 7.02 (d, 1H), 4.16 (br, 1H), 3.35 (m, 2H), 2.81 (t, 2H), 1.95 (m, 2H).

Description 2 (D2)

1-Methyl-7-nitro-1,2,3,4-tetrahydroquinoline

To a solution of 7-nitro-1,2,3,4-tetrahydroquinoline (D1) (7.03 g, 39.4 mmol) in dimethylformamide (50 ml) was added potassium carbonate (16.3 g, 118 mmol) and iodomethane (3.7 ml, 59.1 mmol) and the reaction stirred at ambient temperature overnight. The solvent was removed under reduced pressure and the residue was taken up in water (400 ml) and extracted into ether (3×200 ml). The combined ether extracts were washed with brine (100 ml), dried over $MgSO_4$ and concentrated in vacuo to give the crude product which was purified by flash column chromatography. Elution with 20-40% EtOAc/40-60° C. petroleum ether gave the title compound as an orange solid (5.35 g). $^1$H NMR (250 MHz, $CDCl_3$) δ (ppm): 7.42 (dd, 1H), 7.33 (d, 1H), 7.01 (d, 1H), 3.31 (m, 2H), 2.96 (s, 3H), 2.80 (t, 2H), 1.99 (m, 2H).

Description 3 (D3)

7-Amino-1-methyl-1,2,3,4-tetrahydroquinoline

A mixture of 1-methyl-7-nitro-1,2,3,4-tetrahydroquinoline (D2) (5.35 g, 27.9 mmol) and 10% palladium on charcoal (2 g, 54% water) in methanol (150 ml) was hydrogenated at atmospheric pressure and ambient temperature temperature for 3 d. The catalyst was filtered off and washed with further methanol. The combined filtrated and washings were concentrated in vacuo to give the crude product, which was purified by flash column chromatography. Elution with 5-10% EtOAc/DCM gave the title compound as a brown oil (2.58 g). $^1$H NMR (250 MHz, $CDCl_3$) δ(ppm): 6.73 (dd, 1H), 5.99 (m, 2H), 3.49 (br, 1H), 3.18 (m, 2H), 2.84 (s, 3H), 2.66 (t, 2H), 1.93 (m, 2H).

Description 4 (D4)

7-Nitro-1-trifluoroacetyl-1,2,3,4-tetrahydroquinoline

To solution of 7-nitro-1,2,3,4-tetrahydroquinoline (D1) (1 g, 5.6 mmol) and triethylamine (1.2 ml, 8.6 mmol) in DCM (30 ml) at 0° C. was added trifluoroacetic anhydride (0.8 ml, 5.7 mmol) and the reaction was then stirred at ambient temperature overnight. The reaction mixture was diluted with DCM (30 ml), washed with water (100 ml), dried over $MgSO_4$ and concentrated in vacuo to give the title compound as a yellow solid (1.52 g). $^1$H NMR (250 MHz, $CDCl_3$) δ(ppm): 8.64 (br, 1H), 8.04 (dd, 1H), 7.36 (d, $_1$H), 3.90 (m, 2H), 2.99 (t, 2H), 1.98 (m, 2H).

Description 5 (D5)

7-Amino-1-trifluoroacetyl-1,2,3,4-tetrahydroquinoline

A mixture of 7-nitro-1-trifluoroacetyl-1,2,3,4-tetrahydroquinoline (D4) (1.51 g, 5.5 mmol) and 10% palladium on charcoal (150 mg, 54% water) in methanol (80 ml) was hydrogenated at atmospheric pressure and ambient temperature for 24 h. The catalyst was removed by filtration and was washed with further methanol. The combined filtrated and washings were concentrated in vacuo to give the title compound as a pale orange solid (1.29 g). $^1$H NMR (250 MHz, $CDCl_3$) δ (ppm): 7.05 (br, 1H), 6.95 (d, 1H), 6.54 (dd, 1H), 3.78 (m, 2H), 3.65 (br, 2H), 2.74 (br, 2H), 2.03 (m, 2H).

Description 6 (D6)

1-(2-Methoxyacetyl)-7-nitro-1,2,3,4-tetrahydroquinoline

Using the procedure outlined in Description 4, the title compound was prepared from 7-nitro-1,2,3,4-tetrahydroquinoline (D1) (178 mg, 1 mmol) and methoxyacetyl chloride (101 ul, 1.1 mmol) as a yellow gum (212 mg). $^1$H NMR (250 MHz, CDCl$_3$) δ (ppm): 8.54 (br, 1H), 7.96 (dd, 1H), 7.30 (d, 1H), 4.25 (s, 2H), 3.81 (m, 2H), 3.48 (s, 3H), 2.88 (t, 2H), 2.04 (qn, 2H).

Description 7 (D7)

1-(2-Dimethylaminoacetyl)-7-nitro-1,2,3,4-tetrahydroquinoline

Using the procedure outlined in Description 4 followed by silica SPE chromatography eluting with 20% EtOAc/MeOH the title compound was prepared from 7-nitro-1,2,3,4-tetrahydroquinoline (D1) (178 mg, 1 mmol) and dimethylaminoacetyl chloride hydrochloride (174 mg, 1.1 mmol) as a yellow solid (103 mg). $^1$H NMR (250 MHz, CDCl$_3$) δ (ppm): 8.74 (d, 1H), 7.92 (dd, 1H), 7.28 (d, 1H), 3.87 (m, 2H), 3.25 (s, 2H), 2.87 (t, 2H), 2.35 (s, 6H), 1.95 (m, 2H).

Description 8 (D8)

1-(2-Chloroacetyl)-7-nitro-1,2,3,4-tetrahydroquinoline

Using the procedure outlined in Description 4, the title compound was prepared from 7-nitro-1,2,3,4-tetrahydroquinoline (D1) (4.41 g, 25 mmol) and chloroacetyl chloride (2.2 ml, 27.6 mmol) as a dark brown solid (5.853 g). $^1$H NMR (250 MHz, CDCl$_3$) δ (ppm): 8.49 (br, 1H), 8.00 (dd, 1H), 7.33 (d, 1H), 4.27 (s, 2H), 3.86 (m, 2H), 2.90 (t, 2H), 2.09 (m, 2H).

Description 9 (D9)

1-(2-Diisopropylaminoacetyl)-7-nitro-1,2,3,4-tetrahydroquinoline

A mixture of 1-(2-chloroacetyl)-7-nitro-1,2,3,4-tetrahydroquinoline (D8) (6.7 g, 26 mmol) and diisopropylamine (50 ml) in THF (50 ml) was heated at reflux for 5d then cooled to room temperature. Aqueous work-up yielded a crude oil which was purified by flash column chromatography. Elution with 0-5% methanol/DCM gave the title compound as a dark oil (6.56 g). $^1$H NMR (250 MHz, CDCl$_3$) δ (ppm): 8.62 (br, 1H), 7.91 (dd, 1H), 7.27 (d, 1H), 3.95 (m, 2H), 3.54 (s, 2H), 3.02 (sp, 2H), 2.87 (t, 2H), 2.02 (m, 2H), 1.02 (d, 12H).

Description 10 (D10)

1-(2-Methoxyethyl)-7-nitro-1,2,3,4-tetrahydroquinoline

To a solution of 1-(2-methoxyacetyl)-7-nitro-1,2,3,4-tetrahydroquinoline (D6) (212 mg, 0.85 mmol) in dry THF (9 ml) at 0° C. under an argon atmosphere, was added borane/THF complex (4.5 ml, 4.5 mmol). The reaction was stirred at 0° C. for 0.5 h then ambient temperature for 3 h. 2M Hydrochloric acid (3 ml) was added cautiously followed by water (10 ml). The mixture was extracted with EtOAc (2×10 ml) which was dried over MgSO$_4$ and concentrated in vacuo to give the desired product as an orange solid in quantitative yield. $^1$H NMR (250 MHz, CDCl$_3$) δ (ppm): 7.39 (m, 2H), 7.00 (m, 1H), 3.61 (dd, 2H), 3.52 (dd. 2H), 3.41 (m, 2H), 3.37 (s, 3H), 2.80 (t, 2H), 1.95 (m, 2H).

Description 11 (D11)

1-(2-Dimethylaminoethyl)-7-nitro-1,2,3,4-tetrahydroquinoline

Using the procedure outlined in Description 10, the title compound was prepared from 1-(2-dimethylaminoacetyl)-7-nitro-1,2,3,4-tetrahydroquinoline (D7) (103 mg, 0.39 mmol) as an orange solid (80 mg). $^1$H NMR (250 MHz, CDCl$_3$) δ (ppm): 7.43 (dd, 1H), 7.35 (d, 1H), 7.04 (d, $_1$H), 3.83 (m, 2H), 3.39 (m, 2H), 2.91 (m, 2H), 2.81 (t, 2H), 2.72 (s, 6H), 1.98 (m, 2H).

Description 12 (D12)

1-(2-Diisopropylaminoethyl)-7-nitro-1,2,3,4-tetrahydroquinoline

Using the procedure outlined in Description 10, the title compound was prepared from 1-(2-diisopropylaminoacetyl)-7-nitro-1,2,3,4-tetrahydroquinoline (D9) (6.56 g, 21 mmol) as an orange oil (4.85 g). $^1$H NMR (250 MHz, CDCl$_3$) δ (ppm): 7.42 (d, 1H), 7.33 (dd, 1H), 6.98 (d, 1H), 3.41 (m, 2H), 3.31 (m, 2H), 3.05 (sp, 2H), 2.78 (t, 2H), 2.62 (m, 2H), 1.92 (m, 2H), 1.04 (d, 12H).

Description 13 (D13)

7-Amino-1-(2-methoxyethyl)-1,2,3,4-tetrahydroquinoline

Using the procedure outlined in Description 5, the title compound was prepared from 1-(2-methoxyethyl)-7-nitro-1,2,3,4-tetrahydroquinoline (D10) (215 mg, 0.91 mmol) as a colourless gum, (152 mg). $^1$H NMR (250 MHz, CDCl$_3$) δ (ppm): 6.71 (m, 1H), 5.96 (m, 2H), 3.55 (t, 2H), 3.41 (t, 2H), 3.35 (s, 3H), 3.31 (m, 2H), 2.95 (br), 2.64 (t, 2H), 1.89 (m, 2H).

Description 14 (D14)

7-Amino-1-(2-dimethylaminoethyl)-1,2,3,4-tetrahydroquinoline

Using the procedure outlined in Description 5, the title compound was prepared from 1-(2-dimethylaminoethyl)-7-nitro-1,2,3,4-tetrahydroquinoline (D10) (75 mg, 0.3 mmol) as a crude yellow solid, (79 mg). $^1$H NMR (250 MHz, CDCl$_3$) δ (ppm): 6.75 (d, 1H), 6.35 (d, 1H), 6.05 (dd, 1H), 3.81 (m, 2H), 3.27 (m, 2H), 3.16 (t, 2H), 2.85 (s, 6H), 2.64 (t, 2H), 1.90 (m, 2H).

Description 15 (D15)

7-Amino-1-(2-diisopropylaminoethyl)-1,2,3,4-tetrahydroquinoline

Using the procedure outlined in Description 5, the title compound was prepared from 1-(2-diisopropylaminoethyl)-7-nitro-1,2,3,4-tetrahydroquinoline (D12) (4.70 g, 17 mmol) as a brown oil (2.85 g). $^1$H NMR (400 MHz, CDCl$_3$) δ (ppm): 6.71 (d, 1H), 5.95 (m, 2H), 3.43 (br, 2H), 3.29 (m, 2H), 3.20 (m, 2H), 3.02 (sp, 2H), 2.62 (m, 4H), 1.89 (m, 2H), 1.04 (d, 12H).

Description 16 (D16)

1-(2-Morpholin-4-ylethyl)-7-nitro-1,2,3,4-tetrahydroquinoline

To a solution of 7-nitro-1,2,3,4-tetrahydroquinoline (D1) (246 mg, 1.38 mmol) in DMF (2.7 ml) was added potassium carbonate (574 mg, 4.15 mmol) followed by a solution of 4-(2-iodoethyl)morpholine (500 mg, 2.07 mmol) in DMF (2 ml) and the reaction heated to 70° C. After cooling to ambient temperature the reaction mixture was diluted with water and extracted with EtOAc which was washed with water, dried over $MgSO_4$ and concentrated in vacuo to give the crude product which was purified by silica SPE chromatography. Elution with 80% EtOAc/petroleum ether gave the title compound as an orange gum (29 mg). $^1$H NMR (250 MHz, $CDCl_3$) δ (ppm): 7.39 (m, 2H), 7.00 (d, 1H), 3.73 (m, 4H), 3.47 (m, 2H), 3.38 (m, 2H), 2.79 (t, 2H), 2.49-2.59 (m, 6H), 1.96 (m, 2H).

Description 17 (D17)

7-Amino-1-(2-morpholin-4-ylethyl)-1,2,3,4-tetrahydroquinoline

Using the procedure outlined in Description 5, the title compound was prepared from 1-(2-morpholin-4-ylethyl)-7-nitro-1,2,3,4-tetrahydroquinoline (D16) (29 mg, 0.1 mmol) as a pink gum, which was used directly in the next step.

Description 18 (D18)

Ethyl 2-methyl-6-phenylnicotinate

The title compound was prepared according to E. Graf & R. Troschutz, Synthesis, 1999, 7, 1216.

Description 19 (D19)

Ethyl 6-(4-fluorophenyl)-2-methylnicotinate

The title compound was prepared from dimethylamino-(4-fluorophenyl)propan-1-one and ethyl 3-aminocrotonate using the general procedure outlined in D18. MS (ES): $MH^+$ 260.

Description 20 (D20)

Ethyl 6-(3-fluorophenyl)-2-methylnicotinate

The title compound was prepared from dimethylamino-(3-fluorophenyl)propan-1-one and ethyl 3-aminocrotonate using the general procedure outlined in D18. $^1$H NMR (250 MHz, $CDCl_3$) δ (ppm): 8.27 (d, 1H), 7.83 (m, 2H), 7.61 (d, 1H), 7.44 (m, 1H), 7.13 (m, 1H), 4.41 (q, 2H), 2.91 (s, 3H), 1.42 (t, 3H).

Description 21 (D21)

Ethyl 6-(2,3-difluorophenyl)-2-methylnicotinate

The title compound was prepared from dimethylamino-(2,3-difluorophenyl)-propan-1-one and ethyl 3-aminocrotonate using the general procedure outlined in D18. $^1$H NMR (250 MHz, $CDCl_3$) δ (ppm): 8.28 (d, 1H), 7.83 (m, 1H), 7.70 (dd, 1H), 7.22 (m, 2H), 4.41 (q, 2H), 2.91 (s, 3H), 1.42 (t, 3H).

Description 22 (D22)

(R)-2-Methyl-4-(3-trifluoromethyl-2-pyridyl)piperazine

The title compound was prepared according to R. Bakthavalatcham, International Patent Application, Publication Number, WO 02/08221).

Description 23 (D23)

2-Methyl-6-phenylnicotinic acid

Ethyl 2-methyl-6-phenylnicotinate (D18) (284 mg, 1.2 mmol) was treated with aq. 2M NaOH in ethanol at reflux giving the title compound as an off white solid (108 mg). MS (AP): $MH^+$ 214, $M-H^+$ 212.

Description 24 (D24)

6-(4-Fluorophenyl)-2-methylnicotinic acid

Using the procedure outlined in Description 23, the title compound was prepared from ethyl 6-(4-fluorophenyl)-2-methylnicotinate (D19) (500 mg, 1.9 mmol) as an off white solid (250 mg). $^1$H NMR (400 MHz, DMSO) δ (ppm): 8.25 (d, 1H), 8.21 (dd, 2H), 7.92 (d, 1H), 7.35(t, 2H), 2.80(s, 3H).

Description 25 (D25)

6-(3-Fluorophenyl)-2-methylnicotinic acid

Using the procedure outlined in Description 23, the title compound was prepared from ethyl 6-(3-fluorophenyl)-2-methylnicotinate (D20) (500 mg, 1.9 mmol) as an off white solid (254 mg). $^1$H NMR (250 MHz, MeOH-$d_4$) δ (ppm): 8.13 (d, 1H), 7.80 (m, 2H), 7.69 (d, 1H), 7.47 (m, 1H), 7.16 (m, 1H), 2.81 (s, 3H).

Description 26 (D26)

6-(2,3-Difluorophenyl)-2-methylnicotinic acid

Using the procedure outlined in Description 23, the title compound was prepared from ethyl 6-(2,3-difluorophenyl)-2-methylnicotinate (D21) (500 mg, 1.8 mmol) as an off white solid (344 mg). $^1$H NMR (250 MHz, $CDCl_3$) δ (ppm): 8.42(d, 1H), 7.87 (m, 1H), 7.76 (m, 1H), 7.24 (m, 2H), 2.97 (s, 3H).

Description 27 (D27)

4,4-Dimethyl-7-nitro-1-trifluoroacetyl-1,2,3,4-tetrahydroquinoline

To a suspension of 4,4-dimethyl-1,2,3,4-tetrahydroquinoline (W. W. Hoffman, A. R. Kraska, European Patent Application No. EP 0 130 795) (470 mg, 2.92 mmol) in concentrated sulfuric acid (5 ml) at 0° C. was added dropwise a mixture of concentrated nitric acid (0.3 ml) in concentrated sulfuric acid (2.8 ml) such that the temperature of the mixture remained below 5C. The reaction was allowed to warm to ambient temperature then poured onto ice, basified with 12M NaOH solution and extracted with EtOAc. The extracts were dried and concentrated in vacuo to give the crude 4,4-dimethyl-7-nitro-1,2,3,4-tetrahydroquinoline (514 mg) which was then dissolved in DCM (12 ml) and triethylamine (533 ul, 3.82 mmol) and trifluoroacetic anhydride (357 ul, 2.51 mmol) were added. The mixture was stirred at ambient temperature for 18 h then diluted with further DCM, washed with water, dried over $MgSO_4$ and concentrated in vacuo to give the crude product. Purification by column chromatography eluting with 0-30% EtOAc/40-60° C. petroleum ether gave the title compound as an orange solid (341 mg). $^1$H NMR (250 MHz, CDCl$_3$) δ (ppm): 8.62 (br, 1H), 8.06 (dd, 1H), 7.55 (d, 1H), 3.91 (m, 2H), 1.96 (m, 2H), 1.39 (s, 6H).

Description 28 (D28)

7-Amino-4,4-dimethyl-1-trifluoroacetyl-1,2,3,4-tetrahydroquinoline

Using the procedure outlined in Description 5, the title compound was prepared from 4,4-dimethyl-7-nitro-1-trifluoroacetyl-1,2,3,4-tetrahydroquinoline (D27) (282 mg, 0.93 mmol) as a green oil (237 mg). $^1$H NMR (400 MHz, DMSO) δ (ppm): 7.09 (d, 1H), 6.70-6.80 (br, 1H), 6.48 (dd, 1H), 5.08 (br, 2H), 3.70-3.80 (m, 2H), 1.70-1.80 (m, 2H), 1.20 (s, 6H). MS (ES): MH$^+$ 273.

Description 29 (D29)

4-(6-Methyl-2-pyridyl)benzoic acid

To a stirred, degassed mixture of 2-bromo-6-methylpyridine (3 g, 17 mmol), sodium carbonate (10.8 g, 100 mmol) and 4-carboxybenzeneboronic acid (2.3 g, 14 mmol) in DME (150 ml) and water (150 ml) under an argon atmosphere was added tetrakis(triphenylphosphine) palladium (0) (350 mg) and the mixture heated to reflux for 18 h. On cooling, ~50% of the solvent was removed in vacuo and the residual aqueous solution was washed with EtOAc, then acidified to pH1 with concentrated HCl and washed with further EtOAc. The aqueous was then adjusted to pH 5 by addition of potassium carbonate causing formation of a white precipitate which was collected by filtration, washed with water and dried to give the title compound as a white solid (2.3 g). MS (ES): MH$^+$ 212.

Description 30 (D30)

7-Amino-3,4-dihydro-2H-1,4-ethanoquinoline

Using the procedure outlined in Description 5, the title compound was prepared from 3,4-dihydro-2H-1,4-ethano-7-nitroquinoline (R. P. Duke et al, Tetrahedron Lett., 1970, 21, 1809) (239 mg, 0.113 mmol) as a white solid (199 mg). $^1$H NMR (400 MHz, CDCl$_3$) δ (ppm): 6.96 (d, 1H), 6.59 (d, 1H), 6.55 (dd, 1H), 3.28 (br, 2H), 3.18 (ddd, 2H), 3.02 (m, 1H), 2.70 (m, 2H), 1.81 (m, 2H), 1.52 (m, 2H).

Description 31 (D31)

N-Methyl-4'-carboxamido-1,1'-biphenyl-4-carboxylic acid

Using the procedure outlined in Description 29, the title compound was prepared from N-methyl-4-bromobenzamide (0.76 g, 3.6 mmol) and 4-carboxybenzeneboronic acid (0.56 g, 3.4 mmol) as a white solid (0.63 g). MS (API): MH$^+$ 254.

Description 32 (D32)

N,N-Dimethyl-4'-carboxamido-1,1'-biphenyl-4-carboxylic acid

Using the procedure outlined in Description 29, the title compound was prepared from N,N-dimethyl-4-bromobenzamide (2.0 g, 8.7 mmol) and 4-carboxybenzeneboronic acid (1.38 g, 8.3 mmol) as a white solid (1.46 g). MS (API): MH$^+$ 268.

Description 33 (D33)

N-Methyl-3'-sulfonamido-1,1'-biphenyl-4-carboxylic acid

Using the procedure outlined in Description 29, the title compound was prepared from N-methyl-3-bromobenzenesulfonamide (1 g, 4 mmol) and 4-carboxybenzeneboronic acid (0.56 g, 3.3 mmol) as a cream solid (0.93 g). MS (API): MH$^+$ 290.

Description 34 (D34)

2-(4-Pyridyl)furan-4-carboxylic acid

Using the procedure outlined in Description 29, the title compound was prepared from 2-bromo-furan-4-carboxylic acid (S. W. En, M. C. Yuen, H. N. C. Wong, Tetrahedron, 1996, 52(37), 12137) and 4-pyridylboronic acid.

The following acids may be prepared according to literature precedent:

Description 35 (D35)

4'-Acetylamino-2'-methyl-1,1'-biphenyl-4-carboxylic acid

L. M. Gaster, P. Ham, D. F. King and P. A. Wyman, International Patent Application, Publication Number WO 97/34901.

Description 36 (D36)

2'-Methyl-1,1'-biphenyl-4-carboxylic acid

S. I. Klein et al, J. Med. Chem., 1998, 41, 437.

Description 37 (D37)

3'-Acetyl-1,1'-biphenyl-4-carboxylic acid

G. Stemp and A. Johns, International Patent Application, Publication Number WO 97/43262.

Description 38 (D38)

3'-Carboxamido-1,1'-biphenyl-4-carboxylic acid

G. Stemp and A. Johns, International Patent Application, Publication Number WO 97/43262.

Description 39 (D39)

3-Methyl-1,1'-biphenyl-4-carboxylic acid

L. M. Gaster, International Patent Application, Publication Number WO 96/06079.

Description 40 (D40)

2-Chloro-1,1'-biphenyl-4-carboxylic acid

H. Ogawa et al, International Patent Application, Publication Number WO 9534540.

Description 41 (D41)

3-(4-Carboxyphenyl)thiophene

G. Stemp and A. Johns, International Patent Application, Publication Number WO 97/43262.

Description 42 (D42)

2-(4-Carboxyphenyl)thiophene

C. A. Axton et al, J. Chem. Soc., Perkin Trans. I, 1992, 2203.

Description 43 (D43)

4-(4-Carboxyphenyl)-1-methylpyrazole

G. Stemp and A. Johns, International Patent Application, Publication Number WO 97/43262.

Description 44 (D44)

2-(4-Carboxyphenyl)pyrazine

L. M. Gaster, H. K. Rami and P. A. Wyman, International Patent Application, Publication Number WO 98/50358.

Description 45 (D45)

1-(3-Carboxyphenyl)pyrazole

M. S. Hadley, C. N. Johnson, G. J. Macdonald, G. Stemp and A. K. K. Vong, International Patent Application, Publication Number WO 00/21951.

Description 46 (D46)

5-Phenylthiophene-2-carboxylic acid

J. K. Myers et al, International Patent Application, Publication Number WO 02/17358.

Description 47 (D47)

3-(3-Pyridyl)benzoic acid

U. Hacksell et al, J. Med. Chem., 1981, 24(12), 1475.

Description 48 (D48)

6-Phenylnicotinic acid

L. M. Gaster, H. K. Rami and P. A. Wyman, International Patent Application, Publication Number WO 98/50358.

Description 49 (D49)

6-(4-Fluorophenyl)nicotinic acid

S. A. Baumeister et al, International Patent Application, Publication Number WO 02/24636.

Description 50 (D50)

4-(1-oxo-indan-5-yl)-benzoic acid

G. Stemp and A. Johns, International Patent Application, Publication Number WO 97/43262.

Description 51 (D51)

4'-Carboxamido-4-biphenylcarboxylic acid

The title compound may be prepared from 4-carboxybenzeneboronic acid and 4-bromobenzamide using the procedure outlined in International Patent Application, Publication number WO 97/4326, for the synthesis of 3'-carboxamido-1,1'-biphenyl-4-carboxylic acid.

Description 52 (D52)

4'-Acetyl-4-biphenylcarboxylic acid

The title compound may be prepared from 4-carboxybenzeneboronic acid and 4-bromoacetophenone using the procedure outlined in International Patent Application, Publication number WO 97/4326, for the synthesis of 3'-carboxamido-1,1'-biphenyl-4-carboxylic acid.

Description 53 (D53)

3-Methyl-4-(3-pyridyl)benzoic acid

The title compound may be prepared from 4-carboxy-2-methylbenzeneboronic acid (International Patent Application, Publication number WO 97/34901) and 3-bromopyridine using the general procedure outlined in International Patent Application, Publication number WO 00/06085, for the synthesis of 4-(3-pyridyl)benzoic acid.

Description 54 (D54)

7-Nitroquinoline

To a solution of 7-nitro-1,2,3,4-tetrahydroquinoline (D1) (2.20 g, 12.3 mmol) in toluene (300 ml) was added 2,3-dichloro-5,6-dicyanobenzoquinone (5.88 g, 25.9 mmol) and the reaction was heated to 90° C. for 1.5 h. After cooling to room temperature, the suspension was filtered and the filtrate concentrated in vacuo to give the crude product which was purified by flash column chromatography. Elution with 30% EtOAc in 40-60° C. petroleum ether gave the title compound as a cream solid (1.74 g). $^1$H NMR (250 MHz, CDCl$_3$) δ (ppm): 9.08 (dd, 1H), 8.98 (d, 1H), 8.30 (dd, 2H), 7.99 (d, 1H), 7.62 (dd, 1H).

Description 55 (D55)

7-Aminoquinoline

A mixture of 7-nitroquinoline (D54) (0.65 g, 3.71 mmol) and 10% palladium on charcoal (65 mg, 54% water) in methanol (20 ml) was hydrogenated at 1 atm. and ambient temperature for until complete by tlc. The catalyst was filtered off and washed with further methanol. The combined filtrated and washings were concentrated in vacuo to give the title compound as a brown solid (0.53 g). $^1$H NMR (400 MHz, CDCl$_3$) δ (ppm): 8.75 (dd, 1H), 7.98 (dd, 1H), 7.62 (d, 1H), 7.21 (d, 1H), 7.14 (dd, 1H), 6.99 (dd, 1H), 4.07 (br, 2H).

Description 56 (D56)

4-(2,6-Dimethyl-3-pyridyl)-benzoic acid

The title compound was prepared according to L. M. Gaster, H. K. Rami and P. A. Wyman, International Patent Application, Publication Number WO 98/50358.

Description 57 (D57)

3-Methyl-4-(4-pyridyl)-benzoic acid

The title compound was prepared according to L. M. Gaster and P. A. Wyman, International Patent Application, Publication Number WO 98/50346.

Description 58 (D58)

3-Methyl-1,1'-biphenyl-4-carboxylic acid

The title compound may be prepared from 4-bromo-2-methylbenzoic acid and benzeneboronic acid using the procedure outlined in International Patent Application, Publication number WO 96/06079, for the synthesis of 2-methyl-1,1'-biphenyl-4-carboxylic acid.

Description (D59) (D59)

3-Methoxy-1,1'-biphenyl-4-carboxylic acid

The title compound may be prepared from 4-bromo-2-methoxybenzoic acid and benzeneboronic acid using the procedure outlined in International Patent Application, Publication number WO 96/06079, for the synthesis of 2-methyl-1,1'-biphenyl-4-carboxylic acid.

Description 60 (D60)

2-Methyl-1,1'-biphenyl-4-carboxylic acid

The title compound was prepared according to L. M. Gaster, International Patent Application, Publication Number WO 96/06079.

Description 61 (D61)

4-(4-Carboxyphenyl)-piperazine-1-carboxylic acid tert-butyl ester

The title compound was prepared according to M. E. Duggan et al, U.S. Pat. No. 5,854,245.

Description 62 (D62)

3,5-Dimethyl-4-(4-methyl-benzo[1,3]dioxol-5-yl)-benzoic acid

The title compound may be prepared using the procedure outlined in U.S. Pat. No. 6,323,227, for the synthesis of 4-(benzo[1,3]dioxol-5-yl)benzoic acid.

Description 63 (D63)

2-Methyl-1,2,3,4-tetrahydroquinoline

A mixture of 2-methylquinoline (584 mg, 4.1 mmol), indium powder (4.21 g, 36.7 mmol), saturated aqueous ammonium chloride solution (6.3 ml) and ethanol (21 ml) were heated at reflux for 3 days. On cooling to room temperature, water was added and the mixture was filtered through Keiselguhr. The filtrate was adjusted to pH 9 with 2M sodium hydroxide solution and extracted with DCM (×2). The extracts were dried over MgSO$_4$ and concentrated in vacuo to give the crude product which was purified by flash column chromatography. Elution with 10% EtOAc in 60-80C petroleum ether gave the title compound as a pale yellow oil (383 mg). $^1$H NMR (400 MHz, CDCl$_3$) δ (ppm): 6.96 (m, 2H), 6.60 (t, 1H), 6.47 (d, 1H), 3.68 (br, 1H), 3.40 (m, 1H), 2.84 (ddd, $_1$H), 2.72 (ddd, 1H), 1.92 (m, 1H), 1.60 (m, 1H), 1.21 (d, 3H).

Description 64 (D64)

2-Methyl-7-nitro-1,2,3,4-tetrahydroquinoline

To a solution of 2-methyl-1,2,3,4-tetrahydroquinoline (D63) (383 mg, 2.6 mmol) in concentrated sulfuric acid (7.2 ml) at 0-5° C. was added concentrated nitric acid (0.26 ml) dropwise so as to maintain the temperature at 0-5° C. On completion of addition, the mixture was warmed to room temperature, stirred for 45 mins. then poured onto crushed ice and neutralised with 2M sodium hydroxide solution. The mixture was extracted with DCM which was washed with brine, dried over MgSO$_4$ and concentrated in vacuo to give the crude product which was purified by flash column chromatography. Elution with 10% EtOAc in 60-80° C. petroleum ether gave the title compound as an orange solid (297 mg). $^1$H NMR (400 MHz, CDCl$_3$) δ (ppm): 7.40 (dd, 1H), 7.27 (d, 1H), 7.03 (d, 1H), 4.01 (br, 1H), 3.46 (m, 1H), 2.87 (m, 2H), 1.92 (m, 1H), 1.59 (m, 1H), 1.24 (d, 3H).

Description 65 (D65)

7-Amino-2-methyl-1,2,3,4-tetrahydroquinoline

Using the procedure outlined in Description 55, the title compound was prepared from 2-methyl-7-nitro-1,2,3,4-tetrahydroquinoline (D64) (100 mg, 0.52 mmol) as a crude oil, (86 mg) which was used directly in the next step without further purification. $^1$H NMR (400 MHz, CDCl$_3$) δ (ppm): 6.74 (d, 1H), 6.01 (dd, 1H), 5.84 (d, 1H), 3.57 (br, 1H), 3.36 (m, 1H), 2.72 (ddd, 1H), 2.62 (ddd, 1H), 1.87 (m, 1H), 1.56 (m, 1H), 1.24 (d, 3H).

Description 66 (D66)

7-Amino-2-methylquinoline

A mixture of 7-amino-2-methyl-1,2,3,4-tetrahydroquinoline (D65) (86 mg) and wet 10% palladium/charcoal (25 mg) in xylene (20 ml) was heated at reflux for 3.5 h. After cooling to room temperature the catalyst was removed via filtration and washed with further xylene. Evaporation of the combined filtrate and washings gave the title compound as a crude off-white solid (87 mg) which was used in the next step without further purification. $^1$H NMR (400 MHz, CDCl$_3$) δ (ppm): 7.87 (d, 1H), 7.56 (d, 1H), 7.14 (d, 1H), 7.03 (d, 1H), 6.91 (dd, 1H), 4.02 (br, 2H), 2.67 (s, 3H).

Description 67 (D67)

4-(2-Pyridyl)-benzoic acid

The title compound was prepared according to N. J. Anthony et al, International Patent Application, Publication Number WO 97/36896.

Description 68 (D68)

3'-Dimethylsulfamoyl-1,1'-biphenyl-4-carboxylic acid

The title compound may be prepared from 4-carboxybenzeneboronic acid and 3-bromo-1-(dimethylsulfamoyl)benzene using the procedure outlined in International Patent Application, Publication number WO 97/4326, for the synthesis of 3'-carboxamido-1,1'-biphenyl-4-carboxylic acid.

Description 69 (D69)

4-Bromo-3-methoxy-N-quinolin-7-yl-benzamide

Using the procedure outlined in Example 56, the title compound was prepared from 7-aminoquinoline (D55) (36 mg, 0.25 mmol) and 4-bromo-3-methoxybenzoic acid (69 mg, 0.3 mmol) as a white solid (84 mg). MS(ES): MH$^+$ 357/359, M-H$^+$ 355/357.

Description 70 (D70)

6-Chloro-N-quinolin-7-yl-nicotinamide

Using the procedure outlined in Example 45, the title compound was prepared from 7-aminoquinoline (D55) (213 mg, 1.48 mmol) and 6-chloronicotinic acid (279 mg, 1.77 mmol) as a cream solid (405 mg). $^1$H NMR (250 MHz, CDCl$_3$) δ (ppm): 8.94 (m, 2H), 8.24 (m, 2H), 8.16 (d, 1H), 8.14 (br.s, 1H), 8.01 (dd, 1H), 7.87 (d, 1H), 7.51 (d, 1H), 7.39 (dd, 1H).

Description 71 (D71)

9H-Fluorene-2-carboxylic acid

The title compound was prepared according to A. Newman et al., Journal of Medicinal Chemistry, 2001, 44, 3175.

Description 72 (D72F)

4-(2-Methyl-4-pyridyl)-benzoic acid

The title compound was prepared according to L. M. Gaster, H. K. Rami and P. A. Wyman, International Patent Application, Publication Number WO 98/50358.

Description 73G (D73G)

6-(3-Fluorophenyl)nicotinic acid

The title compound may be prepared from 3-fluorophenylboronic acid using the procedure outlined in International Patent Application, Publication Number WO 02/24636, for the synthesis of 6-(4-fluorophenyl)nicotinic acid.

Description 74 (D74)

6-(2-Fluorophenyl)nicotinic acid

The title compound may be prepared from 2-fluorophenylboronic acid using the procedure outlined in International Patent Application, Publication Number WO 02/24636, for the synthesis of 6-(4-fluorophenyl)nicotinic acid.

Description 75 (D75)

Methyl 4'-fluoro-2-hydroxy-1,1'-biphenyl-4-carboxylate

Methyl 4-bromo-3-hydroxybenzoate (2.1 g, 9.0 mmol), 4-fluorophenyl-boronic acid (2.52 g, 18 mmol), tetrakis(triphenylphosphine)palladium (0.52 g, 0.45 mmol), and 2M aqueous sodium carbonate solution (11 ml) in ethanol/toluene (1:5, 30 ml) were heated at reflux overnight. After cooling the solvent was removed in vacuo and the residue dissolved in EtOAc then washed with sat. aq. sodium bicarbonate and dried over MgSO$_4$. The crude product was purified by column chromatography eluting with 1% MeOH/DCM giving the title compound as a solid (1.9 g). MS(ES): MH$^+$ 247, M-H$^+$ 245.

Description 76 (D76)

Methyl 4'-fluoro-2-(2-methoxyethoxy)-1,1'-biphenyl-4-carboxylate

To a suspension of methyl 4'-fluoro-2-hydroxy-1,1'-biphenyl-4-carboxylate (D75) (400 mg, 1.6 mmol) in DMF (10 ml) was added cesium carbonate (1.27 g, 3.9 mmol) and 2-methoxyethylbromide (400 mg, 1.6 mmol) and the reaction was heated at 80° C. overnight. The solvent was evaporated and the residue was dissolved in EtOAc, washed with water and brine, then dried over MgSO$_4$ to give the title compound (494 mg) which was used without further purification in the next step. MS(ES): (M-MeOH)H$^+$ 273.

Description 77 (D77)

4'-Fluoro-2-(2-methoxyethoxy)-1,1'-biphenyl-4-carboxylic acid

Methyl 4'-fluoro-2-(2-methoxyethoxy)-1,1'-biphenyl-4-carboxylate (D76) (494 mg) was treated with aq. 2M sodium hydroxide solution (2 ml) in ethanol (3 ml) at 90° C. overnight. After cooling, the ethanol was evaporated off and the residue dissolved in EtOAc and extracted with sat. aq. sodium bicarbonate solution. This was acidified to pH3 with 2M HCl and extracted with EtOAc which was dried over MgSO$_4$ and concentrated in vacuo to give the title compound as a solid (55 mg). MS(ES): M-H$^+$ 289.

Description 78 (D78)

Methyl 2-(2-dimethylaminoethoxy)-4'-fluoro-1,1'-biphenyl-4-carboxylate

Using the procedure outlined in Description 76, the title compound was prepared from 4'-fluoro-2-hydroxy-1,1'-biphenyl-4-carboxylate (D75) (150 mg, 0.61 mmol)) and 2-(dimethylamino)ethylchloride hydrochloride (114 mg, 0.79 mmol) as a crude gum (200 mg) which was used without further purification in the next step. MS(ES): MH$^+$ 318.

Description 79 (D79)

2-(2-Dimethylaminoethoxy)-4'-fluoro-1,1'-biphenyl-4-carboxylic acid

Using the procedure outlined in Description 77, the title compound was prepared from methyl 2-(2-dimethylaminoethoxy)-4'-fluoro-1,1'-biphenyl-4-carboxylate (D78) (200 mg, 0.61 mmol)) and 2-(dimethylamino)ethylchloride hydrochloride (114 mg, 0.79 mmol) as a solid (122 mg). MS(ES): MH$^+$ 304, M-H$^+$ 302.

Description 80 (D80)

5-Iodo-7-nitro-1-trifluoroacetyl-1,2,3,4-tetrahydroquinoline

A solution of 7-nitro-1-trifluoracteyl-1,2,3,4-tetrahydroquinoline (D4) (2 g, 7.3 mmol) in conc. sulfuric acid (10 ml) was cooled to 0° C. and treated with iodine (1.11 μg, 4.4 mmol) and potassium iodate (0.625 g, 2.9 mmol). The reaction was stirred at 0° C. for 3 h then room temperature for 2 h. The reaction mixture was slowly poured into water (150 ml) at 0° C. and extracted with DCM. This was washed with aq. sodium metabisulfite and water then dried over MgSO$_4$ and concentrated in vacuo to give the crude product. Purification by column chromatography gave the title compound (420 mg). $^1$H NMR (250 MHz, CDCl$_3$) δ (ppm): 8.59 (m, 2H), 3.86 (m, 2H), 2.90 (t, 2H), 2.17 (m, 2H).

Description 81 (D81)

5-Chloro-7-nitro-1,2,3,4-tetrahydroquinoline

A solution of 5-iodo-7-nitro-1-trifluoroacetyl-1,2,3,4-tetrahydroquinoline (D53P) (1.69 g, 6.73 mmol) in DMF (25 ml) was treated with copper (I) chloride (1.66 g, 16.8 mmol)

at 130C. for 7 h. On cooling the solution was filtered and the filtrate concentrated in vacuo. The residue was dissolved in EtOAc and washed with 5M HCl, then dried over MgSO$_4$ and concentrated in vacuo. The crude product was purified by column chromatography to give a (1:1) mixture of the title compound and 5-chloro-7-nitro-1-trifluoroacetyl-1,2,3,4-tetrahydroquinoline (591 mg). This mixture was treated with potassium carbonate in methanol to yield the title compound (450 mg) as a brown solid. $^1$H NMR (400 MHz, CDCl$_3$) δ (ppm): 7.49 (d, 1H), 7.19 (d, 1H), 4.31 (br.s, 1H), 3.33 (m, 2H), 2.82 (t, 2H), 1.98 (m, 2H).

Description 82 (D82)

5-Chloro-7-nitroquinoline

Using the procedure outlined in Description 54, the title compound was prepared from 5-chloro-7-nitro-1,2,3,4-tetrahydroquinoline (D81) (60 mg, 0.28 mmol) as an off white solid (54 mg). $^1$H NMR (400 MHz, CDCl$_3$) δ (ppm): 9.14 (d, 1H), 8.96 (d, 1H), 8.67 (d, 1H), 8.45 (d, 1H), 7.72 (dd, 1H).

Description 83 (D83)

7-Amino-5-chloroquinoline

5-Chloro-7-nitroquinoline (D82) (50 mg, 0.24 mmol) was treated with tin dichloride dihydrate (216 mg, 0.96 mmol) and conc. hydrochloric acid (2 ml) in ethanol (5 ml) at 70° C. for 4 h. After cooling to room temperature and the ethanol removed in vacuo then the residue was dissolved in water and neutralised with potassium carbonate. This was then extracted with EtOAc which was dried over MgSO$_4$ and concentrated in vacuo to give the title compound as a brown solid (18 mg). $^1$H NMR (400 MHz, CDCl$_3$) δ (ppm): 8.78 (d, 1H), 8.39 (d, 1H), 7.25 (dd, 1H), 7.18 (d, 1H), 7.11 (d, 1H).

Description 84 (D84)

4-(3-Chloro-2-pyridyl)-benzoic acid

The title compound may be prepared from 4-carboxybenzeneboronic acid and 2,3-dichloropyridine using the procedure outlined in Description 29 (D29), for the synthesis of 4-(6-methyl-2-pyridyl)-benzoic acid.

Description 85 (D85)

Ethyl 6-(4-fluorophenyl)-2-(bromomethyl)nicotinate

Ethyl 6-(4-fluorophenyl)-2-methylnicotinate (82 mg, 0.32 mmol), N-bromosuccinimide (67 mg, 0.38 mmol) and AIBN (5 mg, 0.032 mmol) in carbon tetrachloride (7 ml) were irradiated (150W lamp) for 6 h then cooled to room temperature. The solid was filtered off and the filtrate concentrated and purified by SPE chromatography to give the title compound (38 mg) as a 5:1 mixture with the dibrominated product. $^1$H NMR (250 MHz, CDCl$_3$) δ (ppm): 8.32 (d, 1H), 8.11 (dd, 2H), 7.68 (d, 1H), 7.15 (t, 2H), 5.09 (s, 2H), 4.45 (q, 2H), 1.45 (t, 3H).

Description 86 (D86)

6-(4-Fluorophenyl)-2-(methoxymethyl)nicotinic acid

Ethyl 6-(4-fluorophenyl)-2-(bromomethyl)nicotinate (D85) (38 mg, 0.11 mmol) was treated with sodium methoxide (18 mg, 0.34 mmol) in methanol (1 ml) at room temperature for 1 h. 2M Sodium hydroxide solution was then added and the solution stirred for 1 h. The mixture was diluted with water and extracted with EtOAc which was dried over MgSO$_4$ and concentrated in vacuo to give the title compound as a white solid (19 mg). MS(ES): MH$^+$ 262, M-H$^+$ 260.

Description 87 (D87)

4-(2-Methylthiazol-4-yl)-benzoic acid

The title compound was prepared according to P. J. Sanfilippo et al, U.S. Pat. No. 5,342,851.

Description 88 (D88)

7-Amino-1,4-dimethyl-1H-quinolin-2-one

To a solution of 7-amino-4-methyl-1H-quinolin-2-one (87 mg, 0.5 mmol) in dry DMF (2 ml) was added sodium hydride (24 mg, 60% disp. in oil, 0.6 mmol) followed by methyl iodide (38 μl, 0.6 mmol) and the reaction stirred at room temperature for 1.5 h. After quenching with water the mixture was extracted with EtOAc and the combined extracts were dried over MgSO$_4$ and concentrated in vacuo to give the crude product. Purification by SPE column chromatography, eluting with 0-10% MeOH/EtOAc gradient gave title compound (64 mg) which was used in the next step without further purification. $^1$H NMR (250 MHz, CDCl$_3$) δ (ppm): 7.47 (d, 1H), 6.59 (m, 2H), 6.55 (d, 1H), 4.45 (br, 2H), 3.61 (s, 3H), 2.38 (s, 3H).

Description 89 (D89)

7-Amino-1H-quinolin-2-one

The title compound may be prepared from 7-nitro-1H-quinolin-2-one (M. Nasr et al, J. Med. Chem., 1988, 31(7), 1347) using the procedure outlined in Description 55 for the synthesis of 7-aminoquinoline.

Description 90 (D90)

N-(2,2-Dimethoxyethyl)-(1-phenyl)ethylamine

A solution of α-methylbenzylamine (8.37 g, 0.069 mol) and bromoacetaldehyde dimethylacetal (11.67 g, 0.069 mol) in acetonitrile (150 ml) containing potassium carbonate (12.39 g, 0.09 mol) was heated at reflux for 2 days then cooled. The resulting precipitate was filtered off and the filtrate was concentrated in vacuo to give the crude product as an oil. Chromatography on silica gel eluting with ethyl acetate afforded the title compound as an oil (10.1 g). $^1$H NMR (400 MHz, CDCl$_3$) δ(ppm): 7.31 (m, 3H), 7.23 (m, 2H), 4.43 (t, 1H), 3.75 (q, 1H), 3.35 (s, 3H), 3.31 (s, 3H), 2.63 (dd, 1H), 2.55 (dd, 1H), 1.36 (d, 3H).

Description 91 (D91)

1-Methylisoquinoline

To cooled chlorosulfonic acid (−10° C.) (16 ml) was cautiously added N-(2,2-dimethoxyethyl)-(1-phenyl)ethylamine (D90) (5 g, 0.024 mol) over a period of 2 h. The reaction was allowed to warm to ambient temperature and stirring continued for 3 d. The reaction was then poured into ice-water slurry (500 ml), basified using solid potassium carbonate followed by extraction with DCM. The organic phase was separated, dried over MgSO$_4$, filtered and concentrated in vacuo to give the crude product as an oil. Chromatography on silica gel eluting with ethyl acetate afforded the title compound as a yellow oil (1.04 g). $^1$H NMR (400 MHz, CDCl$_3$) δ (ppm):

8.40 (d, 1H), 8.13 (d, 1H), 7.81 (d, 1H), 7.68 (t, 1H), 7.60 (t, 1H), 7.51 (d, 1H), 2.97 (s, 3H).

Description 92 (D92)

1-Methyl-5-nitroisoquinoline

A solution 1-methylisoquinoline (D91) (1 g, 7 mmol) in sulfuric acid (2.5 ml) was cooled (<4° C.) and concentrated nitric acid (1 ml) was added over 10 mins. The reaction was stirred for 30 mins and then heated at 60° C. for 2 h. After cooling, the reaction mixture was poured into ice water slurry (100 ml) and basified using solid potassium carbonate followed by extraction with DCM. The organic phase was separated, dried over $MgSO_4$, filtered and concentrated in vacuo to afford the product as a white solid (1.05 g). $^1$H NMR (400 MHz, DMSO) δ (ppm): 8.69 (d, 1H), 8.59 (m, 2H), 8.11 (d, 1H), 7.88 (t, 1H), 2.99 (s, 3H).

Description 93 (D93)

1-Methyl-5-aminoisoquinoline

A solution of 1-methyl-5-nitroquinoline (D92) (1.0 g, 5.32 mmol) in methanol (40 ml) with 10% palladium on charcoal (0.15 g), was hydrogenated at atmospheric pressure for 5 h. The catalyst was removed by filtration and the filtrate concentrated in vacuo affording a solid which was resuspended in ether and filtered off to give the title compound (0.82 g). $^1$H NMR (400 MHz, $CDCl_3$) δ (ppm): 8.36 (d, 1H), 7.55 (d, 1H), 7.45 (d, 1H), 7.39 (t, 1H), 6.94 (d, 1H), 4.20 (br, 2H), 2.93 (s, 3H).

Description 94 (D94)

4-Bromo-N-isoquinolin-5-ylbenzamide

A solution of 5-aminoisoquinoline (800 mg, 5.54 mmol), 4-bromobenzoic acid (1.68 g, 8.3 mmol), (3-dimethylaminopropyl)-ethyl-carbodiimide hydrochloride (1.64 g, 8.3 mmol) and 4-dimethylaminopyridine (70 mg, 0.6 mmol) was stirred at room temperature overnight. The mixture was diluted with DCM, washed with saturated aqueous sodium bicarbonate solution and water, then dried over $MgSO_4$ and concentrated in vacuo to give the crude product. Purification by flash column chromatography eluting with an EtOAc/40-60° C. pet. ether gradient gave the title compound as a white solid (1.48 g). $^1$H NMR (400 MHz, $CDCl_3$) δ (ppm): 9.29 (br, 2H), 8.57 (d, 1H), 8.11 (d, 1H), 7.97, (d, 2H), 7.90 (d, 2H), 7.66 (m, 3H).

Description 95

8-Aminoisoquinoline

The title compound was prepared according to W. A. Denny et al, J. Med. Chem., 2002, 45(3), 740.

Description 96

7-Aminoisoquinoline

The title compound was prepared according to J. E. Macdonald et al., International Patent Application, Publication Number WO 97/06158.

Description 97

6-Aminoisoquinoline

The title compound was prepared according to J. G. Durant et al, European Patent Application, Publication Number EP266949.

Description 98

7-Amino-8-chloro-4,4-dimethyl-1-trifluoroacetyl-1,2,3,4-tetrahydroquinoline

To a stirred solution of 7-amino-4,4-dimethyl-7-1-trifluoroacetyl-1,2,3,4-tetrahydroquinoline (D28) (200 mg, 0.735 mmol) in DCM was added NCS (118 mg, 0.882 mmol), portion-wise over 15 mins. The reaction was stirred at room temperture for 18 h. After this period, solvents were evaporated in vacuo and the residue purified by column chromatography (0-10% EtOAc/40-60° C. pet. ether) to give the product as a an oil (76 mg). $^1$H NMR (400 MHz, $CDCl_3$) δ (ppm): 7.08 (d, 1H), 6.72 (d, 1H), 4.15-4.25 (m, 1H), 4.05-4.15 (m, 2H), 3.40-3.50 (m, 1H), 1.75-2.00 (m, 2H), 1.30 (d, 6H).

Description 99

(R)-2-Methyl-4-(6-methyl-2-pyridyl)piperazine

The title compound may be prepared from 2-bromo-6-methylpyridine using the procedure outlined in R. Bakthavalatcham, International Patent Application, Publication number WO 02/0822 for the synthesis of (R)-2-methyl-4-(3-trifluoromethyl-2-pyridyl)piperazine.

Description 100 (D100)

(R)-2-Methyl-4-(3-methyl-2-pyridyl)piperazine

The title compound may be prepared from 2-bromo-3-methylpyridine using the procedure outlined in R. Bakthavalatcham, International Patent Application, Publication number WO 02/0822 for the synthesis of (R)-2-methyl-4-(3-trifluoromethyl-2-pyridyl)piperazine.

Description 101 (D101)

1-(5-Trifluoromethlpyrid-2-yl)-piperidine-4-carboxylic acid

The title compound may be prepared from 2-chloro-5-trifluoromethyl-pyridine and piperidine-4-carboxylic acid using the procedure outlined in German Patent Application, Publication number DE4234295 for the synthesis of 1-(5-cyanopyrid-2-yl)-piperidine-4-carboxylic acid.

Description 102 (D102)

1-(6-Trifluoromethlpyrid-2-yl)-piperidine-4-carboxylic acid

The title compound may be prepared from 2-chloro-6-trifluoromethyl-pyridine and piperidine-4-carboxylic acid using the procedure outlined in German Patent Application, Publication number DE4234295 for the synthesis of 1-(5-cyanopyrid-2-yl)-piperidine-4-carboxylic acid.

Description 103 (D103)

5-Chloro-7-nitro-1-trifluoroacetyl-1,2,3,4-tetrahydroquinoline

Using the procedure outlined in Description 4, the title compound was prepared from 5-chloro-7-nitro-1,2,3,4-tetrahydroquinoline (D81) (200 mg, 0.94 mmol) as an orange solid (285 mg). $^1$H NMR (400 MHz, CDCl$_3$) δ (ppm): 8.58 (br.s, 1H), 8.15 (d, 1H), 3.88 (m, 2H), 3.00 (t, 2H), 2.19 (m, 2H).

Description 104 (D104)

7-Amino-5-chloro-1-trifluoroacetyl-1,2,3,4-tetrahydroquinoline

Using the procedure outlined in Description 83, the title compound was prepared from 5-chloro-7-nitro-1-trifluoroacetyl-1,2,3,4-tetrahydroquinoline (D103) (280 mg, 0.91 mmol) as a white solid (237 mg). $^1$H NMR (400 MHz, CDCl$_3$) δ (ppm): 7.00 (br.s, 1H), 6.65 (d, 1H), 3.77 (m, 2H), 3.70 (br, 2H), 2.78 (t, 2H), 2.06 (m, 2H).

Description 105 (D105)

Ethyl 6-(2,4-difluorophenyl)-2-methylnicotinate

The title compound was prepared from dimethylamino-(2,4-difluorophenyl)-propan-1-one and ethyl 3-aminocrotonate using the general procedure outlined in D18. $^1$H NMR (250 MHz, CDCl$_3$) δ (ppm): 8.25 (d, 1H), 8.13 (dt, 1H), 7.67 (dd, 1H), 6.86-7.05 (m, 2H), 4.40 (q, 2H), 2.90 (s, 3H), 1.41 (t, 3H).

Description 106 (D106)

6-(2,4-Difluorophenyl)-2-methylnicotinic acid

Using the procedure outlined in Description 23, the title compound was prepared from ethyl 6-(2,4-difluorophenyl)-2-methylnicotinate (D105) (2.1 g, 7.6 mmol) as a yellow solid (1.4 g). $^1$H NMR (250 MHz, CDCl$_3$) δ (ppm): 8.30 (d, 1H), 8.12 (dt, 1H), 7.66 (dd, 1H), 6.86-7.05 (m, 2H), 2.91 (s, 3H).

Description 107 (D107)

Ethyl 6-(3,4-difluorophenyl)-2-methylnicotinate

The title compound was prepared from dimethylamino-(3,4-difluorophenyl)-propan-1-one and ethyl 3-aminocrotonate using the general procedure outlined in D18. $^1$H NMR (250 MHz, CDCl$_3$) δ (ppm): 8.26 (d, 1H), 7.96 (ddd, 1H), 7.79 (m, 1H), 7.57 (d, 1H), 7.20-7.31 (m, 1H), 4.40 (q, 2H), 2.90 (s, 3H), 1.42 (t, 3H).

Description 108 (D108)

6-(2,4-Difluorophenyl)-2-methylnicotinic acid

Using the procedure outlined in Description 23, the title compound was prepared from ethyl 6-(2,4-difluorophenyl)-2-methylnicotinate (D105) (5.3 g, 19.1 mmol) as a yellow solid (1.8 g). $^1$H NMR (250 MHz, CDCl$_3$) δ (ppm): 8.32 (d, 1H), 7.96 (ddd, 1H), 7.79 (m, 1H), 7.57 (d, 1H), 7.20-7.31 (m, 1H), 2.92 (s, 3H).

EXAMPLES

Example 1

N-(1-Methyl-1,2,3,4-tetrahydroquinolin-7-yl)-1,1'-biphenyl-4-carboxamide

To a solution of 7-amino-1-methyl-1,2,3,4-tetrahydroquinoline (D3) (325 mg, 2 mmol) in DCM (10 ml) was added 4-biphenylcarboxylic acid (476 mg, 2.4 mmol) and 1-(3-dimethylaminopropyl)-3-ethylcarbodiimide hydrochloride (444 mg, 2.4 mmol) and the reaction stirred at ambient temperature. After 1 h the reaction mixture was filtered to give the title compound as a white solid. The filtrate was diluted with DCM, washed with sat. aq. sodium bicarbonate solution, dried over MgSO$_4$ and concentrated in vacuo to give further crude product which was purified by silica SPE chromatography. Elution with an EtOAc/60-80° C. petroleum ether gradient gave a mixture of the title compound and the starting acid. These fractions were washed with further sat. aq. sodium bicarbonate solution, dried over MgSO$_4$ and concentrated in vacuo to give further title compound as a white solid. $^1$H NMR (400 MHz, CDCl$_3$) δ (ppm): 7.94 (d, 2H), 7.70 (m, 3H), 7.63 (d, 2H), 7.48 (t, 2H), 7.40 (t, 1H), 7.07 (d, 1H), 6.93 (d, 1H), 6.75 (dd, 1H), 3.25 (m, 2H), 2.94 (s, 3H), 2.76 (t, 2H), 1.98 (m, 2H).

Example 2

N-(1-Methyl-1,2,3,4-tetrahydroquinolin-7-yl)-6-phenylnicotinamide

To a solution of 6-phenylnicotinic acid (D48) (500 mg, 2.51 mmol), 1-(3-dimethylaminopropyl)-3-ethylcarbodiimide hydrochloride (963 mg, 5.03 mmol) and 1-hydroxybenzotriazole hydrate (340 mg, 2.51 mmol) in DCM (20 ml) was added a solution of 7-amino-1-methyl-1,2,3,4-tetrahydroquinoline (D3) (407 mg, 2.51 mmol) in DCM (5 ml). The reaction mixture was stirred overnight then washed with sat. aq. sodium hydrogen carbonate solution (2×20 ml) and brine (20 ml). The organics were dried over MgSO$_4$ and concentrated in vacuo to give the crude product which was purified by flash column chromatography. Elution with 10-20% EtOAc/DCM gave the title compound as a yellow solid. $^1$H NMR (250 MHz, CDCl$_3$) δ (ppm): 9.14 (d, 1H), 8.25 (dd, 1H), 8.07 (m, 2H), 7.85 (d, 1H), 7.71 (br, 1H), 7.48 (m, 3H), 7.03 (br, 1H), 6.93 (d, 1H), 6.75 (dd, 1H), 3.25 (m, 2H), 2.93 (s, 3H), 2.75 (t, 2H), 1.98 (m, 2H).

Examples 3-23

7-amino-1-methyl-1,2,3,4-tetrahydroquinoline (D3) (0.03 mmol) in DCM (0.5 ml) was reacted with the appropriate acid (D31-47, D50 & D51-53) (0.03 mmol) in DMF (0.25 ml) in the presence of hydroxybenzotriazole hydrate (0.06 mmol) and excess polymer supported 1,3-dicyclohexylcarbodiimide in 1:1 DCM/THF (0.5 ml). On completion, the resin was removed by filtration and the impurities removed by ion-exchange yielding the products given in Table 1.

TABLE 1

| Example | Name | MH+ |
|---|---|---|
| 3 | N'-Methyl-N-(1-methyl-1,2,3,4-tetrahydroquinolin-7-yl)-1,1'-biphenyl-4,4'-dicarboxamide | 400 |
| 4 | 4'-Acetamido-2'-methyl-N-(1-methyl-1,2,3,4-tetrahydroquinolin-7-yl)-1,1'-biphenyl-4-carboxamide | 414 |
| 5 | N',N'-Dimethyl-N-(1-methyl-1,2,3,4-tetrahydroquinolin-7-yl)-1,1'-biphenyl-4,4'-dicarboxamide | 414 |
| 6 | 2'-Methyl-N-(1-methyl-1,2,3,4-tetrahydroquinolin-7-yl)-1,1'-biphenyl-4-carboxamide | 357 |
| 7 | 3'-Acetyl-N-(1-methyl-1,2,3,4-tetrahydroquinolin-7-yl)-1,1'-biphenyl-4-carboxamide | 385 |
| 8 | 3'-(Methylsulfamoyl)-N-(1-methyl-1,2,3,4-tetrahydroquinolin-7-yl)-1,1'-biphenyl-4-carboxamide | 436 |
| 9 | N-(1-Methyl-1,2,3,4-tetrahydroquinolin-7-yl)-1,1'-biphenyl-4,4'-dicarboxamide | 386 |
| 10 | N-(1-Methyl-1,2,3,4-tetrahydroquinolin-7-yl)-1,1'-biphenyl-3',4-dicarboxamide | 386 |
| 11 | 4'-Acetyl-N-(1-methyl-1,2,3,4-tetrahydroquinolin-7-yl)-1,1'-biphenyl-4-carboxamide | 385 |
| 12 | 2-Methyl-N-(1-methyl-1,2,3,4-tetrahydroquinolin-7-yl)-1,1'-biphenyl-4-carboxamide | 357 |
| 13 | 3-Chloro-N-(1-methyl-1,2,3,4-tetrahydroquinolin-7-yl)-1,1'-biphenyl-4-carboxamide | 377/379 |
| 14 | N-(1-Methyl-1,2,3,4-tetrahydroquinolin-7-yl)-4-(3-thienyl)benzamide | 349 |
| 15 | N-(1-Methyl-1,2,3,4-tetrahydroquinolin-7-yl)-4-(2-thienyl)benzamide | 349 |
| 16 | 4-(1-Methyl-4-pyrazolyl)-N-(1-methyl-1,2,3,4-tetrahydroquinolin-7-yl)benzamide | 347 |
| 17 | 3-Methyl-N-(1-methyl-1,2,3,4-tetrahydroquinolin-7-yl)-4-(3-pyridyl)benzamide | 358 |
| 18 | N-(1-Methyl-1,2,3,4-tetrahydroquinolin-7-yl)-4-(2-pyrazinyl)benzamide | 345 |
| 19 | N-(1-Methyl-1,2,3,4-tetrahydroquinolin-7-yl)-3-(1-pyrazolyl)benzamide | 333 |
| 20 | N-(1-Methyl-1,2,3,4-tetrahydroquinolin-7-yl)-2-(4-pyridyl)furan-4-carboxamide | 334 |
| 21 | N-(1-Methyl-1,2,3,4-tetrahydroquinolin-7-yl)-5-phenylthiophene-2-carboxamide | 349 |
| 22 | N-(1-Methyl-1,2,3,4-tetrahydroquinolin-7-yl)-3-(3-pyridyl)benzamide | 344 |
| 23 | N-(1-Methyl-1,2,3,4-tetrahydroquinolin-7-yl)-4-(1-oxo-indan-5-yl)-benzamide | 397 |

Example 24

N-(1,2,3,4-Tetrahydroquinolin-7-yl)-1,1'-biphenyl-4-carboxamide

To a solution of 7-amino-1-trifluoroacetyl-1,2,3,4-tetrahydroquinoline (D5) (1.17 g, 4.78 mmol) in DCM (20 ml) was added 4-biphenylcarboxylic acid (1.14 g, 5.73 mmol), 1-(3-dimethylaminopropyl)-3-ethylcarbodiimide hydrochloride (1.06 g, 5.73 mmol) and 4-dimethylaminopyridine (70 mg, 0.57 mmol) and the reaction stirred at room temperature. After 3.75 h the reaction mixture was treated with 2M sodium hydroxide solution overnight. An acid/base work-up followed by flash column chromatography with an EtOAc/60-80° C. petroleum ether gradient gave the title compound as a beige solid. $^1$H NMR (250 MHz, CDCl$_3$) δ (ppm): 7.91 (d, 2H), 7.63 (m, 5H), 7.47 (t, 2H), 7.41 (t, 1H), 7.11 (d, 1H), 6.91 (d, 1H), 6.61 (dd, 1H), 3.94 (br, 1H), 3.31 (m, 2H), 2.74 (t, 2H), 1.93 (m, 2H), 1.57 (br, 2H).

Example 25

6-Phenyl-N-(1-trifluoroacetyl-1,2,3,4-tetrahydroquinolin-7-yl)nicotinamide

To a solution of 7-amino-1-trifluoroacetyl-1,2,3,4-tetrahydroquinoline (D5) (122 mg, 0.5 mmol) in DCM (2 ml) was added 6-phenylnicotinic acid (D48) (119 mg, 0.6 mmol), 1-(3-dimethylaminopropyl)-3-ethylcarbodiimide hydrochloride (111 mg, 0.6 mmol) and 4-dimethylaminopyridine (7 mg, 0.06 mmol) and the reaction stirred at ambient temperature for until complete by tlc. The mixture was then washed with 2M sodium hydroxide solution (1 ml), dried over magnesium sufate and concentrated in vacuo to give the crude product which was purified by silica SPE chromatography. Elution with 20% EtOAc/60-80° C. petroleum ether gave an off-white solid which was recrystallised from EtOAc/60-80° C. petroleum ether giving the title compound as a white solid. $^1$H NMR (250 MHz, CDCl$_3$) δ (ppm): 9.10 (d, 1H), 8.20 (m, 2H), 8.04 (m, 2H), 7.86 (br, 1H), 7.82 (dd, 1H), 7.72 (br, 1H), 7.50 (m, 3H), 7.19 (1H, d), 3.84 (m, 2H), 2.84 (m, 2H), 2.06 (m, 2H).

Example 26

N-(1,2,3,4-Tetrahydroquinolin-7-yl)-6-phenylnicotinamide

6-Phenyl-N-(1-trifluoroacetyl-1,2,3,4-tetrahydroquinolin-7-yl)nicotinamide (Example 25) (155 mg, 0.364 mmol) and potassium carbonate (252 mg, 1.82 mmol) in water (2 ml) and methanol (8 ml) was stirred at ambient temperature for 40 mins. The resulting suspension was filtered and the solid was washed with water then dried in vacuo to give the title compound as a white solid. $^1$H NMR (250 MHz, CDCl$_3$) δ (ppm): 9.11 (m, 1H), 8.22 (dd, 1H), 8.03 (m, 2H), 7.82 (d, 1H), 7.75 (br, 1H), 7.48 (m, 3H), 7.06 (d, 1H), 6.91 (d, 1H), 6.62 (dd, 1H), 3.95 (br, 1H), 3.30 (m, 2H), 2.73 (t, 2H), 1.93 (m, 2H).

Example 27

N-(1-Acetyl-1,2,3,4-tetrahydroquinolin-7-yl)-1,1'-biphenyl-4-carboxamide

To a solution of N-(1,2,3,4-tetrahydroquinolin-7-yl)-1,1'-biphenyl-4-carboxamide (Example 24) (66 mg, 0.2 mmol) in DCM (1 ml) was added triethylamine (42 ul, 0.3 mmol) followed by acetyl chloride (20.5 ul, 0.3 mmol). The reaction was stirred at ambient temperature for 15 mins then treated with polymer supported trisamine resin (31 mg, 0.1 mmol) and polymer supported isocyanate resin (20 mg, 0.04 mmol). After 5 mins the resins were removed by filtration and the filtrate was washed with 2M hydrochloric acid, dried over MgSO$_4$ and concentrated in vacuo to give the title compound as an off-white solid. $^1$H NMR (250 MHz, CDCl$_3$) δ (ppm): 7.94 (d, 2H), 7.84 (d, 1H), 7.78 (br, 1H), 7.72 (d, 2H), 7.64 (d, 2H), 7.45 (m, 4H), 7.15 (d, 1H), 3.80 (t, 2H), 2.74 (t, 2H), 2.33 (s, 3H), 1.98 (qn, 2H).

Example 28

N-(1-Methoxyacetyl-1,2,3,4-tetrahydroquinolin-7-yl)-1,1'-biphenyl-4-carboxamide

Using the procedure outlined in Example 27, the title compound was prepared from N-(1,2,3,4-tetrahydroquinolin-7-yl)-1,1'-biphenyl-4-carboxamide (Example 24) (66 mg, 0.2 mmol) and methoxyacetyl chloride (27.5 ul, 0.3 mmol) as a pale pink solid. $^1$H NMR (250 MHz, CDCl$_3$) δ (ppm): 8.09 (br, 1H), 7.97 (d, 2H), 7.80 (s, 1H), 7.71 (d, 2H), 7.64 (d, 2H), 7.45 (m, 4H), 7.16 (d, 1H), 4.31 (s, 2H), 3.79 (t, 2H), 3.46 (s, 3H), 2.74 (t, 2H), 1.98 (t, 2H).

Examples 29 & 30

N-[1-(2-Acetoxyethyl)-1,2,3,4-tetrahydroquinolin-7-yl]-1,1'-biphenyl-4-carboxamide & N-[1-(2-Acetoxyethyl)-6-bromo-1,2,3,4-tetrahydroquinolin-7-yl]-1,1'-biphenyl-4-carboxamide N-(1,2,3,4-Tetrahydroquinolin-7-yl)-1,1'-biphenyl-4-carboxamide (Example 24) (66 mg, 0.2 mmol), potassium carbonate (164 mg, 1.2 mmol) and 2-bromoethyl acetate (132 ul, 1.2 mmol) in dimethylformamide (1 ml) were heated at 800C for 20 h then 1200C for 24 h. Further 2-bromoethyl acetate (132 ul, 1.2 mmol) was added and heating was continued at 1200C for 20 h. After cooling to ambient temperature the reaction mixture was diluted with EtOAc (10 ml), filtered and concentrated in vacuo to give the crude product which was purified by silica SPE chromatography. Elution with 10% EtOAc/60-80° C. petroleum ether gave the 6-bromo-title compound (Example 30) as a yellow gum. $^1$H NMR (400 MHz, CDCl$_3$) δ (ppm): 8.38 (br, 1H), 8.01 (s, 1H), 8.00 (d, 2H), 7.73 (d, 2H), 7.64 (d, 2H), 7.48 (t, 2H), 7.40 (t, 1H), 7.10 (s, 1H), 4.34 (t, 2H), 3.62 (t, 2H), 3.36 (m, 2H), 2.72 (m, 2H), 2.06 (s, 3H), 1.93 (m, 2H). MS(ES): MH$^+$ 493/495. Elution with 15% EtOAc/60-80° C. petroleum ether gave the non-brominated title compound (Example 29) as a white solid. $^1$H NMR (400 MHz, CDCl$_3$) δ (ppm): 7.94 (d, 2H), 7.75 (br, 1H), 7.70 (d, 2H), 7.63 (d, 2H), 7.48 (t, 2H), 7.40 (t, 1H), 7.15 (d, 1H), 6.92 (d, 1H), 6.74 (dd, 1H), 4.30 (t, 2H), 3.57 (t, 2H), 3.36 (m, 2H), 2.74 (t, 2H), 2.06 (s, 3H), 1.94 (m, 2H).

Example 31

N-[1-(2-Methoxycarbonylethyl)-1,2,3,4-tetrahydroquinolin-7-yl]-1,1'-biphenyl-4-carboxamide Using the procedure outlined in Example 29, the title compound was prepared from N-(1,2,3,4-tetrahydroquinolin-7-yl)-1,1'-biphenyl-4-carboxamide (Example 24) (66 mg, 0.2 mmol) and methyl 3-bromopropionate (264 ul, 2.4 mmol) as a yellow gum. $^1$H NMR (400 MHz, CDCl$_3$) δ (ppm): 7.94 (d, 2H), 7.76 (br, 1H), 7.70 (d, 2H), 7.63 (d, 2H), 7.48 (t, 2H), 7.40 (t, 1H), 7.04 (d, 1H), 6.93 (d, 1H), 6.79 (dd, 1H), 3.69 (s, 3H), 3.65 (t, 2H), 3.31 (m, 2H), 2.72 (t, 2H), 2.67 (t, 2H), 1.93 (m, 2H).

Example 32

N-[1-(2-Hydroxyethyl)-1,2,3,4-tetrahydroquinolin-7-yl]-1,1'-biphenyl-4-carboxamide N-(1,2,3,4-Tetrahydroquinolin-7-yl)-1,1'-biphenyl-4-carboxamide (Example 24) (100 mg, 0.304 mmol), potassium carbonate (126 mg, 0.913 mmol), sodium iodide (9 mg, 0.06 mmol) and 2-bromoethanol (216 ul, 3.04 mmol) in dioxane (1 ml) were heated at 60° C. for 8 d. After cooling to ambient temperature the reaction mixture was diluted with EtOAc (10 ml), filtered and concentrated in vacuo to give the crude product which was purified on a silica SPE column. Elution with an EtOAc/60-80° C. petroleum ether gradient gave the title compound as a beige solid. $^1$H NMR (400 MHz, CDCl$_3$) δ (ppm): 7.93 (d, 2H), 7.78 (s, 1H), 7.70 (d, 2H), 7.63 (d, 2H), 7.48 (t, 2H), 7.40 (t, 1H), 7.19 (d, 1H), 6.93 (d, 1H), 6.74 (dd, 1H), 3.87 (m, 2H), 3.49 (t, 2H), 3.35 (m, 2H), 2.75 (t, 2H), 1.97 (m, 3H).

Example 33

N-[1-(2-n-Propyloxyethyl)-1,2,3,4-tetrahydroquinolin-7-yl]-1,1'-biphenyl-4-carboxamide N-(1,2,3,4-Tetrahydroquinolin-7-yl)-1,1'-biphenyl-4-carboxamide (Example 24) (66 mg, 0.2 mmol), potassium carbonate (41 mg, 0.3 mmol), potassium iodide (100 mg, 0.6 mmol) and 2-chloroethyl-n-propyl ether (38 ul, 0.3 mmol) in DMF (1 ml) were heated at 60° C. for 17 h then 100° C. for 48 h. After cooling to ambient temperature the reaction mixture was purified on a silica SPE column. Elution with 8% EtOAc/60-80° C. petroleum ether gave the title compound as a yellow solid. $^1$H NMR (250 MHz, CDCl$_3$) δ (ppm): 7.93 (d, 2H), 7.72 (br, 1H), 7.70 (d, 2H), 7.63 (d, 2H), 7.48 (t, 2H), 7.40 (t, 1H), 7.03 (d, 1H), 6.92 (d, 1H), 6.74 (dd, 1H), 3.66 (t, 2H), 3.50 (t, 2H), 3.40 (m, 4H), 2.73 (t, 2H), 1.93 (qn, 2H), 1.58 (sx, 2H), 0.91 (t, 3H).

Example 34

N-[1-(2-Methoxyethyl)-1,2,3,4-tetrahydroquinolin-7-yl]-1,1'-biphenyl-4-carboxamide To a solution of 7-amino-1-(2-methoxyethyl)-1,2,3,4-tetrahydroquinoline (D13) (72 mg, 0.35 mmol) in DCM (2.5 ml) was added 4-biphenylcarboxylic acid (104 mg, 0.53 mmol), 1-(3-dimethylaminopropyl)-3-ethylcarbodiimide hydrochloride (97 mg, 0.53 mmol) and 4-dimethylaminopyridine (6 mg, 0.05 mmol) and the reaction stirred at ambient temperature overnight. The mixture was diluted with DCM, washed with 2M sodium hydroxide solution, dried over MgSO$_4$ and concentrated in vacuo to give the crude product which was purified by silica SPE chromatography. Elution with 20% EtOAc/60-80° C. petroleum ether gave the title compound as a pale yellow solid. $^1$H NMR (250 MHz, CDCl$_3$) δ (ppm): 7.93 (d, 2H), 7.77 (br, 1H), 7.69 (d, 2H), 7.62 (d, 2H), 7.47 (t, 2H), 7.39 (t, 1H), 7.06 (d, 1H), 6.91 (d, 1H), 6.73 (dd, 1H), 3.63 (t, 2H), 3.49 (t, 2H), 3.37 (s, 3H), 3.36 (t, 2H), 2.73 (t, 2H), 1.91 (m, 2H).

Example 35

N-[1-(2-Dimethylaminoethyl)-1,2,3,4-tetrahydro-quinolin-7-yl]-4-biphenyl-carboxamide To a solution of 7-amino-1-(2-dimethylaminoethyl)-1,2,3,4-tetrahydroquinoline (D14) (38 mg, 0.152 mmol) in DCM (1 ml) was added 4-biphenylcarboxylic acid (45 mg, 0.22 mmol), 1-(3-dimethylaminopropyl)-3-ethylcarbodiimide hydrochloride (42 mg, 0.22 mmol) and 4-dimethylaminopyridine (2.8 mg, 0.022 mmol) and the reaction stirred at ambient temperature overnight. The crude reaction mixture was loaded directly onto a silica SPE column and elution with EtOAc followed by 1% triethylamine/EtOAc gave the title compound as a red gum. $^1$H NMR (250 MHz, CDCl$_3$) δ (ppm): 7.94 (d, 2H), 7.75 (br, 1H), 7.70 (d, 2H), 7.64 (d, 2H), 7.47 (t, 2H), 7.39 (t, 1H), 7.01 (d, 1H), 6.92 (d, 1H), 6.82 (dd, 1H), 3.43 (m, 2H), 3.33 (m, 2H), 2.73 (t, 2H), 2.55 (m, 2H), 2.33 (s, 6H), 1.95 (m, 2H).

Example 36

N-[1-(2-Diisopropylaminoethyl)-1,2,3,4-tetrahydro-quinolin-7-yl]-1,1'-biphenyl-4-carboxamide 7-Amino-1-(2-diisopropylaminoethyl)-1,2,3,4-tetrahydroquinoline (D15) (100 mg, 0.36 mmol), 4-biphenylcarbonyl chloride (258 mg, 1.11 mmol) and pyridine (0.5 ml, 6.2 mmol) in DCM (5 ml) were stirred at room temperatue for 4 hours. 10% Potassium carbonate solution was then added and the mixture extracted with DCM which was dried over MgSO$_4$ and concentrated in vacuo to give the crude product. Purification by flash column chromatography eluting with 0-5% methanol/DCM gave the title compound as an off-white solid. $^1$H NMR (400 MHz, CDCl$_3$) δ (ppm): 7.92 (d, 2H), 7.71 (d, 2H), 7.63 (m, 3H), 7.47 (t, 2H), 7.41 (t, 1H), 6.99 (br, 1H), 6.90 (d, 1H), 6.74 (d, 1H), 3.37 (m, 2H), 3.30 (m, 2H), 3.05 (sp, 2H), 2.72 (t, 2H), 2.66 (m, 2H), 1.93 (m, 2H), 1.05 (d, 12H).

Example 37

N-[1-(2-Morpholin-4-ylethyl)-1,2,3,4-tetrahydro-quinolin-7-yl]-1,1'-biphenyl-4-carboxamide Using the procedure outlined in Example 35, the title compound was prepared from 7-amino-1-(2-morpholin-4-yl-ethyl)-1,2,3,4-tetrahydroquinoline (D17) (0.1 mmol) and 4-biphenylcarboxylic acid (24 mg, 0.12 mmol) as a red gum. $^1$H NMR (250 MHz, CDCl$_3$) δ (ppm): 7.94 (d, 2H), 7.86 (br, 1H), 7.69 (d, 2H), 7.62 (d, 2H), 7.50 (t, 2H), 7.39 (t, 1H), 7.13 (d, 1H), 6.91 (d, 1H), 6.78 (dd, 1H), 3.75 (m, 4H), 3.46 (m, 2H), 3.33 (m, 2H), 2.80-2.40 (m, 8H), 1.92 (qn, 2H).

Example 38

6-(4-Fluorophenyl)-N-(1,2,3,4-tetrahydroquinolin-7-yl)nicotinamide

To a solution of 7-amino-1-trifluoroacetyl-1,2,3,4-tetrahydroquinoline (D5) (46 mg, 0.19 mmol) in DCM (1 ml) was added 6-(4-fluorophenyl)nicotinic acid (D49) (41 mg, 0.19 mmol), 1-(3-dimethylaminopropyl)-3-ethylcarbodiimide hydrochloride (44 mg, 0.23 mmol) and 4-dimethylaminopyridine (11 mg, 0.09 mmol) and the reaction stirred at ambient temperature overnight. The crude reaction mixture was purified on a silica SPE column eluting with 0-2% methanol/DCM to give the 1-trifluoroacetyl-intermediate. This was treated with potassium carbonate (52 mg, 0.38 mmol) in methanol (2 ml) until tlc showed complete deprotection. The reaction mixture was diluted with water and extracted with DCM which was dried over MgSO$_4$, concentrated in vacuo and purified on a silica SPE column to give the title compound as a solid. $^1$H NMR (250 MHz, CDCl$_3$) δ (ppm): 9.09 (d, 1H), 8.23 (dd, 1H), 8.06 (dd, 2H), 7.81 (d, 1H), 7.64 (br, 1H), 7.19 (t, 2H), 7.07 (br, 1H), 6.92 (d, 1H), 6.62 (dd, 1H), 3.95 (br, 1H), 3.32 (m, 2H), 2.74 (t, 2H), 1.94 (m, 2H).

Example 39

6-(4-Fluorophenyl)-2-methyl-N-(1,2,3,4-tetrahydro-quinolin-7-yl)nicotinamide

Using the procedure outlined in Example 38 the title compound was prepared from 7-amino-1-trifluoroacetyl-1,2,3,4-tetrahydroquinoline (D5) (46 mg, 0.19 mmol) and 2-methyl-6-(4-fluorophenyl)-nicotinic acid (D24) (44 mg, 0.19 mmol) as a solid. $^1$H NMR (250 MHz, CDCl$_3$) δ (ppm): 8.01 (dd, 1H), 7.81 (d, 1H), 7.56 (d, 1H), 7.29 (br, 1H), 7.16 (t, 2H), 7.08 (br, 1H), 6.91 (d, 1H), 6.57 (br, 1H), 3.96 (br, 1H), 3.31 (m, 2H), 2.74 (t, 2H), 1.94 (m, 2H).

Example 40

N-(4,4-Dimethyl-1,2,3,4-tetrahydroquinolin-7-yl)-4-(3-chloro-2-pyridyl)-piperazine-1-carboxamide To a stirred solution of 7-amino-4,4-dimethyl-1-trifluoroacetyl-1,2,3,4-tetra-hydroquinoline (D28) (75 mg, 0.373 mmol) and pyridine (33 ul, 0.410 mmol) in DCM (5 ml) was added phenylchloroformate (51 ul, 0.410 mmol). The reaction mixture was stirred for 1 h at ambient temperature before triethylamine (57 ul, 0.410 mmol) was added and then left to stir for a further 30 min. After this period, 4-(3-chloro-2-pyridyl)-piperazine (U.S. Pat. No. 4,456,604) (74 mg, 0.373 mmol) in DCM (5 ml) was added and the reaction stirred at ambient temperature for 18 h. On completion, the solvents were evaporated in vacuo and the residue purified directly by chromatography, eluting with 10-100% EtOAc/40-60° C. petroleum ether, to give N-(4,4-dimethyl-1-trifluoroacetyl-1,2,3,4-tetrahydroquinol-7-yl)-4-(3-chloro-2-pyridiyl)-piperazine-1-carboxamide as a colourless oil. $^1$H NMR (400 MHz, CDCl$_3$) δ (ppm): 8.20 (dd 1H), 7.62 (dd, 1H), 7.50-7.55 (br, 1H), 7.40-7.45 (Br, 1H), 7.30 (d, 1H), 6.89 (dd, 1H), 6.42 (br, 1H), 3.80-3.85 (m, 2H), 3.60-3.65 (m, 4H), 3.40-3.45 (m, 4H), 1.33 (s, 6H). MS (ES): MH$^+$ 496/498.

A suspension of N-(4,4-dimethyl-1-trifluoroacetyl-1,2,3,4-tetrahydroquinol-7-yl)-4-(3-chloro-2-pyridyl)-piperazine-1-carboxamide (125 mg, 0.253 mmol) and potassium carbonate (105 mg, 0.758 mmol) in methanol (5 ml) and water (5 ml) was heated at 50° C. for 3 h. After this period, the solvents were evaporated in vacuo and the residue partitioned between DCM (50 ml) and water (50 ml). The aqueous layer was re-extracted with DCM (2×50 ml) and then the combined organic layers dried (Na$_2$SO$_4$) and the solvents evaporated in vacuo to give the title compound as a white solid. $^1$H NMR (400 MHz, CDCl$_3$) δ (ppm): 8.19 (dd, 1H), 7.61 (dd, 1H), 7.07 (d, 1H), 6.87 (dd, 1H), 6.75 (d, 1H), 6.41 (dd, 1H), 6.19

(br, 1H), 3.85-3.95 (br, 1H), 3.60-3.70 (m, 4H), 3.30-3.40 (m, 4H), 3.25-3.35 (m, 2H), 1.65-1.75 (m, 2H), 1.26 (s, 6H). MS (ES): MH$^+$ 400/402.

Example 41

N-(4,4-Dimethyl-1,2,3,4-tetrahydroquinolin-7-yl)-4-(3-trifluoromethyl-2-pyridyl)-piperazine-1-carboxamide To a stirred solution of 7-amino-4,4-dimethyl-1-trifluoroacetyl-1,2,3,4-tetrahydroquinoline (D28) (50 mg, 0.233 mmol) and triethylamine (65 ul, 0.465 mmol) in DCM (2 ml) at 0° C. was added triphosgene (23 mg, 0.077 mmol). The reaction mixture was stirred for 2 min at 0° C. and then at ambient temperature for 20 min. After this period, 4-(3-trifluoromethyl-2-pyridyl)-piperazine (54 mg, 0.233 mmol) in DCM (1 ml) was added and the reaction stirred at ambient temperature for 18 h. On completion, the solvents were evaporated in vacuo and the residue purified directly by chromatography, eluting with 10-100% EtOAc/40-60° C. petroleum ether, to give N-(4,4-dimethyl-1-trifluoroacetyl-1,2,3,4-tetrahydroquinol-7-yl)-4-(3-trifluoromethyl-2-pyridiyl)-piperazine-1-carboxamide as a colourless oil. $^1$H NMR (400 MHz, CDCl$_3$) δ (ppm): 8.46 (dd 1H), 7.89 (dd, 1H), 7.50-7.455 (br-s, 1H), 7.40-7.45 (m, 1H), 7.27 (d, 1H), 7.05 (dd, 1H), 6.57 (s, 1H), 3.80-3.85 (m, 2H), 3.60-3.65 (m, 4H), 3.25-3.35 (m, 4H), 1.85-1.90 (m, 2H), 1.33 (s, 6H). MS (ES): MH$^+$ 530.

A suspension of N-(4,4-dimethyl-1-trifluoroacetyl-1,2,3,4-tetrahydroquinol-7-yl)-4-(3-trifluoromethyl-2-pyridyl)-piperazine-1-carboxamide (50 mg, 0.0955 mmol) and potassium carbonate (40 mg, 0.287 mmol) in methanol (5 ml) and water (5 ml) was heated at 60° C. for 4 h. After this period, the solvents were evaporated in vacuo and the residue partitioned between DCM (50 ml) and water (30 ml). The aqueous layer was re-extracted with DCM (3×50 ml) and then the combined organic layers dried (Na$_2$SO$_4$) and the solvents evaporated in vacuo to give the title compound as a white solid. $^1$H NMR (400 MHz, CDCl$_3$) δ (ppm): 8.45 (dd, 1H), 7.90 (dd, 1H), 7.00-7.05 (m, 2H), 6.70 (d, 1H), 6.70 (d, 1H), 6.43 (dd, 1H), 6.32 (br-s, 1H), 3.60-3.65 (br, 4H), 3.20-3.30 (m, 6H), 1.65-1.70 (m, 2H), 1.26 (s, 6H). MS (ES): MH$^+$ 434.

Example 42

N-(4,4-Dimethyl-1,2,3,4-tetrahydroquinolin-7-yl)-4-(3-methyl-2-pyridyl)-piperazine-1-carboxamide To a stirred solution of 7-amino-4,4-dimethyl-1-trifluoroacetyl-1,2,3,4-tetrahydroquinoline (D28) (75 mg, 0.276 mmol) and triethylamine (56 ul, 0.551 mmol) in DCM (3 ml) at 0° C. was added triphosgene (27 ul, 0.092 mmol). The reaction mixture was stirred for 2 min at 0° C. and then at ambient temperature for 20 min. After this period, 4-(3-methyl-2-pyridyl)-piperazine (D100) (49 mg, 0.276 mmol) in DCM (2 ml) was added and the reaction stirred at ambient temperature for 18 h. On completion, the solvents were evaporated in vacuo and the residue purified directly by chromatography, eluting with 10-100% EtOAc/40-60° C. petroleum ether, to give N-(4,4-dimethyl-1-trifluoroacetyl-1,2,3,4-tetrahydroquinol-7-yl)-4-(3-methyl-2-pyridiyl)-piperazine-1-carboxamide as a colourless oil. $^1$H NMR (400 MHz, CDCl$_3$) δ (ppm): 8.16 (dd 1H), 7.50-7.55 (br, 1H), 7.40-7.45 (m, 2H), 7.26 (d, 1H), 6.89 (dd, 1H), 6.60 (br, 1H), 3.80-3.85 (m, 2H), 3.60-3.65 (m, 4H), 3.15-3.20 (m, 4H), 1.85-1.90 (m, 2H), 1.33 (s, 6H). MS (ES): MH$^+$ 476.

A suspension of N-(4,4-dimethyl-1-trifluoroacetyl-1,2,3,4-tetrahydroquinol-7-yl)-4-(3-methyl-2-pyridyl)-piperazine-1-carboxamide (100 mg, 0.210 mmol) and potassium carbonate (87 mg, 0.631 mmol) in methanol (5 ml) and water (5 ml) was heated at 60° C. for 3 h. After this period, the solvents were evaporated in vacuo and the residue partitioned between DCM (15 ml) and water (10 ml). The aqueous layer was re-extracted with DCM (2×15 ml) and then the combined organic layers dried (Na$_2$SO$_4$) and the solvents evaporated in vacuo to give the title compound as a white solid. $^1$H NMR (400 MHz, CDCl$_3$) δ (ppm): 8.16 (dd, 1H), 7.43 (dd, 1H), 7.05 (d, 1H), 6.88 (dd, 1H), 6.75 (d, 1H), 6.44 (dd, 1H), 6.29 (br, 1H), 3.85-3.95 (br, 1H), 3.55-3.65 (m, 4H), 3.25-3.30 (m, 2H), 3.15-3.25 (m, 4H), 2.29 (s, 3H), 1.65-1.70 (m, 2H), 1.26 (s, 6H). MS (ES): MH$^+$ 380.

Example 43

N-(8-Chloro-4,4-dimethyl-1,2,3,4-tetrahydroisoquinolin-7-yl)-4-(3-chloro-2-pyridyl)-piperazine-1-carboxamide Using the procedure outlined in Example 42, the title compound was prepared from 7-amino-8-chloro-4,4-dimethyl-1-trifluoroacetyl-1,2,3,4-tetrahydroquinoline (D98) and 4-(3-chloro-2-pyridyl)-piperazine (U.S. Pat. No. 4,456,604), as a pale yellow oil. MH+ 434/436

Example 44

4-(6-Methyl-2-pyridyl)-N-(1,2,3,4-tetrahydroquinolin-7-yl)benzamide

Using the procedure outlined in Example 38 the title compound was prepared from 7-amino-1-trifluoroacetyl-1,2,3,4-tetrahydroquinoline (D5) (46 mg, 0.19 mmol) and 4-(6-methyl-2-pyridyl)benzoic acid (D29) (41 mg, 0.19 mmol) as a solid. $^1$H NMR (250 MHz, CDCl$_3$) δ (ppm): 8.10 (d, 2H), 7.93 (d, 2H), 7.67 (t, 2H), 7.57 (d, 1H), 7.15 (d, 1H), 7.11 (d, 1H), 6.92 (d, 1H), 6.62 (dd, 1H), 3.31 (m, 2H), 2.74 (t, 2H), 1.93 (m, 2H)

Example 45

6-(4-Fluorophenyl)-N-(1-methyl-1,2,3,4-tetrahydroquinolin-7-yl)-2-methyl-nicotinamide To a solution of 7-amino-1-methyl-1,2,3,4-tetrahydroquinoline (D3) (31 mg, 0.19 mmol) in DCM (1 ml) was added 6-(4-fluorophenyl)-2-methylnicotinic acid (D24) (44 mg, 0.19 mmol), 1-(3-dimethylaminopropyl)-3-ethylcarbodiimide hydrochloride (44 mg, 0.23 mmol) and 4-dimethylaminopyridine (11 mg, 0.09 mmol) and the reaction stirred at ambient temperature overnight. The crude reaction mixture was loaded directly onto a silica SPE column and eluted with 0-2% methanol/DCM to give the title compound as a solid. $^1$H NMR (400 MHz, CDCl$_3$) δ (ppm): 8.02 (dd, 2H), 7.84 (d, 1H), 7.57 (d, 1H), 7.35 (br, 1H), 7.17 (t, 2H), 7.00 (s, 1H), 6.93 (d, 1H), 6.74 (d, 1H), 3.25 (m, 2H), 2.93 (s, 3H), 2.80 (s, 3H), 2.74 (m, 2H), 1.96 (m, 2H)

Example 46

N-(3,4-Dihydro-2H-1,4-ethanoquinolin-7-yl)-6-(4-fluorophenyl)-2-methyl-nicotinamide Using the procedure outlined in Example 45 the title compound was prepared from 3,4-dihydro-2H-1,4-ethanoquinolin-7-ylamine (D30) (35 mg, 0.2 mmol) and 6-(4-fluorophenyl)-2-methylnicotinic acid (D24) (46 mg, 0.2 mmol) as a solid. MS (ES): MH$^+$ 388, MH$^-$ 386.

Example 47

(R)-2-Methyl-4-(3-trifluoromethyl-2-pyridyl)-N-(1-methyl-1,2,3,4-tetrahydro-quinolin-7-yl) piperazine-1-carboxamide To a solution of 7-amino-1-methyl-1,2,3,4-tetrahydroquinoline (D3) (300 mg, 1.85 mmol) in DCM (5 ml) was added pyridine (164 ul, 2 mmol) followed by phenyl chloroformate (255 ul, 2 mmol) and the solution stirred at ambient temperature for 50 mins. Triethylamine (516 µl 3.7 mmol) was then added followed by a solution of (R)-2-methyl-4-(3-trifluoromethyl-2-pyridyl)piperazine (D22) (454 mg, 1.85 mmol) in DCM (5 ml) and the reaction stirred at ambient temperature until complete by tlc. The reaction mixture was washed (1M HCl, brine), dried over MgSO$_4$ and concentrated in vacuo to give the crude product which was purified by flash chromatography, eluting with an EtOAc/40-60° C. petroleum ether gradient, to give the title compound as a white solid. $^1$H NMR (250 MHz, CDCl$_3$) δ (ppm): 8.47 (dd, 1H), 7.90 (dd, 1H), 7.05 (dd, 1H), 6.84 (d, 1H), 6.78 (d, 1H), 6.49 (dd, 1H), 6.25 (br, 1H), 4.34 (m, 1H), 3.86 (m, 1H), 3.17-3.62 (m, 6H), 3.05 (m, 1H), 2.89 (s, 3H), 2.70.(t, 2H), 1.96 (m, 2H), 1.36 (d, 3H). MS (ES): MH$^+$ 434.

Example 48

N-(1-Methyl-1,2,3,4-tetrahydroquinolin-6-yl)-1,1'-biphenyl-4-carboxamide

Using the procedure outlined in Example 25, the title compound was prepared from N-methyl-6-amino-1,2,3,4-tetrahydroquinoline (International Patent Application, Publication number WO 94/14801) (75 mg, 0.46 mmol) and 4-biphenylcarboxylic acid (140 mg, 0.71 mmol) as a yellow gum. $^1$H NMR (250 MHz, CDCl$_3$) δ (ppm): 8.03 (d, 2H), 7.6-7.8 (m, 5H), 7.4-7.55 (m, 3H), 7.2-7.35 (m, 2H), 6.59 (d, 1H), 3.21 (m, 2H), 2.89 (s, 3H), 2.79 (m, 2H), 1.99 (m, 2H).

Example 49

N-(4,4-Dimethyl-1,2,3,4-tetrahydroisoquinolin-7-yl)-4-(3-trifluoromethyl-2-pyridyl)-piperazine-1-carboxamide To a stirred solution of 7-amino-4,4-dimethyl-1-trifluoroacetyl-1,2,3,4-tetrahydroisoquinoline (International Patent Application, Publication number WO 00/09486) (100 mg, 0.368 mmol) and pyridine (33 ul, 0.404 mmol) in DCM (5 ml) was added phenylchloroformate (51 ul, 0.404 mmol). The reaction mixture was stirred for 1 h at ambient temperature before triethylamine (56 ul, 0.404 mmol) was added and then left to stir for a further 30 min. After this period, 4-(3-trifluoromethyl-2-pyridyl)-piperazine (85 mg, 0.367 mmol) in DCM (5 ml) was added and the reaction stirred at ambient temperature for 18 h. On completion, the solvents were evaporated in vacuo and the residue purified directly by chromatography, eluting with 10-100% EtOAc/40-60° C. petroleum ether, to give N-(4,4-dimethyl-1-trifluoroacetyl-1,2,3,4-tetrahydroisoquinol-7-yl)-4-(3-trifluoromethyl-2-pyridiyl)-piperazine-1-carboxamide as a colourless oil. $^1$H NMR (400 MHz, CDCl$_3$) δ (ppm): 8.46 (dd 1H), 7.91 (dd, 1H), 7.05-7.35 (m, 4H), 6.39 (br-s, 1H), 4.77 (s, 2H), 3.60-3.65 (m, 5H), 3.53 (s, 1H), 3.30-3.35 (m, 4H), 1.20-1.25 (m, 6H). MS (ES): MH$^+$ 530.

A suspension of N-(4,4-dimethyl-1-trifluoroacetyl-1,2,3,4-tetrahydroisoquinol-7-yl)-4-(3-trifluoromethyl-2-pyridyl)-piperazine-1-carboxamide (30 mg, 0.057 mmol) and potassium carbonate (48 mg, 0.348 mmol) in methanol (4 ml) and water (4 ml) was heated at 50° C. for 6 h. After this period, the solvents were evaporated in vacuo and the residue partitioned between DCM (30 ml) and water (30 ml). The aqueous layer was re-extracted with DCM (2×30 ml) and then the combined organic layers dried (Na$_2$SO$_4$) and the solvents evaporated in vacuo to give the title compound as a white solid. $^1$H NMR (400 MHz, DMSO) δ (ppm): 8.45 (dd, 1H), 7.89 (dd, 1H), 7.22 (d, 1H), 7.10 (dd, 1H), 7.00-7.05 (m, 2H), 6.55 (s, 1H), 3.95 (s, 2H), 3.60-3.65 (m, 4H), 3.30-3.32 (m, 4H), 2.82 (s, 2H), 2.00 (br-s, 1H), 1.23 (s, 6H). MS (ES): MH$^+$ 434.

The following compounds shown in Table 3 were prepared as outlined above:

TABLE 3

| Example | Name | MH$^+$ |
| --- | --- | --- |
| 50 | N-(4,4-Dimethyl-1,2,3,4-tetrahydroisoquinolin-7-yl)-4-(3-chloro-2-pyridyl)-piperazine-1-carboxamide | 400/402 |
| 51 | N-(4,4-Dimethyl-1,2,3,4-tetrahydroisoquinolin-7-yl)-4-(3-chloro-5-trifluoromethyl-2-pyridyl)-piperazine-1-carboxamide | 468/470 |

Example 52

N-[4,4-Dimethyl-1,2,3,4-tetrahydroquinolin-7-yl-(3-chloro-pyridin-2-yl)-benzamide 7-Amino-4,4-dimethyl-1-trifluoroacetyl-1,2,3,4-tetrahydroquinoline (D28) (50 mg, 0.18 mmol) was combined with 4-(3-chloro-pyridin-2-yl)-benzoic acid (D84) (39.3 mg, 0.17 mmol), 1-(3-dimethylaminopropyl)-3-ethylcarbodiimide hydrochloride (38.5 mg, 0.2 mmol) and dimethylaminopyridine (10.2 mg, 0.08 mmol) in DCM (2 ml). The reaction was stirred for 16 h and then diluted with DCM (18 ml). The solution was washed with 10% citric acid (20 ml), saturated NaHCO$_3$ (20 ml) and brine (20 ml) then dried with Na$_2$SO$_4$ and concentrated. The resulting residue was purified by flash chromatography (EtOAc/40-60° C. pet.ether) to yield product as a white solid (19.3 mg). $^1$H NMR(400 MHz, CDCl$_3$) δ (ppm): 8.61-8.63(dd, 1H), 8.11 (s, 1H), 7.94-7.97(d, 2H), 7.74-7.86(m, 5H), 7.37-7.39(1H, d), 7.26-7.33(1H, m), 4.08-4.16(2H, m), 1.88-1.93(2H, m), 1.33 (6H, s). MH$^+$ 488/490.

N-[4,4-Dimethyl-1-trifluoroacetyl-1,2,3,4-tetrahydroquinolin-7--yl -(3-chloro-pyridin-2-yl)-phenylcarboxamide (19.3 mg, 0.04 mmol) and potassium carbonate (16 mg, 0.12 mmol) in water (2 ml) and methanol (2 ml) were heated at 50° C. for 3 h. The methanol was then evaporated in vacuo and the residue diluted with water (10 ml). The mixture was extracted with DCM (4×10 ml) and the combined organics were dried with Na$_2$SO$_4$ and the solvents evaporated in vacuo to give an off-white solid. This product was then taken up in methanol and 1M HCl in ether (41 µl) was added. Evaporation of the solvent gave the final product as an off-white solid. $^1$H NMR (400 MHz, DMSO) δ (ppm): 10.32(1H, s), 8.67-8.68(1H, m), 8.04-8.11(4H, m), 7.82-7.85(3H, d), 7.33(2H, bs), 3.31(2H, bs), 1.77(2H, bs), 1.27(6H, s). MS (ES): MH$^+$ 392/394.

Example 53

6-(3-Fluorophenyl)-2-methyl-N-(1,2,3,4-tetrahydroquinolin-7-yl)nicotinamide

Using the procedure outlined in Example 38, the title compound was prepared from 7-amino-1-trifluoroacetyl-1,2,3,4-tetrahydroquinoline (D5) (48 mg, 0.20 mmol) and 2-methyl-6-(3-fluorophenyl)-nicotinic acid (D25) (50 mg, 0.22 mmol) as an off-white solid. MS(ES): MH$^+$ 362, M-H$^+$ 360.

Example 54

6-(2,3-Difluorophenyl)-2-methyl-N-(1,2,3,4-tetrahydroquinolin-7-yl)nicotinamide

Using the procedure outlined in Example 38, the title compound was prepared from 7-amino-1-trifluoroacetyl-1,2,3,4-tetrahydroquinoline (D5) (48 mg, 0.20 mmol) and 2-methyl-6-(2,3-difluorophenyl)-nicotinic acid (D26) (54 mg, 0.22 mmol) as an off-white solid. MS(ES): MH$^+$ 380, M-H$^+$ 378.

Example 55

N-(5-Chloro-1,2,3,4-tetrahydro-quinolin-7-yl)-6-phenyl-nicotinamide

Using the procedure outlined in Example 38, the title compound was prepared from 7-amino-5-chloro-1-trifluoroacetyl-1,2,3,4-tetrahydroquinoline (D104) (50 mg, 0.251 mmol) and 6-phenyl nicotinic acid (60 mg, 0.302 mmol) as a white solid (55 mg). $^1$H NMR (400 MHz, CDCl$_3$) δ (ppm): 9.11 (s, 1H), 8.22 (dd, 1H), 8.05 (dd, 1H), 7.85 (d, 1H), 7.65 (br-s, 1H), 7.45-7.55 (m, 3H), 7.00 (br.s, 1H), 6.79 (d, 1H), 4.10 (br-s, 1H), 3.25-3.30 (m, 2H), 2.75-2.80 (m, 2H), 1.95-2.00 (m, 1H), 1.57 (s, 6H). MS(ES): MH$^+$ 364.

Example 56

N-Quinolin-7-yl-1,1'-biphenyl-4-carboxamide

To a solution of 7-aminoquinoline (D55) (100 mg, 0.69 mmol) in DCM (3 ml) was added 4-biphenylcarboxylic acid (206 mg, 1.04 mmol), 1-(3-dimethylamino-propyl)-3-ethyl-carbodiimide hydrochloride (197 mg, 1.04 mmol) and 4-dimethylaminopyridine (10 mg, 0.08 mmol) and the reaction stirred at room temperature overnight. The mixture was diluted with DCM, washed with sat. aqueous sodium bicarbonate solution, dried over MgSO$_4$ and concentrated in vacuo to give the crude product which was purified by SPE column chromatography. Elution with 50% EtOAc in 40-60° C. petroleum ether gave the title compound as an off-white solid. $^1$H NMR (400 MHz, CDCl$_3$) δ (ppm): 8.91 (dd, 1H), 8.19 (d, 1H), 8.12 (m, 2H), 8.02, (d, 2H), 7.86 (d, 1H), 7.75 (d, 2H), 7.65 (d, 2H), 7.49 (t, 2H), 7.42 (t, 1H), 7.36 (dd, 1H).

Example 57

6-Phenyl-N-quinolin-7-ylnicotinamide

Using the procedure outlined in Example 56, the title compound was prepared from 7-aminoquinoline (D55) (100 mg, 0.69 mmol) and 6-phenylnicotinic acid (D48) (198 mg, 1 mmol) as a solid. $^1$H NMR (400 MHz, CDCl$_3$) δ (ppm): 9.23 (d, 1H), 8.92 (dd, 1H), 8.33 (dd, 1H), 8.23 (s, 1H), 8.15, (d, 1H), 8.14 (s, 1H), 8.08 (m, 3H), 7.90 (d, 1H), 7.87 (d, 1H), 7.50 (m, 3H), 7.38 (dd, 1H).

Example 58

3'-Methyl-N-quinolin-7-yl-1,1'-biphenyl-4-carboxamide

To a solution of 4-bromo-N-quinolin-7-ylbenzamide (Example 82) (50 mg, 0.153 mmol) in toluene (2 ml) and ethanol (0.4 ml) under an argon atmosphere was added 3-methylphenylboronic acid (21 mg, 0.153 mmol), 2M sodium carbonate solution (0.15 ml) and tetrakis(triphenylphosphine) palladium (0) (5 mg, 0.05 mmol). The reaction was heated at reflux for 18 h, then cooled to room temperature and diluted with EtOAc. The mixture was washed with sat. aq. sodium bicarbonate solution and water, dried over MgSO$_4$ and concentrated to give the crude product which was purified by SPE column chromatography. Elution with 50% EtOAc in 40-60° C. petroleum ether gave the title compound as an off-white solid. $^1$H NMR (400 MHz, CDCl$_3$) δ (ppm): 8.92 (dd, 1H), 8.19 (d, 1H), 8.13 (m, 3H), 8.01, (d, 2H), 7.86 (d, 1H), 7.75 (d, 2H), 7.46 (m, 2H), 7.36 (m, 2H), 7.25 (m, 1H), 2.46 (s, 3H).

Example 59

2'-Methyl-N-quinolin-7-yl-1,1'-biphenyl-4-carboxamide

Using the procedure outlined in Example 58, the title compound was prepared from 4-bromo-N-quinolin-7-ylbenzamide (Example 82) (50 mg, 0.153 mmol) and 2-methyl-phenylboronic acid (23 mg, 0.168 mmol) as a white solid. $^1$H NMR (400 MHz, CDCl$_3$) δ (ppm): 8.92 (dd, 1H), 8.19 (d, 1H), 8.13 (m, 3H), 8.00, (d, 2H), 7.86 (d, 1H), 7.49 (d, 2H), 7.36 (dd, 1H), 7.29 (m, 4H), 2.30 (s, 3H).

Example 60

2'-Methoxy-N-quinolin-7-yl-1,1'-biphenyl-4-carboxamide

Using the procedure outlined in Example 58, the title compound was prepared from 4-bromo-N-quinolin-7-ylbenzamide (Example 82) (50 mg, 0.153 mmol) and 2-methoxyphenylboronic acid (25 mg, 0.168 mmol) as a colourless gum. $^1$H NMR (400 MHz, CDCl$_3$) δ (ppm): 8.91 (dd, 1H), 8.17 (d, 1H), 8.14 (m, 3H), 7.98, (d, 2H), 7.86 (d, 1H), 7.70 (d, 2H), 7.36 (m, 3H), 7.30 (d, 1H), 7.07 (t, 1H), 3.85 (s, 3H).

Example 61

2',6'-Dimethyl-N-quinolin-7-yl-1,1'-biphenyl-4-carboxamide

Using the procedure outlined in Example 58, the title compound was prepared from 4-bromo-N-quinolin-7-ylbenzamide (Example 82) (50 mg, 0.153 mmol) and 2,6-dimethylphenylboronic acid (25 mg, 0.17 mmol) as a white solid. $^1$H NMR (400 MHz, CDCl$_3$) δ (ppm): 8.92 (dd, 1H), 8.20 (d, 1H), 8.14 (m, 3H), 8.02, (d, 2H), 7.87 (d, 1H), 7.37 (dd, 1H), 7.34 (d, 2H), 7.21 (t, 1H), 7.14 (d, 2H), 2.05 (s, 6H).

Example 62

2'-Acetyl-N-quinolin-7-yl-1,1'-biphenyl-4-carboxamide

Using the procedure outlined in Example 58, the title compound was prepared from 4-bromo-N-quinolin-7-ylbenzamide (Example 82) (50 mg, 0.153 mmol) and 2-acetyl-phenylboronic acid (28 mg, 0.17 mmol) as an off-white solid. $^1$H NMR (400 MHz, CDCl$_3$) δ (ppm): 8.92 (dd, 1H), 8.21 (d, 1H), 8.20 (s, 1H), 8.14 (d, 1H), 8.10 (dd, 1H), 7.86 (d, 1H), 7.63 (dd, 1H), 7.57 (td, 1H), 7.48 (m, 3H), 7.40 (dd, 1H), 7.35 (dd, 1H), 3.85 (s, 3H).

Example 63

5'-Chloro-2'-methoxy-N-quinolin-7-yl-1,1'-biphenyl-4-carboxamide

Using the procedure outlined in Example 58, the title compound was prepared from 4-bromo-N-quinolin-7-ylbenzamide (Example 82) (65 mg, 0.199 mmol) and 5-chloro-2-methoxyphenylboronic acid (42 mg, 0.22 mmol) as a colourless gum. $^1$H NMR (400 MHz, CDCl$_3$) δ (ppm): 8.91 (dd, 1H), 8.18 (d, 1H), 8.13 (m, 3H), 7.98, (d, 2H), 7.86 (d, 1H), 7.66 (d, 2H), 7.36 (dd, 2H), 7.32 (m, 2H), 6.94 (d, 1H), 3.82 (s, 3H).

Example 64

4-(2,6-Dimethyl-3-pyridyl)-N-quinolin-7-ylbenzamide

Using the procedure outlined in Example 56, the title compound was prepared as the corresponding hydrochloride salt from 7-aminoquinoline (D55) (25 mg, 0.17 mmol) and 4-(2,6-dimethyl-3-pyridyl)benzoic acid (D56) (21 mg, 0.09 mmol) as a brown solid. $^1$H NMR (250 MHz, DMSO) δ (ppm): 9.15 (d, 1H), 9.01 (s, 1H), 8.94 (d, 1H), 8.28 (m, 5H), 7.84 (m, 2H), 7.72 (d, 2H), 2.79 (s, 3H), 2.70 (s, 3H).

Example 65

3-Methyl-4-(4-pyridyl)-N-quinolin-7-ylbenzamide

Using the procedure outlined in Example 56, the title compound was prepared from 7-aminoquinoline (D55) (25 mg, 0.17 mmol) and 3-methyl-4-(4-pyridyl)benzoic acid (D57) (44 mg, 0.21 mmol) as an orange solid. $^1$H NMR (400 MHz, CDCl$_3$) δ (ppm): 8.91(dd, 1H), 8.70 (d, 2H), 8.22 (m, 2H), 8.14 (dd, 1H), 8.11 (dd, 1H), 7.84 (m, 3H), 7.36 (m, 2H), 7.28 (m, 2H), 2.37 (s, 3H).

Example 66

3-Methyl-N-quinolin-7-yl-1,1'biphenyl-4-carboxamide

Using the procedure outlined in Example 56, the title compound was prepared from 7-aminoquinoline (D55) (31, 0.22 mmol) and 3-methyl-1,1'-biphenyl-4-carboxylic acid (D58) (55 mg, 0.26 mmol) as an off-white solid. $^1$H NMR (400 MHz, CDCl$_3$) δ (ppm): 8.91(dd, 1H), 8.14 (m, 3H), 7.86 (d, 1H), 7.78 (br, 1H), 7.66 (d, 1H), 7.62 (d, 2H), 7.53 (m, 2H), 7.48 (t, 2H), 7.40 (t, 1H), 7.36 (dd, 1H), 2.63 (s, 3H).

Example 67

3-Methoxy-N-quinolin-7-yl-1,1'biphenyl-4-carboxamide

Using the procedure outlined in Example 56, the title compound was prepared from 7-aminoquinoline (D55) (26 mg, 0.18 mmol) and 3-methoxy-1,1'-biphenyl-4-carboxylic acid (D59) (50 mg, 0.22 mmol) as an off-white solid. MS (ES): MH$^+$ 355.

Example 68

2-Methyl-N-quinolin-7-yl-1,1'biphenyl-4-carboxamide

Using the procedure outlined in Example 56, the title compound was prepared from 7-aminoquinoline (D55) (30 mg, 0.21 mmol) and 2-methyl-1,1'-biphenyl-4-carboxylic acid (D60) (53 mg, 0.25 mmol) as a white solid. MS(ES): MH$^+$ 339

Example 69

4-[(4-tert-Butoxycarbonyl)piperazin-1-yl]-2-methyl-N-quinolin-7-ylbenzamide

Using the procedure outlined in Example 56, the title compound was prepared from 7-aminoquinoline (D55) (17 mg, 0.12 mmol) and 4-[(4-tert-butoxycarbonyl)piperazin-1-yl]-2-methylbenzoic acid (D61) (47 mg, 0.14 mmol) as a yellow oil. MS(ES): MH$^+$ 447, M-H$^+$ 445.

Example 70

3,5-Dimethyl-4-(4-methyl-benzo[1,3]dioxol-5-yl)-N-quinolin-7-ylbenzamide

Using the procedure outlined in Example 56, the title compound was prepared from 7-aminoquinoline (D55) (17 mg, 0.12 mmol) and 3,5-dimethyl-4-(4-methyl-benzo[1,3]-dioxol-5-yl)-benzoic acid (D62) (41 mg, 0.15 mmol) as a yellow oil. MS(ES): MH$^+$ 411, M-H$^+$ 409.

Example 71

N-(2-Methylquinolin-7-yl)-1,1'-biphenyl-4-carboxamide

Using the procedure outlined in Example 56, the title compound was prepared from 7-amino-2-methylquinoline (D66) (80 mg, 0.51 mmol) and 4-biphenylcarboxylic acid (149 mg, 0.75 mmol) as an off-white solid. $^1$H NMR (400 MHz, CDCl$_3$) δ (ppm): 8.07 (m, 3H), 8.01 (m, 3H), 7.81 (d, 1H), 7.75 (d, 2H), 7.66 (d, 2H), 7.50 (t, 2H), 7.42 (t, 1H), 7.24 (d, 1H), 2.75 (s, 3H).

Example 72

N-(2-Methylquinolin-7-yl)-6-phenylnicotinamide

Using the procedure outlined in Example 56, the title compound was prepared from 7-amino-2-methylquinoline (D66) (100 mg, 0.63 mmol) and 6-phenylnicotinic acid (D48) (151 mg, 0.76 mmol) as a cream solid. $^1$H NMR (400 MHz, DMSO) δ (ppm): 10.75 (s, 1H), 9.25 (d, 1H), 8.50 (s, 1H), 8.45 (dd, 1H), 8.20 (m, 4H), 7.90 (m, 2H), 7.55 (m, 3H), 7.34 (d, 1H), 2.65 (s, 3H).

Example 73

3-Methyl-4-(4-pyridyl)-N-(2-methylquinolin-7-yl)-benzamide

Using the procedure outlined in Example 56, the title compound was prepared from 7-amino-2-methylquinoline (D66) (30 mg, 0.19 mmol) and 3-methyl-4-(4-pyridyl)benzoic acid (D57) (49 mg, 0.23 mmol) as an orange gum, (59 mg, 88%). $^1$H NMR (250 MHz, CDCl$_3$) δ (ppm): 8.70 (dd, 2H), 8.10 (s, 2H), 8.03 (m, 2H), 7.87 (s, 1H), 7.80 (d, 2H), 7.35 (d, 1H), 7.27 (m, 3H), 2.74 (s, 3H), 2.37 (s, 3H).

Example 74

N-(2-Methylquinolin-7-yl)-4-(2-pyridyl)benzamide

Using the procedure outlined in Example 56, the title compound was prepared from 7-amino-2-methylquinoline (D66)

(33 mg, 0.21 mmol) and 4-(2-pyridyl)benzoic acid (D67) (50 mg, 0.25 mmol) as a white solid. MS (ES): MH$^+$ 340, M-H$^+$ 338.

Example 75

N-(2-Methylquinolin-7-yl)-4-(1-pyrazolyl)benzamide

Using the procedure outlined in Example 56, the title compound was prepared from 7-amino-2-methylquinoline (D66) (33 mg, 0.21 mmol) and 4-(1-pyrazolyl)benzoic acid (47 mg, 0.25 mmol) as an off-white solid. MS (ES): MH$^+$ 329, M-H$^+$ 327.

Example 76

N-(2-Methylquinolin-7-yl)-4-(6-methyl-2-pyridyl) benzamide

Using the procedure outlined in Example 56, the title compound was prepared from 7-amino-2-methylquinoline (D66) (33 mg, 0.21 mmol) and 4-(6-methyl-2-pyridyl)benzoic acid (D29) (47 mg, 0.25 mmol) as an off-white solid. MS (ES): MH$^+$ 354, M-H$^+$ 352.

Example 77

N-(2-Methylquinolin-7-yl)-4-(N-morpholino)benzamide

A mixture of palladium (II) acetate (14 mg, 0.06 mmol), cesium carbonate (299 mg, 0.92 mmol) and BINAP (57 mg, 0.09 mmol) in dioxan (10 ml) was sonicated for 0.75 h under an argon atmosphere. To the resulting blood red solution was added a mixture of 4-bromo-N-quinolin-7-ylbenzamide (Example 82) (200 mg, 0.61 mmol) and morpholine (133 mg) in dioxane (10 ml) and the reaction was heated at 100° C. overnight. The resulting solution was concentrated in vacuo and the residue partitioned between DCM and water. The aqueous was further extracted with DCM and the combined organics were washed with sat. aq. sodium bicarbonate solution and brine, then dried over MgSO$_4$ and concentrated in vacuo to give the crude product. Purification by flash chromatography eluting with 5% MeOH/EtOAc gave the title compound as a yellow solid. $^1$H NMR (400 MHz, CDCl$_3$) δ (ppm): 8.89 (dd, 1H), 8.22 (dd, 1H), 8.16 (m, 2H), 8.09 (s, 1H), 7.88 (d, 2H), 7.85 (d, 1H), 7.37 (dd, 1H), 6.96 (d, 2H), 3.89 (m, 4H), 3.31 (m, 4H).

Example 78

N-(2-Methylquinolin-7-yl)-4-(N-piperidino)benzamide

A mixture of 4-bromo-N-quinolin-7-ylbenzamide (Example 82) (200 mg, 0.61 mmol), Pd$_2$(dba)$_3$ (8.4 mg, 1.5 mol %), Xantphos (21 mg, 6 mol %), cesium carbonate (298 mg, 0.92 mmol) and piperidine (78 mg, 0.92 mmol) in dioxan (10 ml) was heated at reflux under an argon atmosphere overnight. The mixture was concentrated in vacuo and the residue was partitioned between 9:1 DCM/MeOH and water. The aqueous was further extracted with 9:1 DCM/MeOH and the combined organics were washed with saturated aqueous sodium bicarbonate solution and brine, then dried over MgSO$_4$ and concentrated in vacuo to give the crude product. Purification by flash chromatography eluting with 50% EtOAc/DCM gave the title compound as a yellow solid. $^1$H NMR (400 MHz, CDCl$_3$) δ (ppm): 8.87 (dd, 1H), 8.13 (m, 4H), 7.83 (d, 2H), 7.80 (d, 1H), 7.32 (dd, 1H), 6.92 (d, 2H), 3.32 (m, 4H), 1.66 (m, 6H).

Example 79

4-Phenyl-N-quinolin-7-ylpiperazine-1-carboxamide

To a solution of di-tert-butyl tricarbonate (60 mg, 0.23 mmol) in DCM (1 ml) was added in one portion, a solution of 7-aminoquinoline (D55) (30 mg, 0.21 mmol) in DCM (1 ml). After 5 mins, when gas evolution was complete, tris-amine resin (12 mg 0.04 mmol) was added, then after 1 h a solution of 4-phenylpiperazine (32 ul, 0.21 mmol) was added and the reaction stirred at room temperature overnight. The reaction mixture was then purified directly by SPE column chromatography, eluting with an EtOAc/60-80° C.-petroleum ether gradient, followed by treatment with excess methyl isocyanate resin to remove unreacted 7-aminoquinoline starting material from the product. On completion the resin was removed by filtration and filtrate concentrated in vacuo to give the title compound as an orange gum. $^1$H NMR (250 MHz, CDCl$_3$) δ (ppm): 8.85 (dd, 1H), 8.09 (dd, 1H), 7.93 (dd, 1H), 7.82 (s, 1H), 7.76 (d, 1H), 7.30 (m, 3H), 6.94 (m, 3H), 6.83 (br, 1H), 3.72 (m, 4H), 3.28 (m, 4H).

Example 80

N-(2-Methylquinolin-7-yl)-4-phenylpiperazine-1-carboxamide

Using the procedure outlined in Example 79, the title compound was prepared from 7-amino-2-methylquinoline (D66) (100 mg, 0.63 mmol) and 4-phenylpiperazine (123 μl, 0.76 mmol) as an off-white solid. $^1$H NMR (400 MHz, CDCl$_3$) δ (ppm): 7.97 (d, 1H), 7.84 (dd, 1H), 7.72 (s, 1H), 7.69 (dd, 1H), 7.30 (t, 2H), 7.18 (d, 1H), 6.95 (d, 2H), 6.92 (t, 1H), 6.70 (br, 1H), 3.72 (m, 4H), 3.27 (m, 4H), 2.71 (s, 3H).

Example 81

4-Phenyl-N-quinolin-7-yl-piperidine-1-carboxamide

Using the procedure outlined in Example 79, the title compound was prepared from 7-aminoquinoline (D55) (30 mg, 0.21 mmol) and 4-phenylpiperidine (40 mg, 0.25 mmol) as an orange gum. $^1$H NMR (400 MHz, CDCl$_3$) δ (ppm): 8.84 (dd, 1H), 8.08 (dd, 1H), 7.93 (dd, 1H), 7.78 (s, 1H), 7.27 (m, 6H), 6.78 (br, 1H), 4.29 (m, 2H), 3.06 (td, 2H), 2.76 (tt, 1H), 1.96 (m, 2H), 1.80 (td, 2H).

Example 82

4-Bromo-N-quinolin-7-yl-benzamide

Using the procedure outlined in Example 56, the title compound was prepared from 7-aminoquinoline (D55) (720 mg, 5 mmol) and 4-bromobenzoic acid (1.51 g, 7.5 mmol) as a white solid. $^1$H NMR (400 MHz, CDCl$_3$) δ (ppm): 8.91 (dd, 1H), 8.18 (d, 1H), 8.14 (dd, 1H), 8.06, (m, 2H), 7.85 (d, 1H), 7.81 (d, 2H), 7.67 (d, 2H), 7.37 (dd, 1H).

Example 83

3'-Dimethylsulfamoyl-N-quinolin-7-yl-1,1'-biphenyl-4-carboxamide

Using the procedure outlined in Example 56, the title compound was prepared from 7-aminoquinoline (D55) (18 mg, 0.13 mmol) and 3'-dimethylsulfamoyl-1,1'-biphenyl-4-carboxylic acid (D68) (45 mg, 0.15 mmol) as a yellow oil. MS(ES): MH$^+$ 432, M-H$^+$ 430

Example 84

4-Cyclohexyl-N-quinolin-7-yl-benzamide

Using the procedure outlined in Example 45, the title compound was prepared from 7-aminoquinoline (D55) (30 mg, 21 mmol) and 4-cyclohexylbenzoic acid (51 mg, 0.25 mmol) as a yellow solid. MS(ES): MH$^+$ 331, M-H$^+$ 329

Example 85

4-tert-Butyl-N-quinolin-7-yl-benzamide

Using the procedure outlined in Example 45, the title compound was prepared from 7-aminoquinoline (D55) (30 mg, 21 mmol) and 4-tert-butylbenzoic acid (45 mg, 0.25 mmol) as a yellow solid. MS(ES): MH$^+$ 305, M-H$^+$ 303

Example 86

4-iso-Propyl-N-quinolinyl-benzamide

Using the procedure outlined in Example 45, the title compound was prepared from 7-aminoquinoline (D55) (30 mg, 21 mmol) and 4-isopropylbenzoic acid (41 mg, 0.25 mmol) as a yellow solid. MS(ES): MH$^+$ 291, M-H$^+$ 289

Example 87

N-Quinolinyl-4-trifluoromethyl-benzamide

Using the procedure outlined in Example 45, the title compound was prepared from 7-aminoquinoline (D55) (30 mg, 21 mmol) and 4-trifluoromethyl-benzoic acid (48 mg, 0.25 mmol) as a yellow solid. MS(ES): MH$^+$ 317, M-H$^+$ 315

Example 88

9-Oxo-9H-fluorene-2-carboxylic acid quinolin-7-yl amide

To a solution of 7-aminoquinoline (D55) (35 mg, 0.24 mmol) in DCM (3 ml) was added 9-oxo-9H-fluorene-2-carboxylic acid (60 mg, 0.27 mmol), (3-dimethylamino-propyl)-ethyl-carbodiimide hydrochloride (68 mg, 0.36 mmol) and 4-dimethylaminopyridine (5 mg, 0.04 mmol) and the reaction stirred at room temperature then at reflux until complete by tlc. After cooling to room temperature the resultant precipitate was filtered off to give the title compound as an off-white solid. MS(ES): MH$^+$ 351, M-H$^+$ 349

Example 89

2-Methyl-N-quinolin-7-yl-6-trifluoromethyl-nicotinamide

Using the procedure outlined in Example 45, the title compound was prepared from 7-aminoquinoline (D55) (30 mg, 21 mmol) and 2-ethyl-6-trifluoromethylnicotinic acid (51 mg, 0.25 mmol) as a yellow solid. MS(ES): MH$^+$ 332, M-H$^+$ 330

Example 90

4-(3-Pyridyl)-N-quinolin-7-yl-benzamide

Using the procedure outlined in Example 58, the title compound was prepared from 4-bromo-N-quinolin-7-ylbenzamide (Example 82) (50 mg, 0.15 mmol) and 3-pyridylboronic acid (20 mg, 0.16 mmol) as a white solid. $^1$H NMR (400 MHz, CDCl$_3$) δ (ppm): 8.89 (d, 1H), 8.87 (dd, 1H), 8.65 (m, 1H), 8.26 (dd, 1H), 8.17 (dd, 1H), 8.14 (d, 1H), 8.09 (d, 2H), 7.96 (m, 1H), 7.88 (d, 1H), 7.74 (d, 2H), 7.45 (dd, 1H), 7.38 (dd, 1H).

Example 91

4-(4-Pyridyl)-N-quinolin-7-yl-benzamide

Using the procedure outlined in Example 58, the title compound was prepared from 4-bromo-N-quinolin-7-ylbenzamide (Example 82) (50 mg, 0.15 mmol) and 4-pyridylboronic acid (20 mg, 0.16 mmol) as a white solid. $^1$H NMR (400 MHz, CDCl$_3$) δ (ppm): 8.86 (d, 1H), 8.70 (d, 2H), 8.33 (dd, 1H), 8.18 (d, 1H), 8.12 (d, 2H), 8.07 (s, 1H), 7.88 (d, 1H), 7.79 (d, 2H), 7.58 (d, 2H), 7.38 (dd, 1H).

Example 92

(R)-2-Methyl-4-(3-trifluoromethyl-2-pyridyl)-N-quinolin-7-yl) piperazine-1-carboxamide Using the procedure outlined in Example 79, the title compound was prepared from 7-aminoquinoline (D55) (60 mg, 0.417 mmol) and (R)-2-methyl-4-(3-trifluoromethyl-2-pyridyl)piperazine (D22) (123 mg, 0.50 mmol) as a colourless oil. $^1$H NMR (400 MHz, CDCl$_3$) δ (ppm): 8.92 (1H, d), 8.66-8.69 (2H, m), 8.50 (2H, d), 8.27 (1H, bs), 7.99 (1H, d), 7.94 (1H, dd), 7.65-7.68 (1H, m), 7.09-7.12 (1H, m), 4.55 (1H, m), 4.06 (1H, d), 3.50-3.56 (2H, m), 3.41 (1H, d, J=), 3.26 (1H, dd), 3.01-3.08 (1H, m), 1.40 (3H, d). MS(ES): MH$^+$ 416.

Example 93

2-Methoxy-N-quinolin-7-yl-1,1'-biphenyl-4-carboxamide

Using the procedure outlined in Example 58, the title compound was prepared from 4-bromo-3-methoxy-N-quinolin-7-ylbenzamide (D69) (76 mg, 0.21 mmol) and phenylboronic acid (28 mg, 0.23 mmol) as a white solid. MS(ES): MH$^+$ 355, M-H$^+$ 353.

Example 94

6-(4-Methylpiperidin-1-yl)-N-quinolin-7-yl-nicotinamide

6-Chloro-N-quinolinylnicotinamide (D70) (50 mg, 0.18 mmol), 4-methylpiperidine (25 ul, 0.21 mmol) and potassium carbonate (73 mg, 0.53 mmol) in DMF (2 ml) were heated at 120° C. overnight. Further 4-methylpiperidine (11 ul, 0.09 mmol) was added and heating continued overnight. On cooling the reaction mixture was diluted with EtOAc and washed with water, then dried over MgSO$_4$ and concentrated to give the crude product. Purification by SPE column chromatography gave the title compound as a yellow solid. MS(ES): MH$^+$ 347, M-H$^+$ 345.

Example 95

2-Methyl-N-quinolin-7-yl-6-(2-thienyl)-nicotinamide

Using the procedure outlined in Example 45, the title compound was prepared from 7-aminoquinoline (D55) (7 mg, 0.05 mmol) and 2-methyl-6-(2-thienyl)-nicotinic acid (10 mg, 0.05 mmol) as a yellow solid. $^1$H NMR (400 MHz, MeOH-d$_4$) δ (ppm): 8.82 (dd, 1H), 8.58 (s, 1H), 8.34 (dd, 1H), 7.85-8.0 (m, 3H), 7.76 (m, 2H), 7.55 (dd, 1H), 7.48 (dd, 1H), 7.16 (dd, 1H), 2.70 (s, 3H).

Example 96

6-Piperidin-1-yl-N-quinolin-7-yl-nicotinamide

Using the procedure outlined in Example 94, the title compound was prepared from 6-chloro-N-quinolinylnicotinamide (D70) (50 mg, 0.18 mmol) and piperidine (30 ul, 0.30 mmol) to give the title compound as a yellow solid. MS(ES): MH$^+$ 333, M-H$^+$ 331.

Example 97

4-(4-Fluorophenyl)-N-quinolin-7-yl piperazine-1-carboxamide

Using the procedure outlined in Example 47, the title compound was prepared from 7-aminoquinoline (D55) (30 mg, 0.21 mmol) and 4-(4-fluorophenyl)-piperazine (37 mg, 0.21 mmol) as an off-white solid. MS(ES): MH$^+$ 351, M-H$^+$ 349

Example 98

(R)-2-Methyl-4-(6-methyl-2-pyridyl)-N-quinolin-7-yl)-piperazine-1-carboxamide

Using the procedure outlined in Example 47, the title compound was prepared from 7-aminoquinoline (D55) (30 mg, 0.21 mmol) and (R)-2-methyl-4-(6-methyl-2-pyridyl)piperazine (D99) (40 mg, 0.21 mmol) as an off-white solid. $^1$H NMR (400 MHz, CDCl$_3$) (ppm): 8.85 (dd, 1H), 8.09 (dd, 1H), 7.94 (dd, 1H), 7.80 (d, 1H), 7.77 (d, 1H), 7.40 (dd, 1H), 7.30 (dd, 1H), 6.69 (s, 1H), 6.52 (d, 1H), 6.44 (d, 1H), 4.41 (m, 1H), 4.25 (m, 1H), 4.06 (m, 1H), 4.00 (m, 1H), 3.49 (ddd, 1H), 3.38 (dd, 1H), 3.11 (ddd, 1H), 2.42 (s, 3H), 1.37 (d, 3H).

Example 99

6-(4-Fluorophenyl)-N-quinolin-7-yl-nicotinamide

Using the procedure outlined in Example 56, the title compound was prepared from 7-aminoquinoline (D55) (50 mg, 0.35 mmol) and 6-(4-fluoro-phenylnicotinic acid (D24) (83 mg, 0.38 mmol) as a cream solid. $^1$H NMR (250 MHz, CDCl$_3$) δ (ppm): 9.23 (dd, 1H), 8.86 (dd, 1H), 8.37 (dd, 1H), 8.26 (dd, 1H), 8.18 (m, 2H), 8.08 (d, 1H), 8.06 (d, 1H), 7.85 (dd, 2H), 7.38 (dd, 1H), 7.20 (t, 2H).

Example 100

N-Quinolin-7-yl-6-(4-trifluoromethylphenyl)-nicotinamide

To a solution of 6-chloro-N-quinolin-7-yl-nicotinamide (D70) (40 mg, 0.14 mmol) in DME (0.9 ml) under an argon atmosphere was added 4-trifluoromethylphenylboronic acid (33 mg, 0.17 mmol), 2M sodium carbonate solution (0.17 ml) and tetrakis(triphenylphosphine)palladium (0) (8 mg, 0.007 mmol). The reaction was heated at reflux until complete by tlc, then cooled to room temperature and diluted with EtOAc and dried over MgSO$_4$. The solvent was removed in vacuo and the resultant crude product was purified by SPE column chromatography. Elution with 75% EtOAc in 40-60° C. petroleum ether gave the title compound as an off-white solid. $^1$H NMR (250 MHz, CDCl$_3$) δ (ppm): 9.31 (dd, 1H), 8.83 (dd, 1H), 8.46 (dd, 1H), 8.39 (dd, 1H), 8.20 (m, 3H), 8.07 (d, 1H), 7.94 (dd, 1H), 7.89 (d, 1H), 7.79 (d, 2H), 7.40 (dd, 1H).

Example 101

9H-Fluorene-2-carboxylic acid quinolin-7-yl amide

Using the procedure outlined in Example 56, the title compound was prepared from 7-aminoquinoline (D55) (50 mg, 0.35 mmol) and 9H-fluorene-2-carboxylic acid (D71) (83 mg, 0.38 mmol) as an off-white solid. MS(ES): MH$^+$ 337, M-H$^+$ 335.

Example 102

6-(4-Chlorophenyl)-N-quinolin-7-yl-nicotinamide

Using the procedure outlined in Example 100, the title compound was prepared from 6-chloro-N-quinolin-7-yl-nicotinamide (D70) (40 mg, 0.14 mmol) and 4-chlorophenylboronic acid (27 mg, 0.17 mmol) as a pale yellow solid. $^1$H NMR (250 MHz, CDCl$_3$) δ (ppm): 9.25 (dd, 1H), 8.82 (dd, 1H), 8.43 (dd, 1H), 8.33 (dd, 1H), 8.22 (br.d, 1H), 8.11 (d, 1H), 8.00 (d, 2H), 7.89 (d, 1H), 7.87 (d, 1H), 7.51 (d, 2H), 7.40 (dd, 1H).

Example 103

6-(3,4-Difluorophenyl)-N-quinolin-7-yl-nicotinamide

Using the procedure outlined in Example 100, the title compound was prepared from 6-chloro-N-quinolin-7-yl-nicotinamide (D70) (40 mg, 0.14 mmol) and 3,4-difluorophenylboronic acid (27 mg, 0.17 mmol) as a cream solid. $^1$H NMR (250 MHz, CDCl$_3$) δ (ppm): 9.24 (dd, 1H), 8.86 (dd, 1H), 8.39 (dd, 1H), 8.28 (dd, 1H), 8.14 (br.d, 1H), 8.13 (d, 1H), 7.97 (ddd, 1H), 7.85 (m, 3H), 7.39 (dd, 1H), 7.28 (m, 1H).

Example 104

4-(2-Methylpyrid-4-yl)-N-quinolin-7-yl-benzamide

To a solution of 7-aminoquinoline (D55) (338 mg, 0.26 mmol) in DCM (3 ml) was added 4-(2-methylpyrid-4-yl)-benzoic acid (D72) (62 mg, 0.29 mmol), 1-(3-dimethylamino-propyl)-3-ethyl-carbodiimide hydrochloride (74 mg, 0.39 mmol) and 4-dimethylaminopyridine (6 mg, 0.05 mmol) and the reaction stirred at room temperature until complete by tlc. The resultant precipitate was filtered off to give the title compound as an off-white solid. MS(ES): MH$^+$ 340, M-H$^+$ 338

Example 105

6-(3-Fluorophenyl)-N-quinolin-7-yl-nicotinamide

Using the procedure outlined in Example 104, the title compound was prepared from 7-aminoquinoline (D55) (28 mg, 0.19 mmol) and 6-(3-fluorophenyl)-nicotinic acid (D73) (50 mg, 0.23 mmol) as a yellow solid. MS(ES): MH$^+$ 344, M-H$^+$ 342

Example 106

6-(2-Fluorophenyl)-N-quinolin-7-yl-nicotinamide

Using the procedure outlined in Example 104, the title compound was prepared from 7-aminoquinoline (D55) (28 mg, 0.19 mmol) and 6-(2-fluorophenyl)-nicotinic acid (D74) (50 mg, 0.23 mmol) as a yellow solid. MS(ES): MH$^+$ 344, M-H$^+$ 342

Example 107

N-Quinolin-7-yl-1-(5-trifluoromethylpyrid-2-yl)-piperidine-4-carboxamide 1-(5-Trifluoromethylpyrid-2-yl)-piperidine-4-carboxylic acid (D101) (100 mg, 0.36 mmol) was treated with oxalyl chloride (63 ul, 0.72 mmol) and catalytic DMF in 1,2-dichloroethane (3.5 ml) at 60° C. for 0.75 h. On cooling to room temperature the solvent was removed in vacuo and the residue was dissolved in DCM (2 ml). Triethylamine (30 ul, 0.2 mmol) and 7-aminoquinoline (D55) (27 mg, 0.19 mmol) were added and the reaction stirred at room temperature until complete by tlc. The resultant precipitate was collected by filtration to give the title compound as an off-white solid. MS(ES): MH$^+$ 401, M-H$^+$ 399.

Example 108

2-Methyl-6-phenyl-N-quinolin-7-yl-nicotinamide

Using the procedure outlined in Example 56, the title compound was prepared from 7-aminoquinoline (D55) (28 mg, 0.9 mmol) and 2-methyl-6-phenylnicotinic acid (D23) (50 mg, 0.24 mmol) as a yellow solid. MS(ES): MH$^+$ 340, M-H$^+$ 338

Example 109

6-(4-Fluorophenyl)-2-methyl-N-quinolin-7-yl-nicotinamide

Using the procedure outlined in Example 45, the title compound was prepared from 7-aminoquinoline (D55) (26 mg, 0.8 mmol) and 6-(4-fluorophenyl)-2-methylnicotinic acid (D24) (50 mg, 0.22 mmol) as a white solid. MS(ES): MH$^+$ 358, M-H$^+$ 356.

Example 110

N-Quinolin-7-yl-1-(6-trifluoromethylpyrid-2-yl)-piperidine-4-carboxamide

Using the procedure outlined in Example 107, the title compound was prepared from 1-(6-trifluoromethylpyrid-2-yl)-piperidine-4-carboxylic acid (D102) (100 mg, 0.36 mmol) and 7-aminoquinoline (D55) (27 mg, 0.19 mmol) as an off white solid. MS(ES): MH$^+$ 401, M-H$^+$ 399.

Example 111

4'-Fluoro-2-(2-methoxyethoxy)-N-quinolin-7-yl-1,1'-biphenyl-4-carboxamide

Using the procedure outlined in Example 56, the title compound was prepared from 7-aminoquinoline (D55) (21 mg, 0.14 mmol) and 4'-fluoro-2-(2-methoxyethoxy)-1,1'-biphenyl-4-carboxylic acid (D77) (50 mg, 0.17 mmol) as an orange solid. MS(ES): MH$^+$ 417, M-H$^+$ 415

Example 112

2-(2-Dimethylaminoethoxy)-4'-fluoro-N-quinolin-7-yl-1,1'-biphenyl-4-carboxamide

Using the procedure outlined in Example 56, the title compound was prepared from 7-aminoquinoline (D55) (20 mg, 0.14 mmol) and 2-(2-dimethylaminoethoxy)-4'-fluoro-1,1'-biphenyl-4-carboxylic acid (D79) (50 mg, 0.17 mmol) as a yellow solid. MS(ES): MH$^+$ 430, M-H$^+$ 428

Example 113

N-(5-Chloroquinolin-7-yl)-6-(4-Fluorophenyl)-2-ethyl-nicotinamide

To a solution of 7-amino-5-chloroquinoline (D83) (50 mg, 0.28 mmol) in DCM (3 ml) was added 6-(4-fluorophenyl)-2-methyl-nicotinic acid (D24) (30 mg, 0.13 mmol), 1-(3-dimethylaminopropyl)-3-ethyl-carbodiimide hydrochloride (59 mg, 0.31 mmol) and 4-dimethylaminopyridine (17 mg, 0.14 mmol) and the reaction stirred at room temperature then at reflux until complete by tlc. The mixture was washed with sat. aq. sodium bicarbonate solution then dried over MgSO$_4$ and concentrated to give the crude product. Purification by SPE column chromatography gave the title compound as an off white solid. $^1$H NMR (400 MHz, CDCl$_3$) δ (ppm): 8.94 (dd, 1H), 8.54 (d, 1H), 8.29 (s, 1H), 8.05 (m, 3H), 7.92 (d, 1H), 7.78 (br.s, 1H), 7.62 (d, 1H), 7.47 (dd, 1H), 7.18 (t, 2H), 2.84 (s, 3H).

Example 114

4-(3-Chloro-2-pyridinyl)-N-quinolin-7-yl-benzamide

Using the procedure outlined in Example 56, the title compound was prepared from 7-aminoquinoline (D55) (25 mg, 0.14 mmol) and 4-(3-Chloro-2-pyridyl)-benzoic acid (D84) (50 mg, 0.17 mmol) as a brown solid. MS(ES): MH$^+$ 362/360, M-H$^+$ 360/358.

Example 115

6-(4-Fluorophenyl)-2-(methoxymethyl)-N-quinolin-7-yl-nicotinamide

Using the procedure outlined in Example 56, the title compound was prepared from 7-aminoquinoline (D55) (11 mg, 0.076 mmol) and 6-(4-fluorophenyl)-2-(methoxymethyl)-nicotinic acid (D86) (19 mg, 0.073 mmol) as an orange solid. $^1$H NMR (250 MHz, CDCl$_3$) δ (ppm): 10.40 (br.s, 1H), 8.92 (dd, 1H), 8.41 (d, 1H), 8.29 (d, 1H), 8.05-8.20 (m, 4H), 7.85 (m, 2H), 7.36 (dd, 1H), 7.20 (t, 2H), 4.91 (s, 2H), 3.68 (s, 3H).

Example 116

6-(4-Fluorophenyl)-2-methyl-N-(2-methylquinolin-7-yl)-nicotinamide

Using the procedure outlined in Example 56, the title compound was prepared from 7-amino-2-methylquinoline (D66) (20 mg, 0.13 mmol) and 6-(4-fluorophenyl)-2-methylnicotinic acid (D24) (30 mg, 0.13 mmol) then converted to the HCl salt as a beige solid by treatment with ethereal HCl. $^1$H NMR (400 MHz, DMSO) (HCl salt) δ (ppm): 11.39 (br.s, 1H), 9.04 (s, 1H), 8.96 (d, 1H), 8.30 (d, 1H), 8.23 (dd, 2H), 8.12 (d, 1H), 8.00 (m, 2H), 7.84 (d, 1H), 7.37 (t, 2H), 2.94 (s, 3H), 2.71 (s, 3H)

Example 117

6-(3-Fluorophenyl)-2-methyl-N-quinolin-7-yl-nicotinamide

Using the procedure outlined in Example 56, the title compound was prepared from 7-aminoquinoline (D55) (28 mg, 0.20 mmol) and 6-(3-fluorophenyl)-2-methyl-nicotinic acid (D25) (50 mg, 0.33 mmol), as an off-white solid. MS(ES): MH+ 358, M-H+ 356.

Example 118

6-(2,3-Difluorophenyl)-2-methyl-N-quinolin-7-yl-nicotinamide

Using the procedure outlined in Example 56, the title compound was prepared from 7-aminoquinoline (D55) (28 mg, 0.20 mmol) and 6-(2,3-difluorophenyl)-2-methyl-nicotinic acid (D26) (54 mg, 0.33 mmol), as a brown solid. MS(ES): MH+ 376, M-H+ 374.

Example 119

4-(2-Methylthiazol-4yl)-N-quinolin-7-yl-benzamide

Using the procedure outlined in Example 56, the title compound was prepared from 7-aminoquinoline (D55) (27 mg, 0.19 mmol) and 4-(2-methylthiazol-4-yl)-benzoic acid (D87) (50 mg, 0.23 mmol) as a solid. MS(ES): MH+ 346, M-H+ 344

Example 120

N-(4-Methyl-2-oxo-1,2-dihydro-quinolin-7-yl)-1,1'-biphenyl-4-carboxamide

Using the procedure outlined in Example 56, the title compound was prepared from 7-amino-4-methyl-1-H-quinolin-2-one (50 mg, 0.29 mmol) and 4-biphenylcarboxylic acid (68 mg, 0.34 mmol) as a cream solid. $^1$H NMR (250 MHz, DMSO) δ (ppm): 11.60 (br, 1H), 10.55 (br, 1H), 8.09 (d, 2H), 8.02 (s, 1H), 7.86 (d, 2H), 7.77 (d, 2H), 7.69 (d, 1H), 7.55 (dd, 1H), 7.52 (t, 2H), 7.43 (t, 1H), 6.29 (s, 1H), 2.41 (s, 3H).

Example 121

N-(1,4-Dimethyl-2-oxo-1,2-dihydro-quinolin-7-yl)-1,1'-biphenyl-4-carboxamide

Using the procedure outlined in Example 56, the title compound was prepared from 7-amino-1,4-methyl-1H-quinolin-2-one (D89) (64 mg, 0.34 mmol) and 4-biphenylcarboxylic acid (82 mg, 0.41 mmol) as a pale pink solid. $^1$H NMR (250 MHz, DMSO) δ (ppm): 10.58 (br, 1H), 8.14 (s, 1H), 8.12 (d, 2H), 7.88 (d, 2H), 7.80 (m, 4H), 7.53 (t, 2H), 7.42 (t, 1H), 6.44 (d, 1H), 3.60 (s, 3H), 2.43 (d, 3H).

Example 122

N-(2-Oxo-1,2-dihydro-quinolin-7-yl)-1,1'-biphenyl-4-carboxamide

Using the procedure outlined in Example 56, the title compound was prepared from 7-amino-1H-quinolin-2-one (D89) (30 mg, 0.19 mmol) and 4-biphenylcarboxylic acid (44 mg, 0.22 mmol) as an off-white solid. $^1$H NMR (400 MHz, DMSO) δ (ppm): 11.80 (br, 1H), 10.58 (br, 1H), 8.09 (d, 2H), 8.04 (d, 1H), 7.85 (m, 3H), 7.77 (d, 2H), 7.62 (d, 1H), 7.52 (m, 3H), 7.44 (t, 1H), 6.39 (d, 1H).

Example 123

N-(2-Oxo-1,2-dihydro-quinolin-7-yl)-6-phenylnicotinamide

Using the procedure outlined in Example 56, the title compound was prepared from 7-amino-1H-quinolin-2-one (D89) (30 mg, 0.19 mmol) and 6-phenylnicotinic acid (D48) (45 mg, 0.22 mmol) as an off-white solid. $^1$H NMR (400 MHz, DMSO) δ (ppm): 11.80 (br, 1H), 10.73 (br, 1H), 9.21 (d, 1H), 8.42 (dd, 1H), 8.18 (m, 3H), 8.01 (d, 1H), 7.84 (d, 1H), 7.64 (d, 1H), 7.53 (m, 4H), 6.40 (dd, 1H).

Example 124

N-(Isoquinolin-5-yl)-1,1'-biphenyl-4-carboxamide

To a solution of 5-aminoisoquinoline (72 mg, 0.5 mmol) in DCM (3 ml) was added 4-biphenylcarboxylic acid (149 mg, 0.75 mmol), 1-(3-dimethylaminopropyl)-3-ethyl-carbodiimide hydrochloride (143 mg, 0.75 mmol) and 4-dimethylaminopyridine (9 mg, 0.08 mmol) and the reaction stirred at room temperature overnight. The mixture was diluted with DCM, washed with 2M sodium hydroxide solution and 2M hydrochloric acid causing precipitation of a white solid which was filtered off and dried in vacuo to give the HCl salt of the title compound. $^1$H NMR (400 MHz, DMSO) δ (ppm): 10.94 (s, 1H), 9.88 (s, 1H), 8.67 (d, 1H), 8.41 (d, 1H), 8.38 (d, 1H), 8.24 (m, 3H), 8.04 (t, 1H), 7.91 (d, 2H), 7.80 (d, 2H), 7.54 (t, 2H), 7.45 (t, 1H), 4.00 (br).

Example 125

N-(1-Methylisoquinolin-5-yl)-1,1'-biphenyl-4-carboxamide

To a solution of 1-methyl-5-aminoisoquinoline (94 (75 mg, 0.47 mmol) in DCM (4 ml) was added 4-biphenylcarboxylic acid (141 mg, 0.71 mmol), 1-(3-dimethylaminopropyl)-3-ethyl-carbodiimide hydrochloride (135 mg, 0.71 mmol) and 4-dimethylaminopyridine (10 mg, 0.08 mmol) and the reaction stirred at 38° C. for 3 days. The mixture was diluted with DCM, washed with sat. aqueous sodium bicarbonate solution and water, dried over MgSO$_4$ and concentrated in vacuo to give the crude product which was triturated with methanol. The resulting precipitate was collected by filtration, washed with ether and dried in vacuo giving the title compound as an off-white solid. $^1$H NMR (400 MHz, CDCl$_3$) δ (ppm): 8.48 (d, 1H), 8.33 (d, 1H), 8.21 (br, 1H), 8.06 (m, 3H), 7.78 (d, 2H), 7.68 (m, 3H), 7.58 (d, 1H), 7.51 (t, 2H), 7.41 (t, 1H), 3.02 (s, 3H).

Example 126

N-(Isoquinolin-5-yl)-3'-methyl-1,1'-biphenyl-4-carboxamide

To a solution of 4-bromo-N-isoquinolin-5-ylbenzamide (D94) (50 mg, 0.153 mmol) in toluene (2 ml) and ethanol (0.4 ml) under an argon atmosphere was added 3-methyl-phenyl-boronic acid (21 mg, 0.153 mmol), 2M sodium carbonate solution (0.15 ml) and tetrakis(triphenylphosphine)palladium (0) (5 mg, 0.05 mmol). The reaction was heated at reflux for 18 h, then cooled to room temperature and diluted with EtOAc. The mixture was washed with sat. aq. sodium bicarbonate solution and water, dried over $MgSO_4$ and concentrated to give the crude product which was purified by SPE column chromatography. Elution with 50% EtOAc/40-60° C. petroleum ether gave the title compound as an off-white solid. $^1$H NMR (400 MHz, $CDCl_3$) δ (ppm): 9.32 (s, 1H), 8.62 (d, 1H), 8.34 (d, 1H), 8.22 (br, 1H), 8.07 (d, 2H), 7.90, (d, 1H), 7.78 (d, 2H), 7.70 (m, 3H), 7.47 (m, 2H), 7.40 (t, 1H), 2.47 (s, 3H).

Example 127

N-(Isoquinolin-8-yl)-1,1'-biphenyl-4-carboxamide

Using the procedure outlined in Example 56, the title compound was prepared from 8-aminoisoquinoline (D95) (85 mg, 0.59 mmol) and 4-biphenylcarboxylic acid (177 mg, 0.89 mmol) as an off-white solid. $^1$H NMR (400 MHz, $CDCl_3$) δ (ppm): 9.48 (s, 1H), 8.61 (d, 1H), 8.42 (br.s, 1H), 8.22 (d, 1H), 8.10 (d, 2H), 7.79 (d, 2H), 7.68-7.76 (m, 5H), 7.51 (t, 2H), 7.43 (t, 1H).

Example 128

N-(Isoquinolin-7-yl)-1,1'-biphenyl-4-carboxamide

To a solution of 7-aminoisoquinoline (D96) (88 mg, 0.61 mmol) in DCM (4 ml) was added 4-biphenylcarboxylic acid (145 mg, 0.73 mmol) and 1-(3-dimethylaminopropyl)-3-ethylcarbodiimide hydrochloride (140 mg, 0.73 mmol) and the reaction stirred at ambient temperature overnight. The reaction mixture was filtered to give the title compound as a white solid. The filtrate was diluted with DCM, washed with 2M sodium hydroxide solution, dried over $MgSO_4$ and concentrated in vacuo to give further crude product which was purified by silica SPE chromatography. Elution with an EtOAc/60-80° C. petroleum ether gradient gave a further title compound which was combined with the sample obtained from the filtration. This was dissolved in ethanol and treated with ethereal HCl and the resultant precipitate was collected to give the HCl salt of the title compound as a white solid. $^1$H NMR (250 MHz, DMSO) δ (ppm): 9.80 (s, 1H), 9.09 (d, 1H), 8.58 (d, 1H), 8.40 (dd, 1H), 8.33 (d, 1H), 8.28 (d, 1H), 8.16 (d, 2H), 7.90 (d, 2H), 7.79 (d, 2H), 7.54 (t, 2H), 7.45 (t, 1H)

Example 129

N-(Isoquinolin-6-yl)-1,1'-biphenyl-4-carboxamide

Using the procedure outlined in Example 56, the title compound was prepared from 6-aminoisoquinoline (D97) (37 mg, 0.25 mmol) and 4-biphenylcarboxylic acid (75 mg, 0.38 mmol) as an off-white solid. $^1$H NMR (400 MHz, $CDCl_3$) δ (ppm): 9.20 (s, 1H), 8.52 (d, 1H), 8.46 (d, 1H), 8.09 (br.s, 1H), 8.00 (m, 3H), 7.77 (d, 2H), 7.65-7.70 (m, 4H), 7.50 (t, 2H), 7.43 (t, 1H).

Example 130

N-Isoquinolin-5-yl-1-(5-trifluoromethylpyrid-2-yl)-piperidine-4-carboxamide

Using the procedure outlined in Example 107, the title compound was prepared from 1-(5-trifluoromethylpyrid-2-yl)-piperidine-4-carboxylic acid (D101) (100 mg, 0.36 mmol) and 5-aminoisoquinoline (27 mg, 0.19 mmol) as an off white solid. MS(ES): $MH^+$ 401, $M-H^+$ 399.

Example 131

6-(2,4-Difluorophenyl)-2-methyl-N-(1,2,3,4-tetrahydroquinolin-7-yl)nicotinamide

Using the procedure outlined in Example 38, the title compound was prepared from 7-amino-1-trifluoroacetyl-1,2,3,4-tetrahydroquinoline (D5) (73 mg, 0.30 mmol) and 2-methyl-6-(2,4-difluorophenyl)nicotinic acid (D106) (82 mg, 0.33 mmol) then converted to the HCl salt as an off-white solid. $^1$H NMR (400 MHz, MeOH-$d_4$) δ (ppm): 8.46 (d, 1H), 8.11 (d, 1H), 7.93-8.01 (m, 2H), 7.81 (d, 1H), 7.40 (d, 1H), 7.25 (m, 2H), 3.55 (m, 2H), 2.96 (t, 2H), 2.88 (s, 3H), 2.18 (m, 2H).

Example 132

6-(3,4-Difluorophenyl)-2-methyl-N-(1,2,3,4-tetrahydroquinolin-7-yl)nicotinamide

Using the procedure outlined in Example 38, the title compound was prepared from 7-amino-1-trifluoroacetyl-1,2,3,4-tetrahydroquinoline (D5) (73 mg, 0.30 mmol) and 2-methyl-6-(3,4-difluorophenyl)nicotinic acid (D108) (82 mg, 0.33 mmol) then converted to the HCl salt as a buff solid. $^1$H NMR (400 MHz, DMSO) δ (ppm): 8.23 (dd, 1H), 8.04 (m, 3H), 7.87 (d, 1H), 7.63 (d, 1H), 7.57 (m, 1H), 7.29 (d, 1H), 3.34 (m, 2H), 2.80 (m, 2H), 2.67 (s, 3H), 2.02 (m, 2H).

Example 133

N-Quinolin-6-yl-1,1'-biphenyl-4-carboxamide

Using the procedure outlined in Example 56, the title compound was prepared from 6-aminoquinoline (72 mg, 0.75 mmol) and 4-biphenylcarboxylic acid (149 mg, 0.75 mmol) as a white solid. $^1$H NMR (400 MHz, $CDCl_3$) δ (ppm): 9.22 (d, 1H), 8.88 (dd, 1H), 8.52 (d, 1H), 8.33 (dd, 1H), 8.19 (d, 1H), 8.13 (d, 1H), 8.09 (d, 1H), 8.08 (m, 3H), 7.91 (d, 1H), 7.72 (dd, 1H), 7.52 (m, 3H), 7.43 (dd, 1H).

Pharmacological Data (a) In Vitro Assay

As referenced above, the compounds of the invention are vanilloid receptor (VR1) antagonists and hence have useful pharmaceutical properties. Vanilloid receptor (VR1) antagonist activity can be confirmed and demonstrated for any particular compound by use of conventional methods, for example those disclosed in standard reference texts such as D. Le Bars, M. Gozarin and S. W. Cadden, Pharmacological Reviews, 2001, 53(4), 597-652] or such other texts mentioned herein.

The screen used for the compounds of this invention was based upon a FLIPR based calcium assay, similar to that described by Smart et al. (British Journal of Pharmacology, 2000, 129, 227-230). Transfected astrocytoma 1321N1 cells, stably expressing human VR1, were seeded into FLIPR plates at 25,000 cells/well (96-well plate) and cultured overnight.

The cells were subsequently loaded in medium containing 4 µM Fluo-3 AM (Molecular Probes) for 2 hours, at room temperature, in the dark. The plates were then washed 4 times with Tyrode containing 1.5 mM calcium, without probenecid. The cells were pre-incubated with compound or buffer control at room temperature for 30 minutes. Capsaicin (Sigma)

was then added to the cells. Compounds having antagonist activity against the human VR1 were identified by detecting differences in fluorescence when measured after capsaicin addition, compared with no compound buffer controls. Thus, for example, in the buffer control capsaicin addition results in an increase in intracellular calcium concentration resulting in fluorescence. A compound having antagonist activity blocks the capsaicin binding to the receptor, there is no signalling and therefore no increase in intracellular calcium levels and consequently lower fluorescence. pKb values are generated from the $IC_{50}$ values using the Cheng-Prusoff equation.

All compounds tested by the above methodology had pKb>6, preferred compounds having a pKb>7.0.

(b) FCA-Induced Hyperalgesia in the Guinea Pig

100 μl of 1 mg/ml FCA was injected intraplantar into the left paw of 4 groups of 8 male Dunkin Hartley guinea-pigs (batch: 6282434, average weight 340 g). 24 hours later compounds were administered orally at 0 (vehicle), 3, 10 30 mg/kg with vehicle as 1% methylcellulose and dosing volume being 2 ml/kg and dosing straight into the stomach. The methylcellulose was added gradually to the compound into the pestle and mortar and ground together.

Behavioural readouts of mechanical hyperalgesia were obtained before FCA administration (naïve reading), after FCA but before drug administration (predose reading) and 1 hour after drug administration. The readout used was paw pressure (Randall-Sellito) and the end point was paw withdrawal. The paw pressure equipment also had one silver disc placed on the point to increase the markings by a factor of 2.

Compounds having a pKb>7.0 in vitro, according to model (a) above, were tested in this model and shown to be active.

The invention claimed is:

1. A compound of formula (IB),

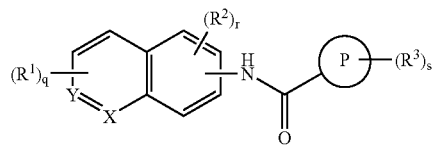

(IB)

or a pharmaceutically acceptable salt thereof,
wherein, P is selected from the group consisting of phenyl, pyridyl, piperidinyl, piperazinyl, and morpholinyl;
$R^1$ is $CH_3$;
$R^2$ is Cl;
each $R^3$ is independently selected from the group consisting of alkyl; alkoxy; —$CF_3$; halo—$O(CH_2)$ $OR^6$; —$O(CH_2)$ $NR^4R^5$; phenyl optionally substituted with one or more $C_1$-$C_6$-alkyl, trifluoromethyl, methoxy, acetyl, halo, or $(CH_3)_2NS(O)_2$-groups cyclohexyl; benzo[1,3]dioxolyl; morpholinyl pyridyl optionally substituted with one or more chloro or methyl groups; piperazinyl optionally substituted with a methoxycarbonyl group; piperidinyl; thienyl; furyl; pyrazolyl; indanyl; oxazolyl; methylthiazolyl; oxadiazolyl; isothiazolyl; isoxazolyl; and thiadiazolyl;
$R^4$ and $R^5$ are each methyl;
$R^6$ is methyl;
X is N and Y is $CR^9$; or X is $CR^9$ and Y is N;
$R^9$ is H or $R^1$;
n is an integer value from 1 to 6;
q is 0 or 1;
r is 0 or 1, and
s is 0, 1, 2 or 3.

2. A pharmaceutical composition, which comprises the compound of claim 1 or a pharmaceutically acceptable salt thereof and a pharmaceutically acceptable carrier or excipient therefor.

3. The compound of claim 1 which is represented by the following formula:

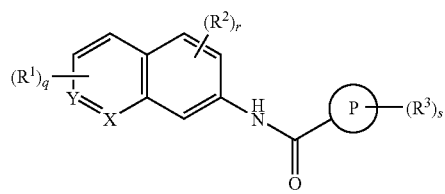

or a pharmaceutically acceptable salt thereof; wherein
P is phenyl or pyridyl;
Y is CH and X is N; or Y is N and X is CH;
each $R^3$ is independently; —$CF_3$; methyl; fluoro; chloro; bromo; morpholinyl; piperidinyl;
thienyl; pyrazolyl; methylthiazolyl; phenyl optionally substituted with one or more substituents selected from the group consisting of methyl, trifluoromethyl, methoxy, and chloro; or pyridyl optionally substituted with methyl or chloro;
q is 0;
r is 0; and
s is 1, 2, or 3.

4. The compound of claim 3 which is represented by the following structure:

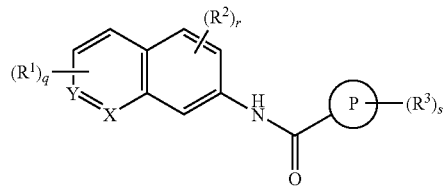

or a pharmaceutically acceptable salt thereof; wherein
P is phenyl;
Y is CH; and
X is N.

5. The compound of claim 3 or a pharmaceutically acceptable salt thereof wherein:
P is pyridyl;
Y is CH; and
X is N.

6. The compound of claim 1 or a pharmaceutically acceptable salt thereof which is represented by the following formula:

7. The compound of claim 1 or a pharmaceutically acceptable salt thereof which is represented by the following formula:
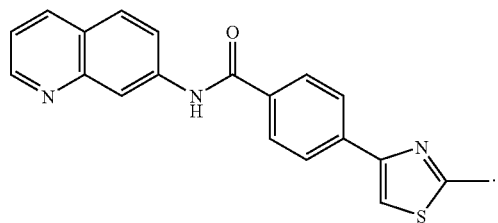
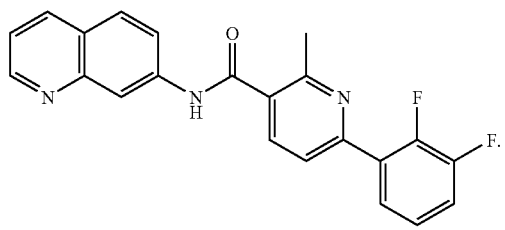
* * * * *